United States Patent
Jung et al.

(10) Patent No.: US 9,537,104 B2
(45) Date of Patent: Jan. 3, 2017

(54) CONDENSED-CYCLIC COMPOUND AND ORGANIC LIGHT-EMITTING DIODE INCLUDING THE CONDENSED-CYCLIC COMPOUND

(71) Applicant: Samsung Display Co., Ltd., Yongin, Gyeonggi-do (KR)

(72) Inventors: Hye-Jin Jung, Yongin (KR); Seok-Hwan Hwang, Yongin (KR); Young-Kook Kim, Yongin (KR); Jin-O Lim, Yongin (KR); Sang-Hyun Han, Yongin (KR); Eun-Jae Jeong, Yongin (KR); Soo-Yon Kim, Yongin (KR); Jun-Ha Park, Yongin (KR); Eun-Young Lee, Yongin (KR); Chang-Ho Lee, Yongin (KR); Jong-Hyuk Lee, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 498 days.

(21) Appl. No.: 13/800,144

(22) Filed: Mar. 13, 2013

(65) Prior Publication Data

US 2014/0077175 A1  Mar. 20, 2014

(30) Foreign Application Priority Data

Sep. 17, 2012  (KR) .................. 10-2012-0102993

(51) Int. Cl.
*H01L 51/00* (2006.01)
*C07D 213/06* (2006.01)
(Continued)

(52) U.S. Cl.
CPC .......... *H01L 51/006* (2013.01); *C07D 209/86* (2013.01); *C07D 213/06* (2013.01);
(Continued)

(58) Field of Classification Search
None
See application file for complete search history.

(56) References Cited

U.S. PATENT DOCUMENTS 5,635,308 A  6/1997  Inoue et al.
5,972,247 A  10/1999  Shi et al.
(Continued)

FOREIGN PATENT DOCUMENTS

CN  103570560 A  2/2014
JP  8-12600  1/1996
(Continued)

OTHER PUBLICATIONS

Nicklas Johansson, Josef Salbeck, Jacqueline Bauer, Frank Weissörtel, Per Bröms, Annica Andersson and William R. Saloneck, Solid State Amplified Spontaneous Emission in Some Spiro-Type Molecules: A New Concept for the Design of Solid-State Lasing Molecules, Communications, 1998, vol. 10, No. 14, Advanced Materials.
(Continued)

Primary Examiner — J. L. Yang
(74) Attorney, Agent, or Firm — Knobbe Martens Olson & Bear LLP

(57) ABSTRACT

A condensed-cyclic compound and an organic light-emitting diode including the condensed-cyclic compound.

17 Claims, 1 Drawing Sheet

(51) Int. Cl.
| | |
|---|---|
| C07D 213/16 | (2006.01) |
| C07D 403/10 | (2006.01) |
| C07D 213/22 | (2006.01) |
| C07D 471/04 | (2006.01) |
| C07D 235/18 | (2006.01) |
| C07D 251/24 | (2006.01) |
| C07D 401/14 | (2006.01) |
| C07D 215/04 | (2006.01) |
| C07D 215/12 | (2006.01) |
| C07D 401/04 | (2006.01) |
| C07D 401/10 | (2006.01) |
| C07D 405/04 | (2006.01) |
| C07D 409/14 | (2006.01) |
| C07D 413/10 | (2006.01) |
| C07D 241/12 | (2006.01) |
| C07D 417/10 | (2006.01) |
| C07D 487/04 | (2006.01) |
| C07D 213/127 | (2006.01) |
| C07D 213/26 | (2006.01) |
| C07D 213/57 | (2006.01) |
| C07D 209/86 | (2006.01) |
| H01L 51/50 | (2006.01) |

(52) U.S. Cl.
CPC ....... *C07D 213/127* (2013.01); *C07D 213/16* (2013.01); *C07D 213/22* (2013.01); *C07D 213/26* (2013.01); *C07D 213/57* (2013.01); *C07D 215/04* (2013.01); *C07D 215/12* (2013.01); *C07D 235/18* (2013.01); *C07D 241/12* (2013.01); *C07D 251/24* (2013.01); *C07D 401/04* (2013.01); *C07D 401/10* (2013.01); *C07D 401/14* (2013.01); *C07D 403/10* (2013.01); *C07D 405/04* (2013.01); *C07D 409/14* (2013.01); *C07D 413/10* (2013.01); *C07D 417/10* (2013.01); *C07D 471/04* (2013.01); *C07D 487/04* (2013.01); *H01L 51/0054* (2013.01); *H01L 51/0067* (2013.01); *H01L 51/0072* (2013.01); *H01L 51/5072* (2013.01)

(56) References Cited

U.S. PATENT DOCUMENTS

| | | |
|---|---|---|
| 6,465,115 B2 | 10/2002 | Shi et al. |
| 6,596,415 B2 | 7/2003 | Shi et al. |
| 2004/0115476 A1* | 6/2004 | Oshiyama et al. ........... 428/690 |
| 2007/0231503 A1* | 10/2007 | Hwang et al. ................ 428/1.1 |
| 2008/0284322 A1 | 11/2008 | Hosokawa et al. |
| 2009/0085468 A1 | 4/2009 | Funahashi et al. |
| 2009/0230854 A1* | 9/2009 | Kim et al. .................... 313/504 |
| 2014/0027721 A1 | 1/2014 | Kim et al. |

FOREIGN PATENT DOCUMENTS

| | | |
|---|---|---|
| JP | 10-017860 | 1/1998 |
| JP | 11-087067 | 3/1999 |
| JP | 2000-003782 | 1/2000 |
| KR | 10-2008-0031931 A | 4/2008 |
| KR | 10-2008-0068862 A | 7/2008 |
| KR | 1020090085939 A | 8/2009 |
| KR | 10-2009-00985589 A | 9/2009 |
| KR | 10200900093674 A | 9/2009 |
| KR | 1020110018195 A | 2/2011 |

OTHER PUBLICATIONS

Y.T. Tao, E. Balasubramaniam, A. Danel, B. Jarosz and P. Tomasik, Sharp green electroluminescence from 1H-pyrazolo[3,4-b]quinolone-based light-emitting diodes, Applied Physics Letters, Sep. 11, 2000, 1575-1577, vol. 77, No. 11, American Institute of Physics.

Office Action mailed Aug. 31, 2016, issued in Corresponding CN Application No. 201310413921.6.

* cited by examiner

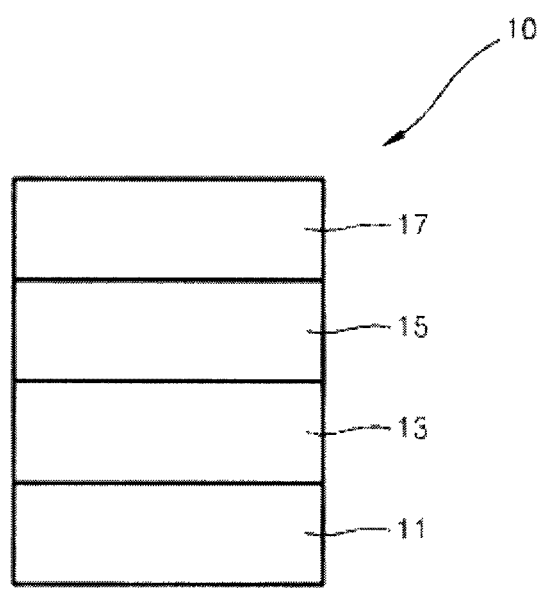

CONDENSED-CYCLIC COMPOUND AND ORGANIC LIGHT-EMITTING DIODE INCLUDING THE CONDENSED-CYCLIC COMPOUND

CROSS-REFERENCE TO RELATED APPLICATIONS

This application claims the benefit of Korean Patent Application No. 10-2012-0102993, filed on Sep. 17, 2012, in the Korean Intellectual Property Office, the disclosure of which is incorporated herein in its entirety by reference.

BACKGROUND

Field

One or more embodiments relate to a compound for an organic light-emitting diode and an organic light-emitting diode including the compound.

Description of the Related Technology

Organic light-emitting diodes (OLEDs), which are self-emitting device, have advantages such as a wide viewing angle, excellent contrast, quick response, high brightness, and excellent driving voltage, and can provide multicolored images.

A general OLED has a structure including a substrate, an anode, a hole transport layer (HTL), an emission layer (EML), an electron transport layer (ETL), and a cathode which are sequentially stacked on the substrate. In this regard, the HTL, the EML, and the ETL are organic layers formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

The present embodiments provide a condensed-cyclic compound having a novel structure and an organic light-emitting diode including the condensed-cyclic compound.

According to an aspect of the present embodiments, there is provided a condensed-cyclic compound represented by Formula 1 below:

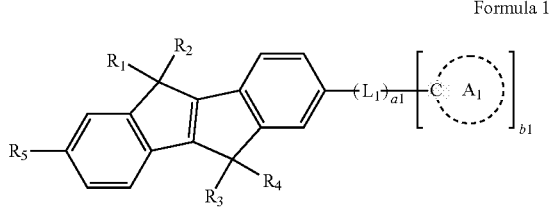

Formula 1 wherein $A_1$ may be a substituted or unsubstituted $C_2$-$C_{60}$ heteroaryl group containing at least one of N, O, and S as a ring-forming atom;

$L_1$ may be a substituted or unsubstituted $C_6$-$C_{60}$ arylene group or a substituted or unsubstituted $C_2$-$C_{60}$ heteroarylene group;

a1 may be an integer of 0 to 5;

b1 may be an integer of 1 to 5; and $R_1$ through $R_5$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

According to another aspect of the present embodiments, there is provided an organic light-emitting diode including a first electrode; a second electrode facing the first electrode; and an organic layer interposed between the first electrode and the second electrode, wherein the organic layer includes at least one of the condensed-cyclic compounds represented by Formula 1 described above.

BRIEF DESCRIPTION OF THE DRAWINGS

The above and other features and advantages of the present embodiments will become more apparent by describing example embodiments thereof with reference to the attached drawing in which:

FIG. 1 is a schematic diagram illustrating an organic light-emitting diode (OLED) according to an embodiment.

DETAILED DESCRIPTION

Hereinafter, example embodiments will be described with reference to the accompanying drawing. As used herein, the term "and/or" includes any and all combinations of one or more of the associated listed items. Expressions such as "at least one of," when preceding a list of elements, modify the entire list of elements and do not modify the individual elements of the list.

According to an embodiment, there is provided a condensed-cyclic compound represented by Formula 1 below:

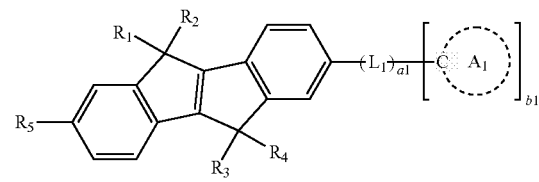

Formula 1

In Formula 1, $A_1$ is a substituted or unsubstituted $C_2$-$C_{60}$ heteroaryl group containing at least one of N, O, and S as a ring-forming atom.

$A_1$ may be an electron-transporting moiety.

$A_1$ may be a substituted or unsubstituted $C_2$-$C_{20}$ heteroaryl group containing at least one of N, O, and S as a ring-forming atom.

For example, A1 may be a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or substituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted isoquinolinyl group, a substituted or unsubstituted phenanthrolinyl group, a substituted or unsubstituted benzothiazolyl group, or a substituted or unsubstituted benzooxazolyl group.

For example, $A_1$ may be a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted quinolinyl group, a substituted or unsubstituted carbazolyl group, a substituted or unsubstituted dibenzothiophenyl group, a substituted or unsubstituted dibenzofuranyl group, a substituted or unsubstituted triazinyl group, a substituted or unsubstituted isoquinolinyl group, a substituted or unsubstituted phenanthrolinyl group, a substituted or unsubstituted benzothiazolyl group, or a substituted or unsubstituted benzooxazolyl group.

According to some embodiments, $A_1$ may be one of Formulae 3A through 3O, but is not limited thereto:

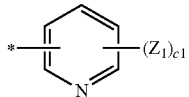

Formula 3A

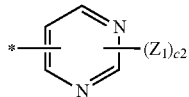

Formula 3B

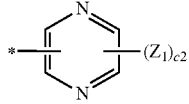

Formula 3C

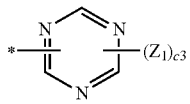

Formula 3D

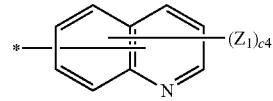

Formula 3E

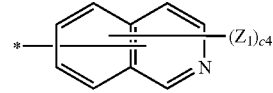

Formula 3F

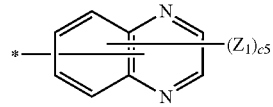

Formula 3G

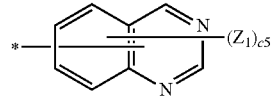

Formula 3H

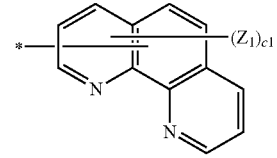

Formula 3I

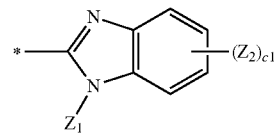

Formula 3J

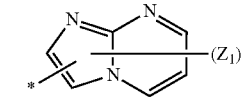

Formula 3K

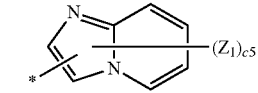

Formula 3L

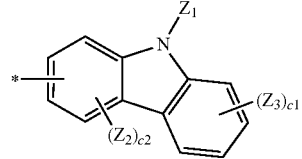

Formula 3M

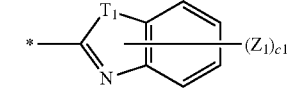

Formula 3N

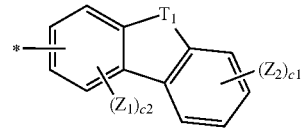

Formula 3O

In Formulae 3A through 3O, $Z_1$ through $Z_3$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_3$-$C_{60}$ alkoxy group, a $C_3$-$C_{60}$ cycloalkyl group, a $C_3$-$C_{60}$ cycloalkenyl group, a $C_6$-$C_{60}$ aryl group, a $C_6$-$C_{60}$ aryl group that is substituted with at least one of —F, —CN, and a $C_1$-$C_{10}$ alkyl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

For example, $Z_1$ through $Z_3$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, a phenyl group, a naphthyl group, an anthryl group, a fluorenyl group, a pyrenyl group, a phenyl group that is substituted with at least one of —F, —CN, and a $C_1$-$C_{10}$ alkyl group, a naphthyl group that is substituted with at least one of —F, —CN, and a $C_1$-$C_{10}$ alkyl group, an anthryl group that is substituted with at least one of —F, —CN, and a $C_1$-$C_{10}$ alkyl group, a fluorenyl group that is substituted with at least one of —F, —CN, and a $C_1$-$C_{10}$ alkyl group, a pyrenyl group that is substituted with at least one of —F, —CN, and a $C_1$-$C_{10}$ alkyl group, a pyridinyl group, a dibenzothiophenyl group, or a dibenzofuranyl group.

$Z_1$ through $Z_3$ may be each independently hydrogen, a phenyl group, a naphthyl group, an anthryl group, a fluorenyl group, a pyrenyl group, a fluorophenyl group, a difluorophenyl group, a cyanophenyl group, a fluoronaphthyl group, a fluoronaphthyl group, a cyanonaphthyl group, a fluorofluorenyl group, a difluorofluorenyl group, a cyanofluorenyl group, a dimethylfluorenyl group, a pyridinyl group, a dibenzothiophenyl group, or a dibenzofuranyl group.

In Formulae 3A through 3O, c1 may be an integer of 1 to 4; c2 may be an integer of 1 to 3; c3 may be an integer of 1 to 2; c4 may be an integer of 1 to 6; and c5 may be an integer of 1 to 5. For example, c1 through c5 may be each independently 1 or 2.

In Formulae 3N and 3O, $T_1$ may be O or S.

$A_1$ may be one of Formulae 4A through 4R.

Formula 4A
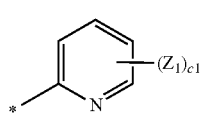

Formula 4B
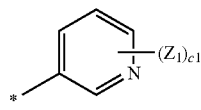

Formula 4C
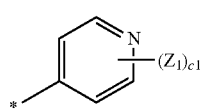

Formula 4D
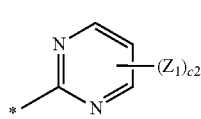

Formula 4E
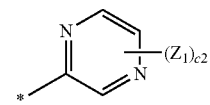

Formula 4F
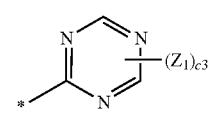

Formula 4G
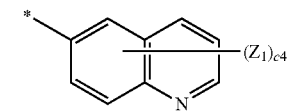

Formula 4H
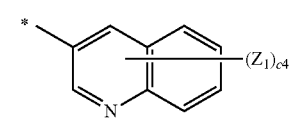

Formula 4I
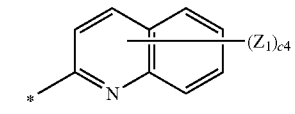

Formula 4J
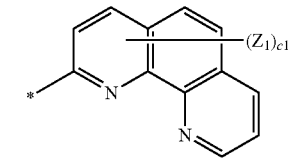

Formula 4K
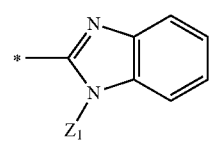

Formula 4L
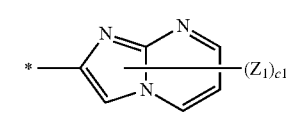

Formula 4M
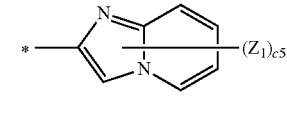

Formula 4N
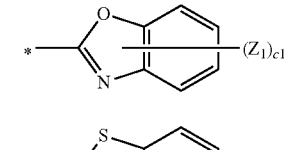

Formula 4O
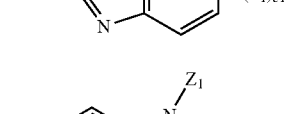

Formula 4P
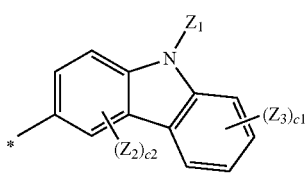

-continued

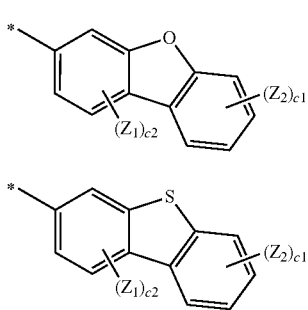

Formula 4Q

Formula 4R

In Formulae 4A through 4R, a detailed description of $Z_1$ through $Z_3$ and c1 through c5 has already been described above.

In Formula 1, $L_1$ may be a substituted or unsubstituted $C_6$-$C_{60}$ arylene group or a substituted or unsubstituted $C_2$-$C_{60}$ heteroarylene group.

For example, $L_1$ may be a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted purinylene group, a substituted or unsubstituted quinolinylene group, a substituted or unsubstituted benzoquinolinylene group, a substituted or unsubstituted phthalazinylene group, a substituted or unsubstituted naphthyridinylene group, a substituted or unsubstituted quinoxalinylene group, a substituted or unsubstituted quinazolinylene group, a substituted or unsubstituted cinnolinylene group, a substituted or unsubstituted carbazolylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzooxazolylene group, a substituted or unsubstituted benzoimidazolylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted thiazolylene group, a substituted or unsubstituted isothiazolylene group, a substituted or unsubstituted benzothiazolylene group, a substituted or unsubstituted isoxazolylene group, a substituted or unsubstituted oxazolylene group, a substituted or unsubstituted triazolylene group, a substituted or unsubstituted tetrazolylene group, a substituted or unsubstituted oxadiazolylene group, a substituted or unsubstituted triazinylene group, a substituted or unsubstituted benzooxazolylene group, a substituted or unsubstituted dibenzofuranylene group, a substituted or unsubstituted dibenzothiophenylene, or a substituted or unsubstituted benzocarbazolylene group.

$L_1$ may be a substituted or unsubstituted phenylene group, a substituted or unsubstituted naphtylene group, a substituted or unsubstituted fluorenylene group, a substituted or unsubstituted spiro-fluorenylene group, a substituted or unsubstituted anthrylene group, a substituted or unsubstituted pyridinylene group, a substituted or unsubstituted pyrimidinylene group, a substituted or unsubstituted quinolinylene group, or a substituted or unsubstituted carbazolylene group.

According to some embodiments, $L_1$ may be one of Formulae 5A through 5M, but is not limited thereto:

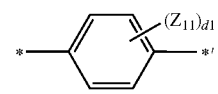

Formula 5A

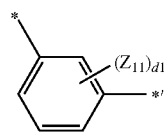

Formula 5B

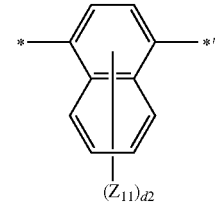

Formula 5C

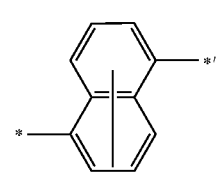

Formula 5D

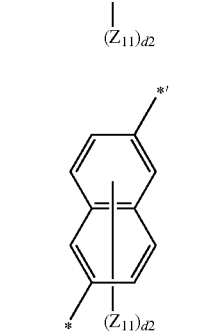

Formula 5E

-continued

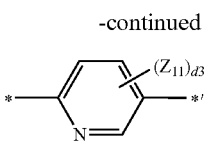
Formula 5F

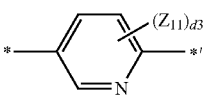
Formula 5G

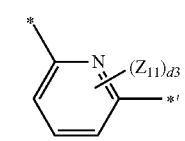
Formula 5H

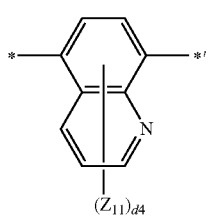
Formula 5I

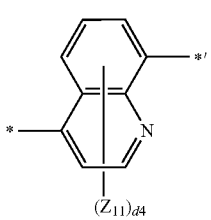
Formula 5J

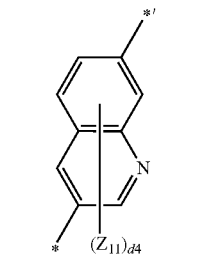
Formula 5K

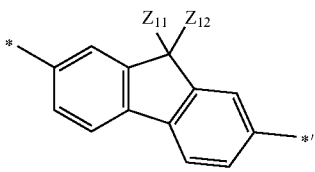
Formula 5L

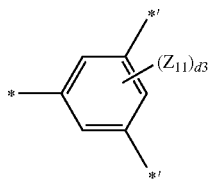
Formula 5M

In Formulae 5A through 5M, $Z_{11}$ and $Z_{12}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_3$-$C_{60}$ cycloalkenyl group, a $C_6$-$C_{60}$ aryl group, a $C_6$-$C_{60}$ aryl group that is substituted with at least one of —F, —CN, and a $C_1$-$C_{10}$ alkyl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

For example, $Z_{11}$ and $Z_{12}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, a phenyl group, a naphthyl group, an anthryl group, a fluorenyl group, a pyrenyl group, a phenyl group that is substituted with at least one of —F, —CN, and a $C_1$-$C_{10}$ alkyl group, a naphthyl group that is substituted with at least one of —F, —CN, and a $C_1$-$C_{10}$ alkyl group, an anthryl group that is substituted with at least one of —F, —CN, and a $C_1$-$C_{10}$ alkyl group, a fluorenyl group that is substituted with at least one of —F, —CN, and a $C_1$-$C_{10}$ alkyl group, a pyrenyl group that is substituted with at least one of —F, —CN, and a $C_1$-$C_{10}$ alkyl group, a pyridinyl group, a dibenzothiophenyl group, or a dibenzofuranyl group.

$Z_{11}$ and $Z_{12}$ may be each independently hydrogen, a methyl group, an ethyl group, a propyl group, a butyl group, or a pentyl group.

In Formulae 5A through 5M, d1 may be an integer of 1 to 4; d2 may be an integer of 1 to 6; d3 may be an integer of 1 to 3; and d4 may be an integer of 1 to 5.

In Formulae 5A through 5M, *' denotes a binding site with $A_1$.

Formula 5M has two binding sites *', and may be $L_1$ of Formula 1 where b1 is 2 (for example, see Compound 36 below).

In Formula 1, a1 may be an integer of 0 to 5. When a1 is an integer of at least 2, at least two $L_1$ groups may be identical to or different from each other. For example, a1 may be 0 or 1. When a1 is 0, $A_1$ may be directly linked to the core of Formula 1.

In Formula 1, b1 may be an integer of 1 to 5. When b1 is an integer of at least 2, at least two $A_1$ groups may be identical to or different from each other. For example, b1 may be 1 or 2.

In Formula 1, $R_1$ through $R_5$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

For example, in Formula 1, $R_1$ through $R_4$ may be each independently a methyl group, an ethyl group, a propyl group, a butyl group, a pentyl group, a phenyl group, a naphthyl group, an anthryl group, or a fluorenyl group.

According to an embodiment, in Formula 1, $R_1$ through $R_4$ may be identical to each other.

According to another embodiment, in Formula 1, $R_1$ and $R_2$ may be linked to each other by a single bond, and $R_3$ and $R_4$ may be linked to each other by a single bond. For example, in Formula 1, R1 through R4 may be each independently a phenyl group, $R_1$ and $R_2$ may be linked to each other by a single bond, and $R_3$ and $R_4$ may be linked to each other by a single bond (see Compounds 72 and 73 below).

For example, the condensed-cyclic compound may be represented by Formula 1A or 1B, but is not limited thereto:

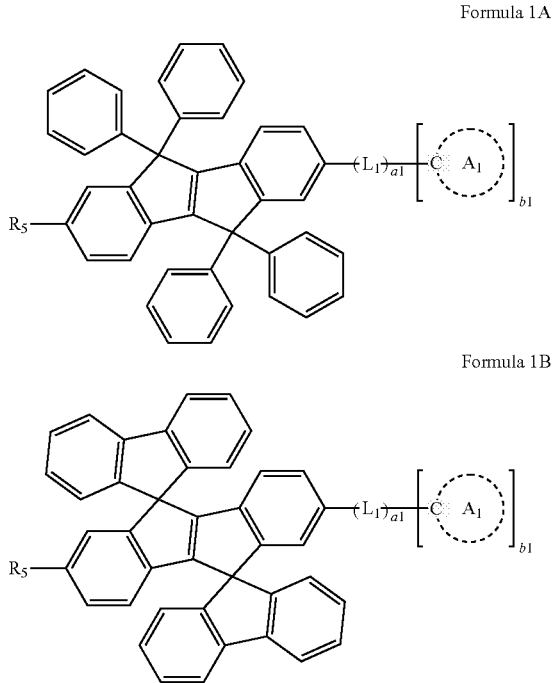

Formula 1A

Formula 1B

A detailed description of 1A and 1B has been already described above.

In Formula 1, $R_5$ may be a substituted or unsubstituted phenyl group, a substituted or unsubstituted pentalenyl group, a substituted or unsubstituted indenyl group, a substituted or unsubstituted naphtyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted isoquinolinyl group, substituted or unsubstituted phenanthrolinyl group, a substituted or unsubstituted benzothiazolyl group, or a substituted or unsubstituted benzooxazolyl group.

For example, in Formula 1, $R_5$ may be a substituted or unsubstituted phenyl group, a substituted or unsubstituted naphtyl group, a substituted or unsubstituted fluorenyl group (e.g., a fluorenyl group that is substituted with at least one of a methyl group, an ethyl group, a propyl group, a butyl group, a pentyl group, and a phenyl group), a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrimidinyl group, a substituted or unsubstituted benzoimidazolyl group, a substituted or unsubstituted quinolinyl group, a substituted or unsubstituted carbazolyl group, a substituted or unsubstituted benzoimidazolyl group, a substituted or unsubstituted dibenzothiophenyl group, a substituted or unsubstituted dibenzofuranyl group, a substituted or unsubstituted triazinyl group, a substituted or unsubstituted isoquinolinyl group, a substituted or unsubstituted phenanthrolinyl group, a substituted or unsubstituted benzothiazolyl group, or a substituted or unsubstituted benzooxazolyl group, but is not limited thereto.

The condensed-cyclic compound of Formula 1 may be, for example, one of Compounds 1 through 74, but is not limited thereto:

1
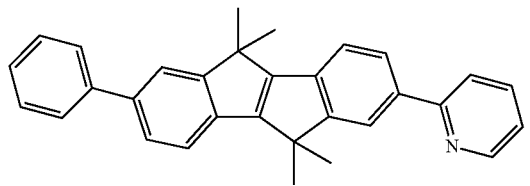
2
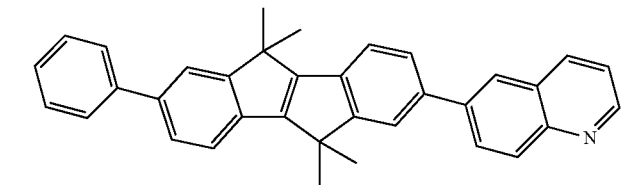
3
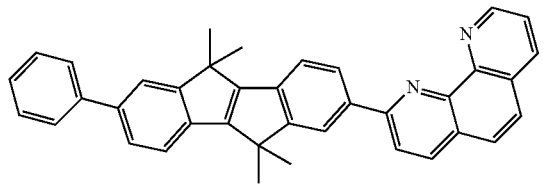
4
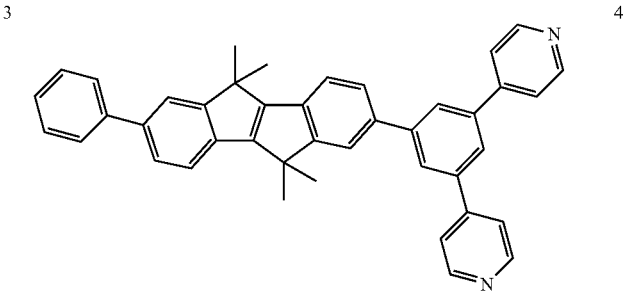
5
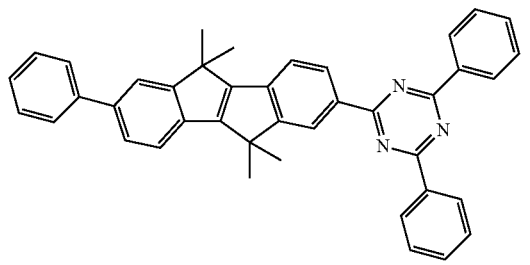
6
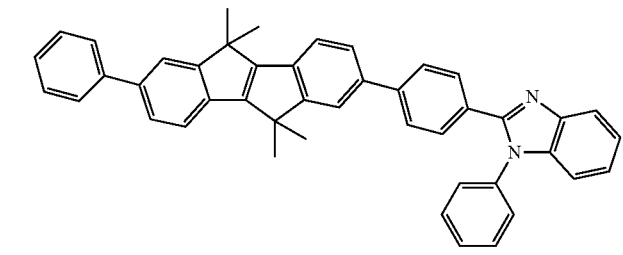
7
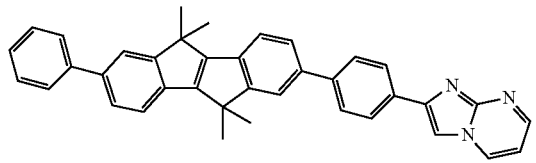
8
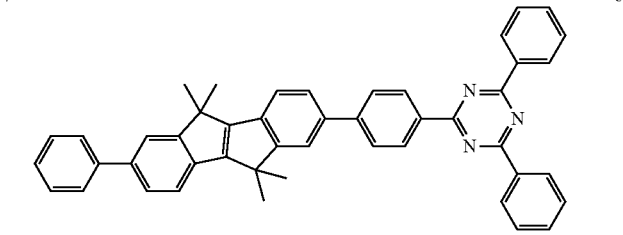
9
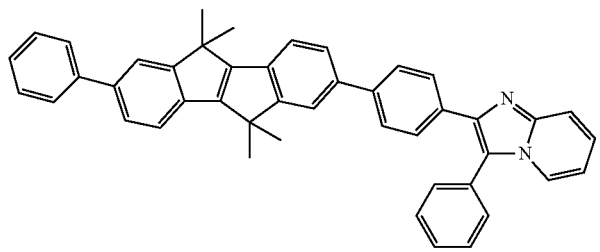
10
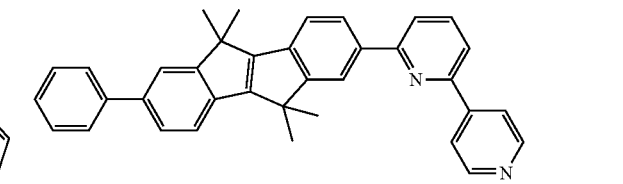
11
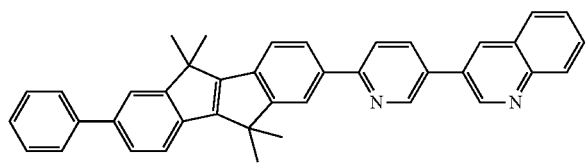
12
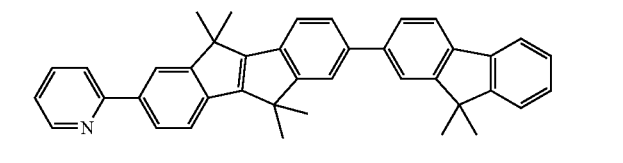

-continued
13
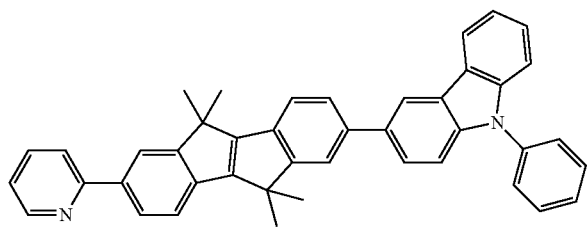
14
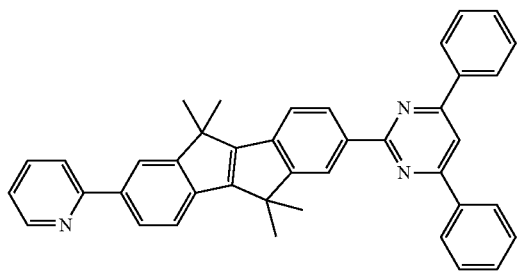
15
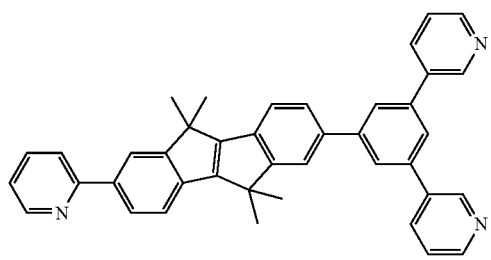
16
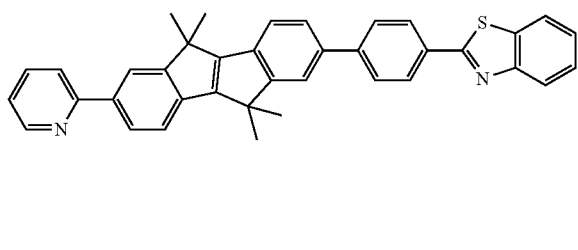
17
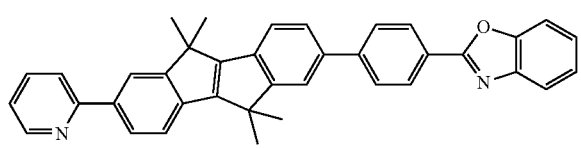
18
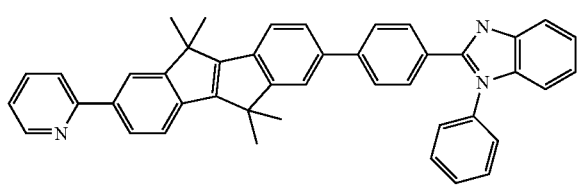
19
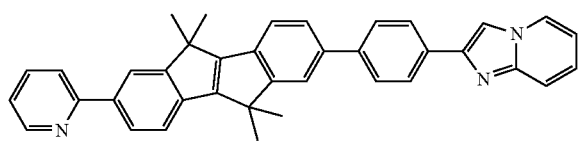
20
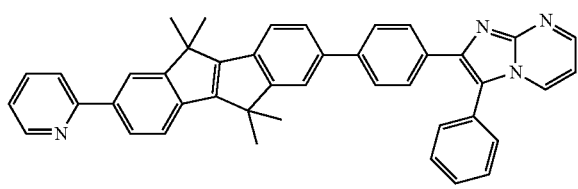
21
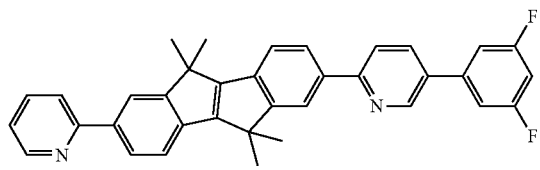
22
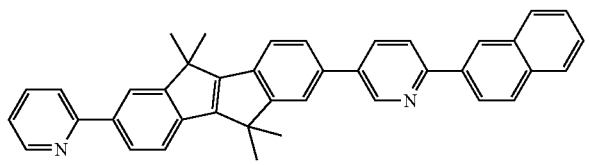
23
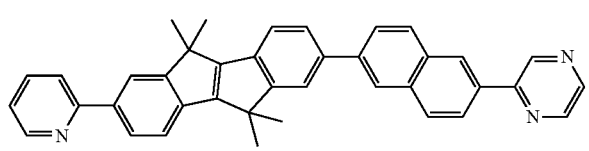
24
25
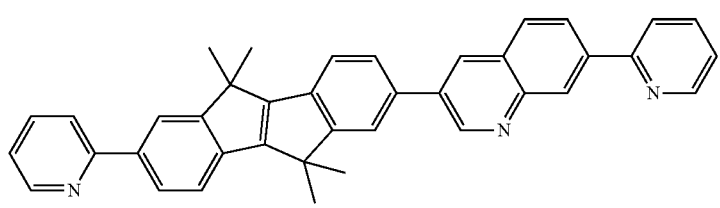

-continued
26
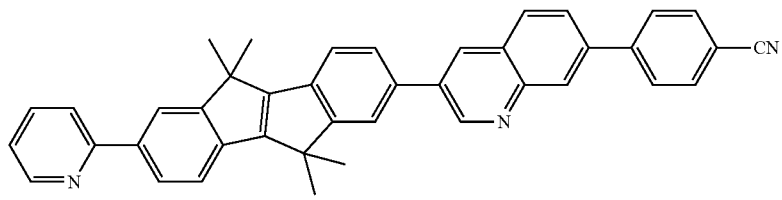
27
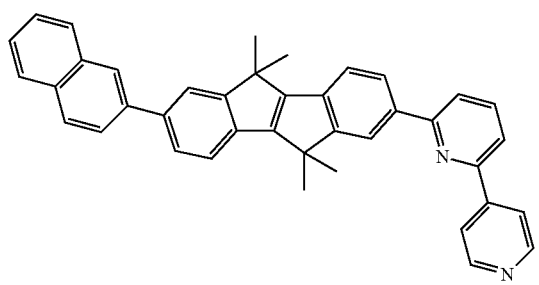
28
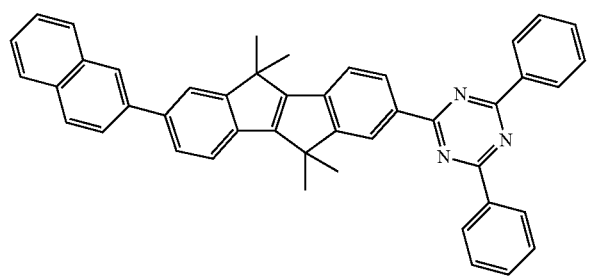
29
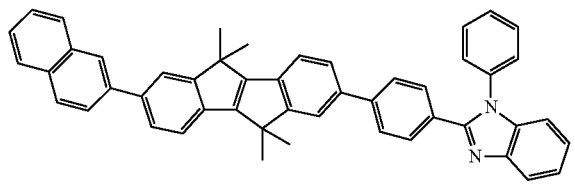
30
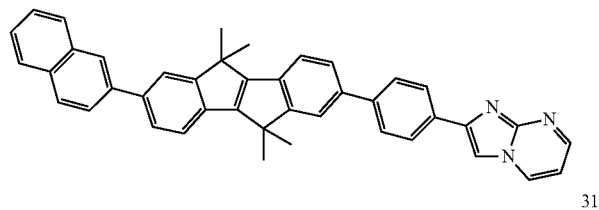
31
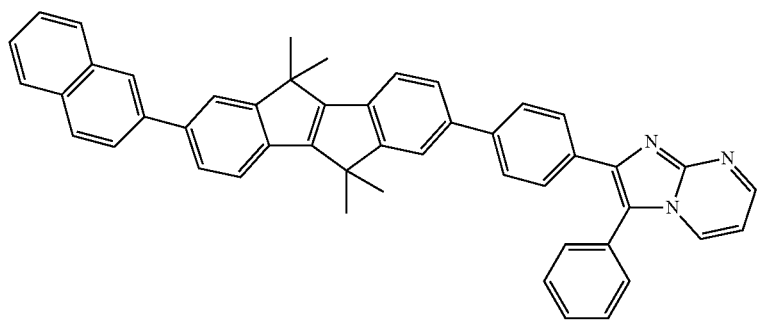
32
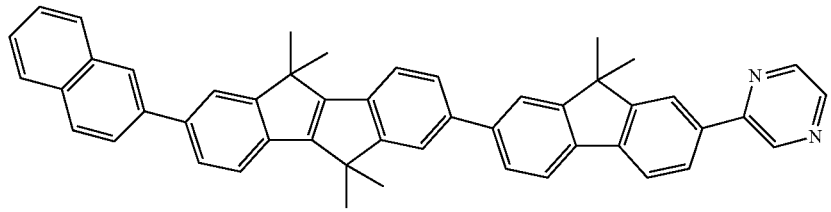
33
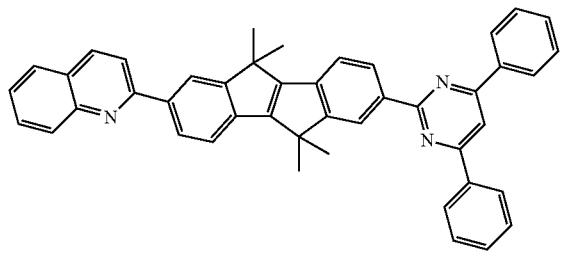
34
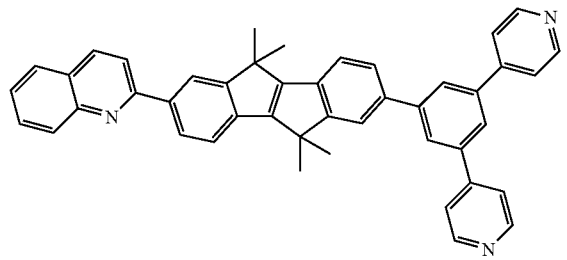

-continued
35
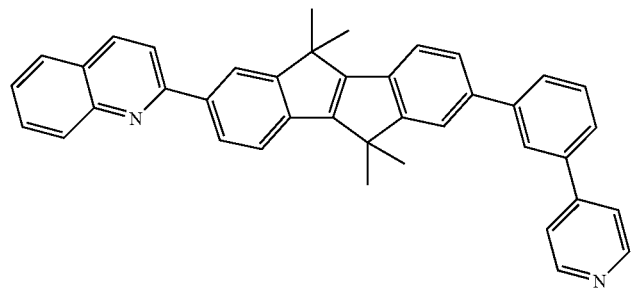
36
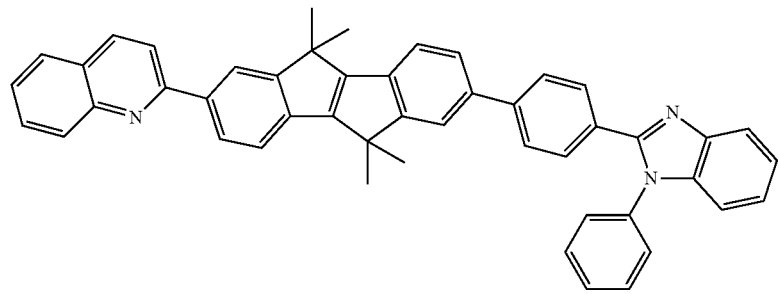
37
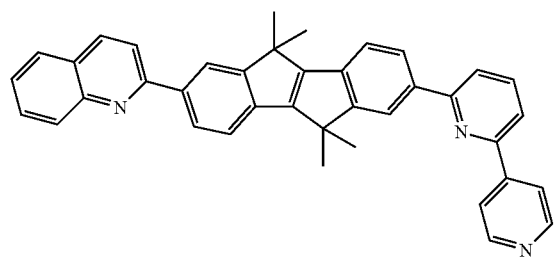
38
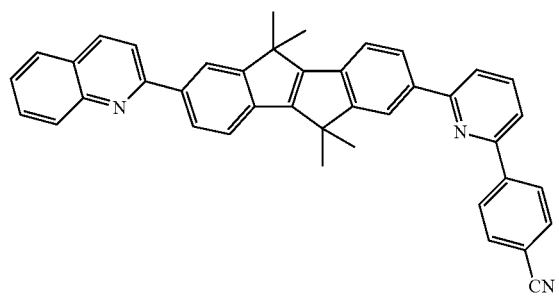
39
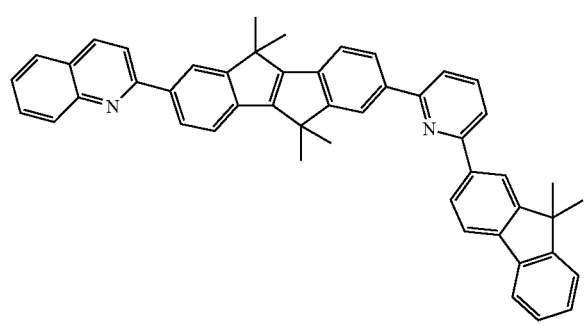
40
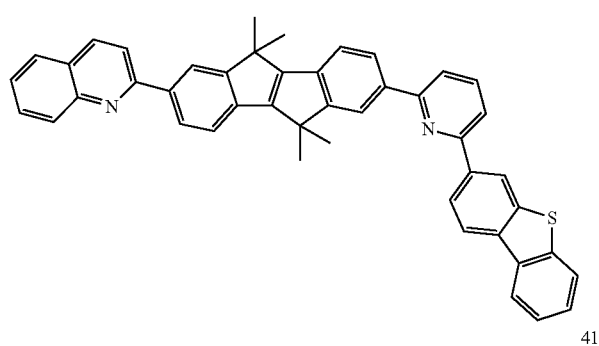
41
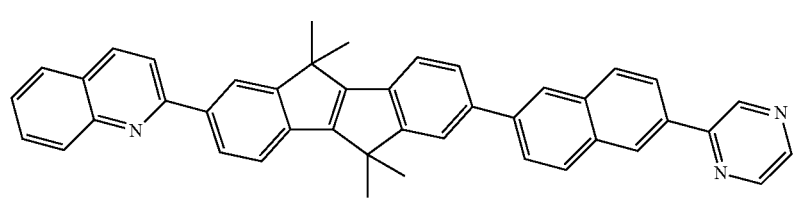
42
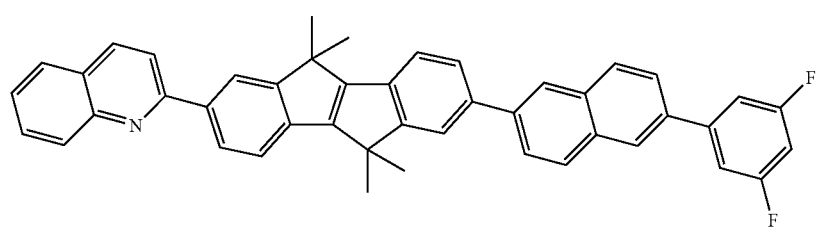

-continued
43
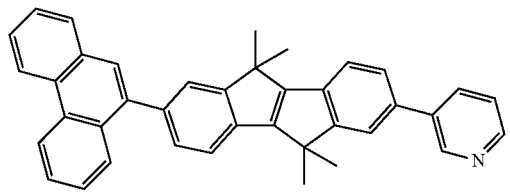
44
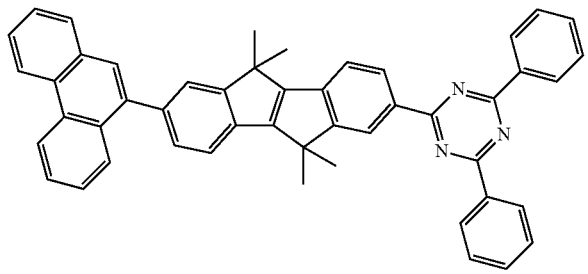
45
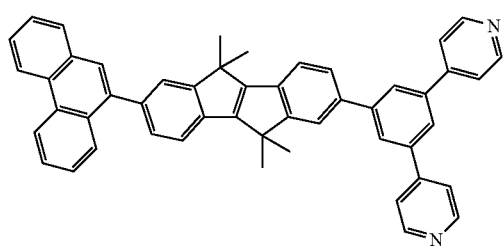
46
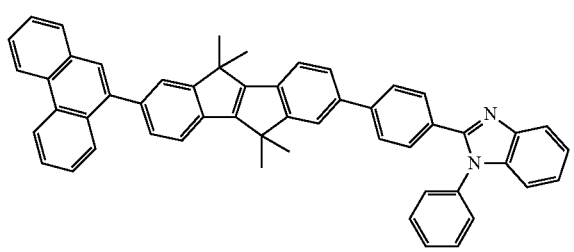
47
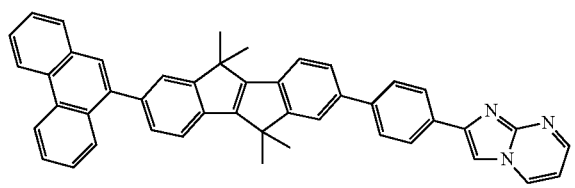
48
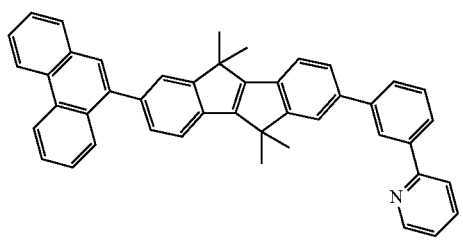
49
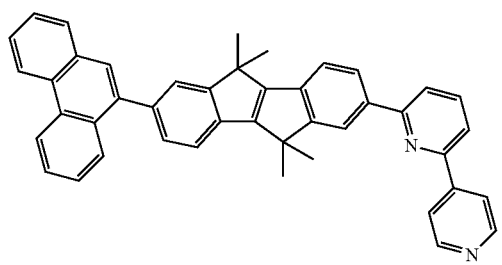
50
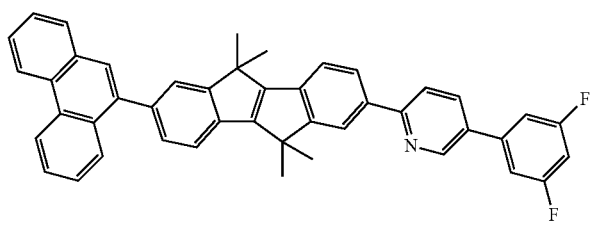
51
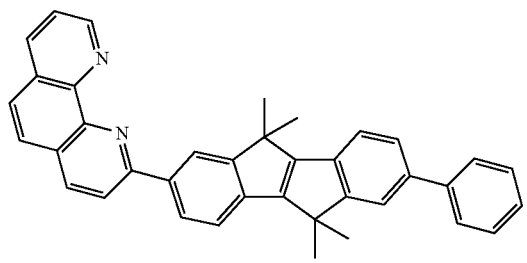
52
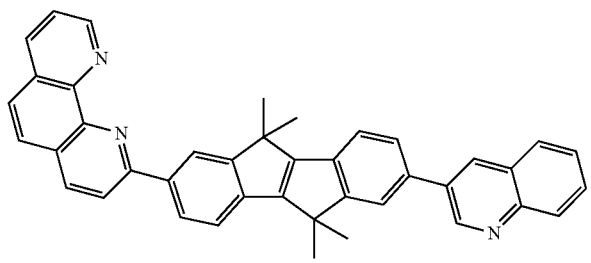

-continued
53
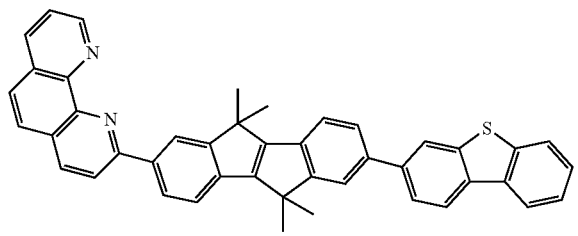
54
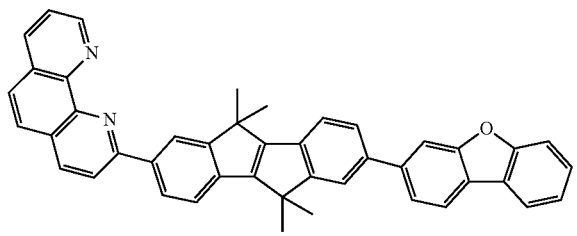
55
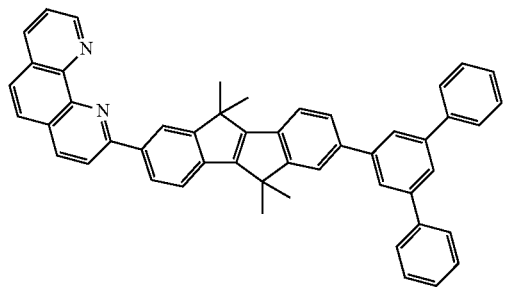
56
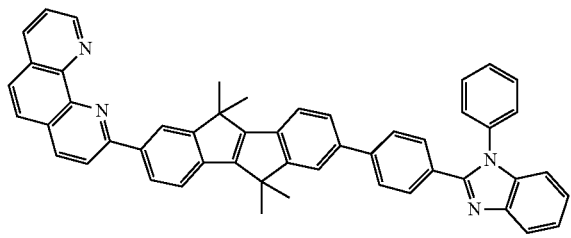
57
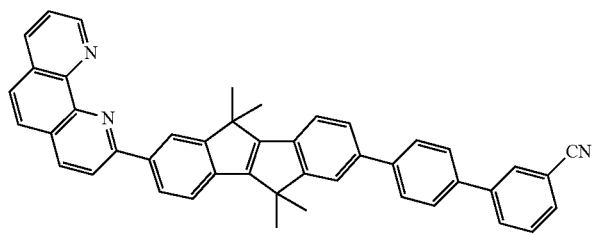
58
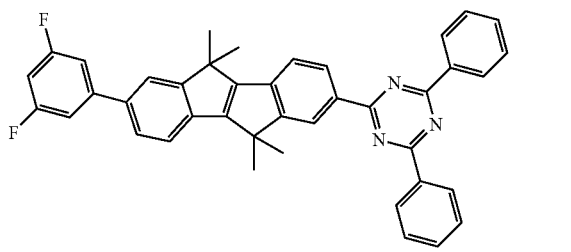
59
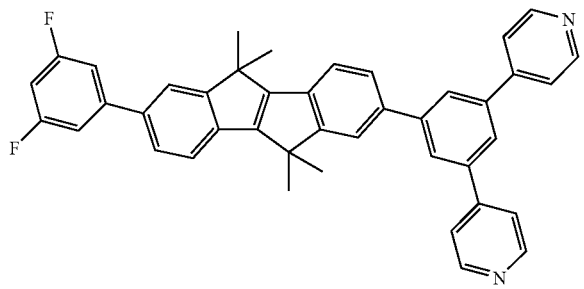
60
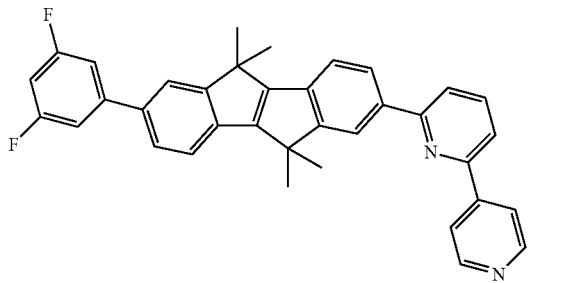
61
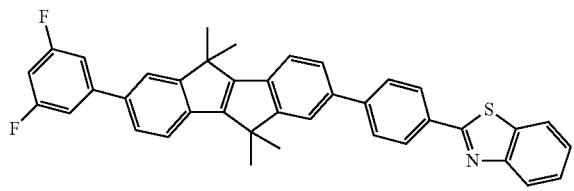
62
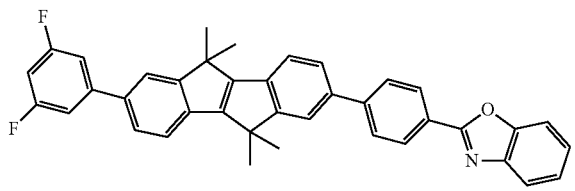

63
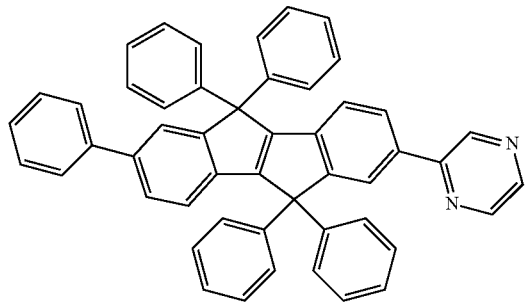
64
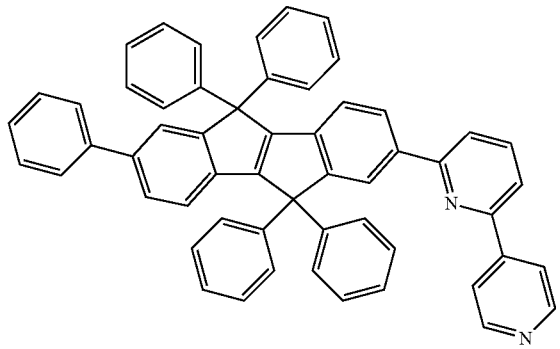
65
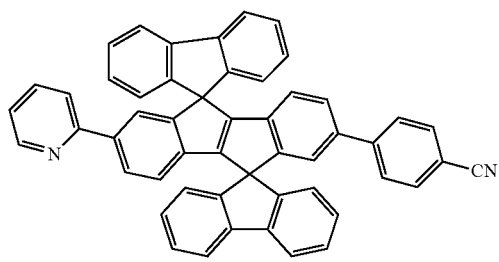
66
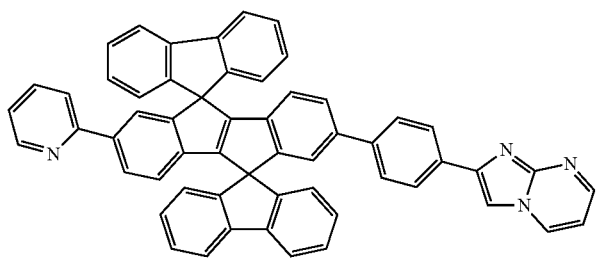
67
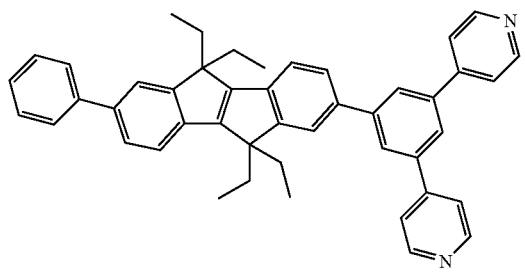
68
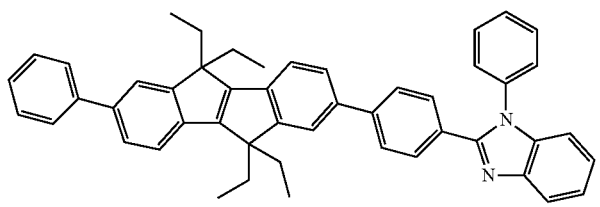
69
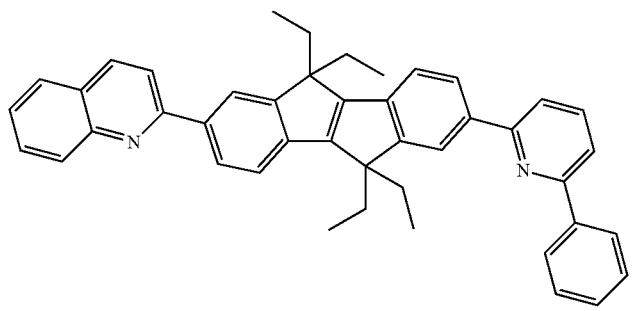
70
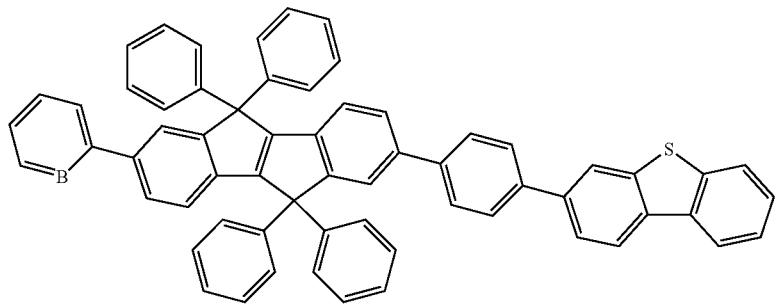

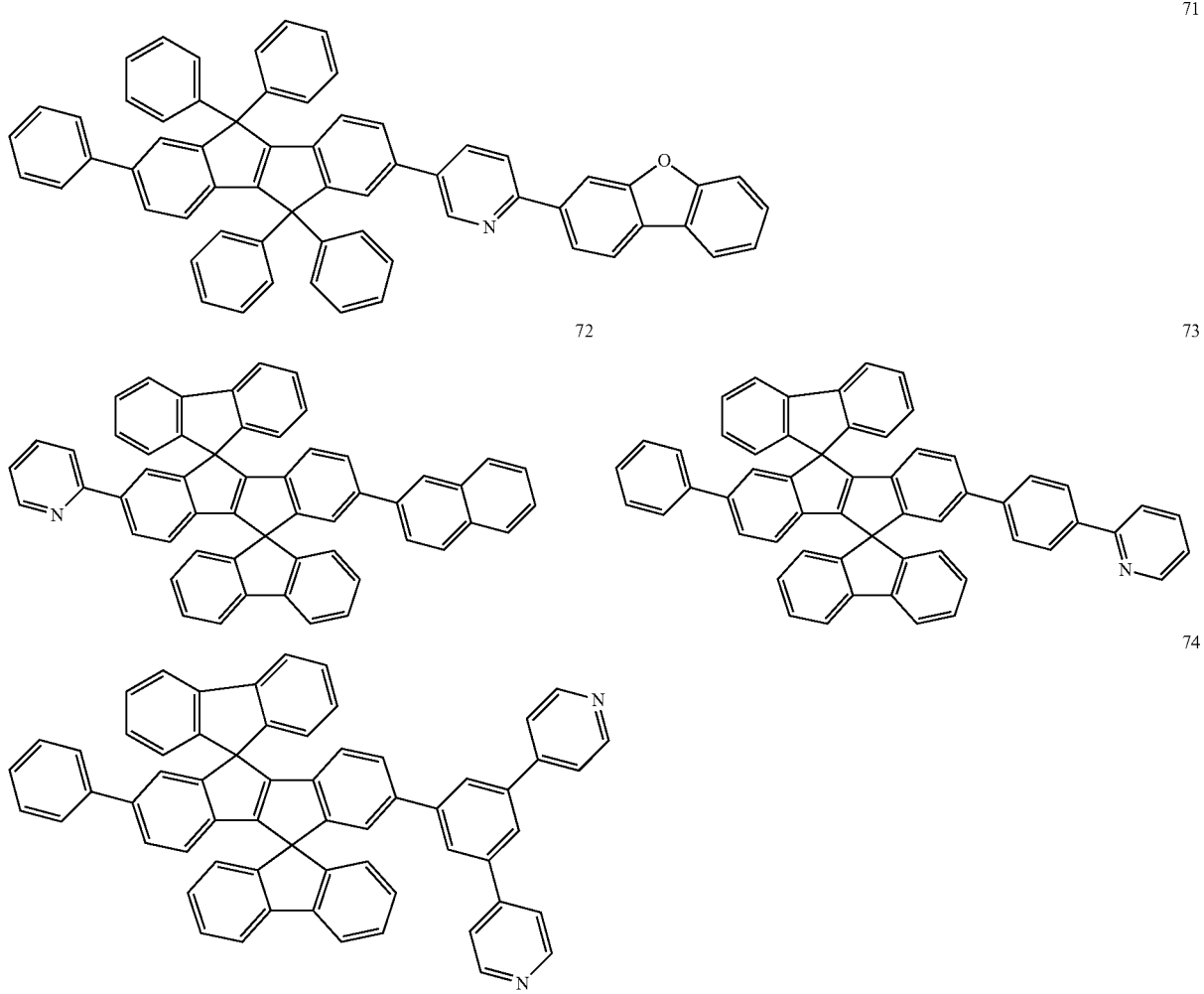

In Formula 1, "carbon" of the ring-forming atom of $A_1$ may be linked to the core of Formula 1 (a1=0) or $L_1$ (a1=1, 2, 3, 4, or 5) and include an indenoindene core, and thus, the condensed-cyclic compound of Formula 1 may have a high electron transporting ability.

Therefore, an organic light-emitting diode including the condensed-cyclic compound of Formula 1 may have a low driving voltage, a high efficiency, a high brightness, and a long lifetime.

The condensed-cyclic compound of Formula 1 may be synthesized using a known organic synthesis method. The synthesis method of the condensed-cyclic compound of Formula 1 may be easily understood by one of ordinary skill in the art with reference to Examples, which will be described later.

The condensed-cyclic compound of Formula 1 may be used between a pair of electrodes of an organic light-emitting diode (OLED). For example, the condensed-cyclic compound of Formula 1 may be used in an emission layer (EML) and/or in a layer between an EML and a cathode (e.g., an electron transport layer (ETL), an electron injection layer (EIL), or the like).

According to another embodiment, there is provided an OLED including a first electrode, a second electrode facing the first electrode, and an organic layer interposed between the first electrode and the second electrode, wherein the organic layer includes at least one of the condensed-cyclic compounds of Formula 1 described above.

The expression "the organic layer may include at least one of the condensed-cyclic compounds of Formula 1" as used herein means that the organic layer includes one of the condensed-cyclic compounds of Formula 1 or at least two different compounds selected from the condensed-cyclic compounds of Formula 1.

For example, the organic layer may include only Compound 6 above as the condensed-cyclic compound of Formula 1. In this regard, Compound 6 may be included in an ETL of the OLED. Alternatively, the organic layer may include Compounds 6 and 15 as the condensed-cyclic compound of Formula 1. In this regard, Compounds 6 and 15 may be included in the same layer (e.g., in an ETL) or in different layers (e.g., Compound 6 may be included in an ETL and Compound 15 may be included in an EML).

The organic layer may include at least one of a hole injection layer (HIL), a hole transport layer (HTL), a functional layer having hole injection and hole transport abilities (hereinafter, referred to as "H-functional layer"), a buffer layer, an electron blocking layer (EBL), an EML, a hole blocking layer (HBL), an ETL, an electron injection layer (EIL), and a functional layer having electron transport and electron injection abilities (hereinafter, referred to as "E-functional layer").

The term "organic layer" used herein refers to a single layer or multiple layers interposed between the first electrode and the second electrode.

The organic layer may include an ETL, and the condensed-cyclic compound of Formula 1 may be included in the ETL.

The ETL may further include a metal-containing material, in addition to the condensed-cyclic compound of Formula 1.

FIG. 1 is a schematic cross-sectional view of an OLED 10 according to an embodiment. Hereinafter, structure and manufacturing method of an OLED will be described in more detail with reference to FIG. 1.

A substrate 11 may be a substrate used in a general OLED, and may be a glass substrate or a transparent plastic substrate having excellent mechanical strength, thermal stability, transparency, surface smoothness, ease of handling, and waterproofness.

A first electrode 13 may be formed by applying a first electrode material on the substrate 11 by deposition or sputtering. When the first electrode 13 is an anode, the first electrode material may be selected from materials having a high work function so as to facilitate hole injection. The first electrode 13 may be a reflective electrode or a transparent electrode. Examples of the first electrode material may include indium-tin oxide (ITO), Indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 13 may be formed as a reflective electrode.

The first electrode 13 may be formed as a single layer or have a multi-layered structure having at least two layers. For example, the first electrode 13 may have a three-layered structure, e.g., ITO/Ag/ITO, but is not limited thereto.

An organic layer 15 is formed on the first electrode 13.

The organic layer 15 may include a HIL, a HTL, a buffer layer, an EML, an ETL, and an EIL.

The HIL may be formed on the first electrode 13 by using various methods such as vacuum deposition, spin coating, casting, or LB deposition.

When the HIL is formed by vacuum deposition, the deposition conditions may vary according to a compound used as a material for forming the HIL, a structure of a desired HIL, and thermal characteristics. For example, the deposition condition may be, but is not limited to, a deposition temperature of about 100° C. to about 500° C., a degree of vacuum of about $10^{-8}$ torr to about $10^{-3}$ torr, and a deposition speed of about 0.01 to about 100 Å/sec.

When the HIL is formed by spin coating, the coating condition may vary according to a compound used as a material for forming the HIL, a structure of a desired HIL, and thermal characteristics. For example, the coating condition may be, but is not limited to, a coating speed of about 2,000 rpm to about 5,000 rpm and a heat treatment temperature for removing a solvent after coating of about 80° C. to about 200° C.

The material for forming the HIL may be a known hole injection material. Examples of the known hole injection material include, but are limited to, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino) triphenylamine (m-MTDATA), N,N'-di(1-naphthyl)-N,N'-diphenylbenzidine (NPB), TDATA, 2-TNATA, polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline/poly(4-styrenesulfonate) (PANI/PSS):

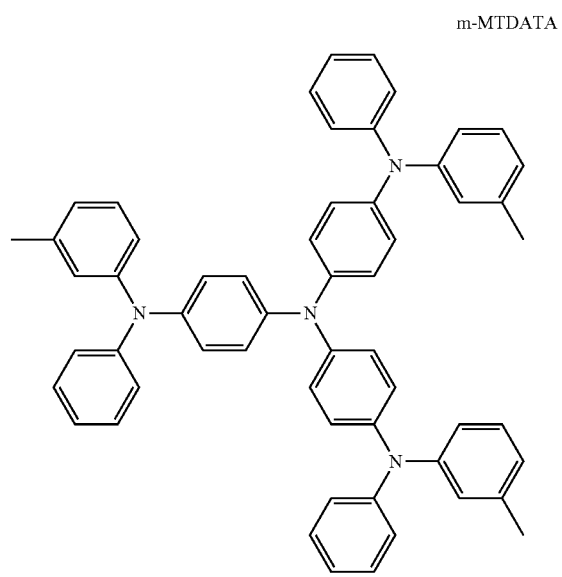

m-MTDATA

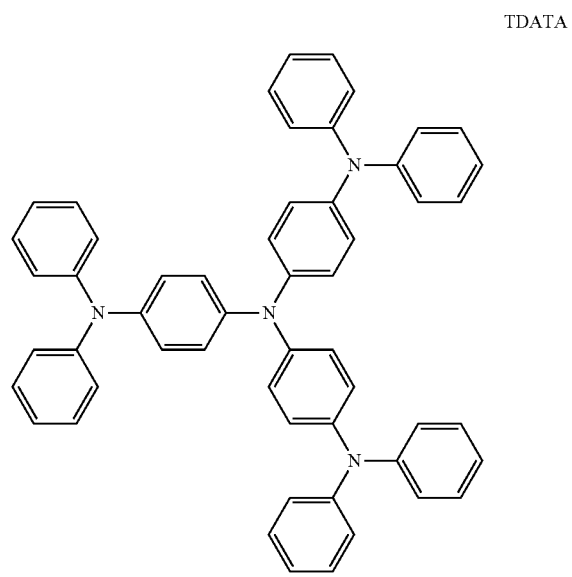

TDATA

2-TNATA

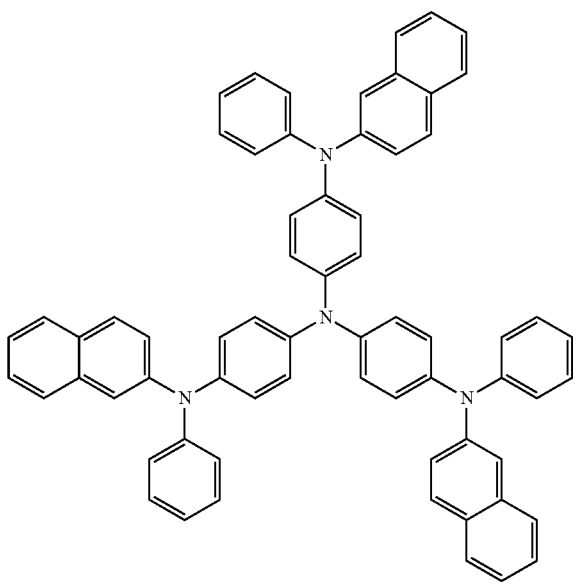

The thickness of the HIL may be in the range of about 100 Å to about 10,000 Å. In some embodiments, the thickness of the HIL may be in the range of about 100 Å to about 1,000 Å. When the thickness of the HIL is within these ranges, satisfactory hole injection properties may be obtained without a substantial increase in driving voltage.

An HTL may be formed on the HIL by using various methods such as vacuum deposition, spin coating, casting, or LB deposition. When the HTL is formed by vacuum deposition or spin coating, the deposition and coating conditions may vary according to a used compound. However, in general, the deposition and coating conditions may be almost the same as the condition for forming the HIL.

A known hole transporting material may be, for example, carbazole derivatives such as N-phenylcarbazole and polyvinylcarbazole, N,N-bis(3-methylphenyl)-N,N-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB), but is not limited thereto.

TPD

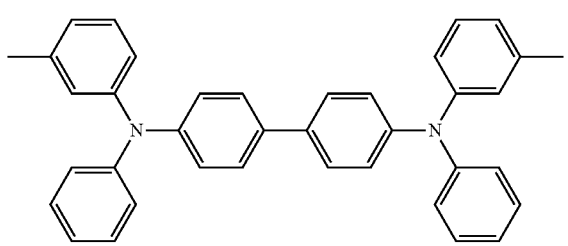

NPB

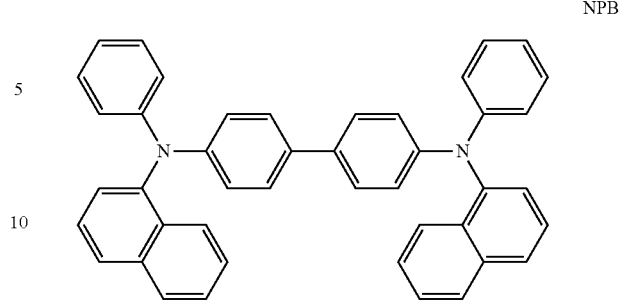

The thickness of the HTL may be in the range of about 50 Å to about 2,000 Å. In some embodiments, the thickness of the HTL may be in the range of about 100 Å to about 1,500 Å. When the thickness of the HTL is within these ranges, satisfactory hole transport properties may be obtained without a substantial increase in driving voltage.

At least one of the hole injection material and the hole transporting material as described above may be included in the H-functional layer. The thickness of the H-funcational layer may be in the range of about 500 Å to about 10,000 Å. In some embodiments, the thickness of the H-funcational layer may be in the range of about 100 Å to about 1,000 Å. When the thickness of the H-functional layer is within these ranges, satisfactory hole injection and hole transport properties may be obtained without a substantial increase in driving voltage.

At least one of the HIL, the HTL, and the H-functional layer may include at least one of compounds represented by Formulae 300 and 350 below:

Formula 300

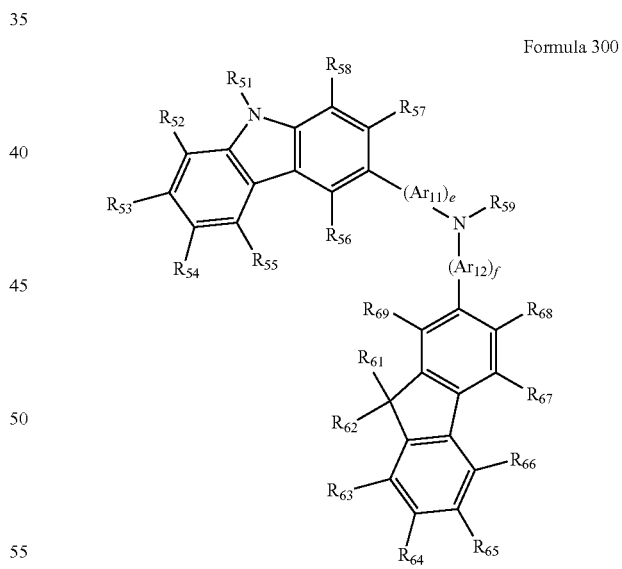

Formula 350

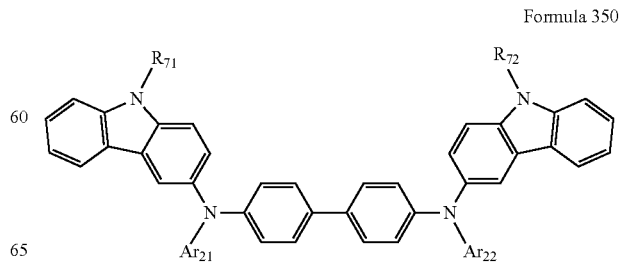

In Formulae 300 and 350, $Ar_{11}$ and $Ar_{12}$ may be each independently a substituted or unsubstituted $C_6$-$C_{60}$ arylene group and $Ar_{21}$ and $Ar_{22}$ may be each independently a substituted or unsubstituted $C_6$-$C_{60}$ aryl group. A detailed description of $Ar_{11}$ and $Ar_{12}$ may be found in the detailed description of $L_1$ above and a detailed description of $Ar_{21}$ and $Ar_{22}$ may be found in the detailed description of $R_5$ above.

In Formula 300 above, e and f may be each independently an integer of 0 to 5. In some embodiments, e and f may be each independently 0, 1, or 2. For example, e may be 1 and f may be 0, however, e and f are not limited to the above example.

In Formulae 300 and 350 above, $R_{51}$ through $R_{58}$, $R_{61}$ through $R_{69}$, and $R_{71}$ and $R_{72}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. For example, $R_{51}$ through $R_{58}$, $R_{61}$ through $R_{69}$, and $R_{71}$ and $R_{72}$ may be each independently one of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group (e.g., methyl, ethyl, propyl, butyl, pentyl, hexyl, and the like), a $C_1$-$C_{10}$ alkoxy group (e.g., methoxy, ethoxy, propoxy, butoxy, pentoxy, and the like); a $C_1$-$C_{10}$ alkyl group and a $C_1$-$C_{10}$ alkoxy group that is substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that is substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group, but are not limited thereto.

In Formula 300 above, $R_{59}$ may be one of a phenyl group; a naphthyl group; an anthryl group; a biphenyl group; a pyridinyl group; and a phenyl group, a naphthyl group, an anthryl group, a biphenyl group, and a pyridinyl group that is substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment, the compound of Formula 300 may be represented by Formula 300A below, but is not limited thereto:

Formula 300A

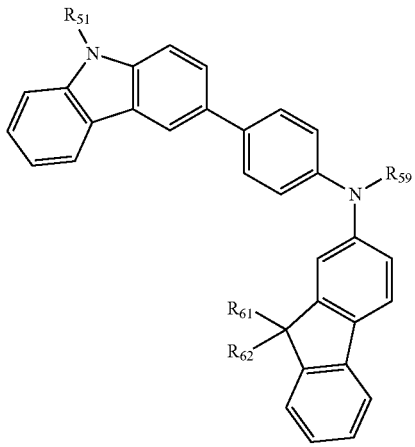

In Formula 300A, a detailed description of $R_{51}$, $R_{60}$, $R_{61}$, and $R_{59}$ may be the same as already provided above.

For example, at least one of the HIL, the HTL, and the H-functional layer may include at least one of Compounds 301 through 320 below, but is not limited thereto:

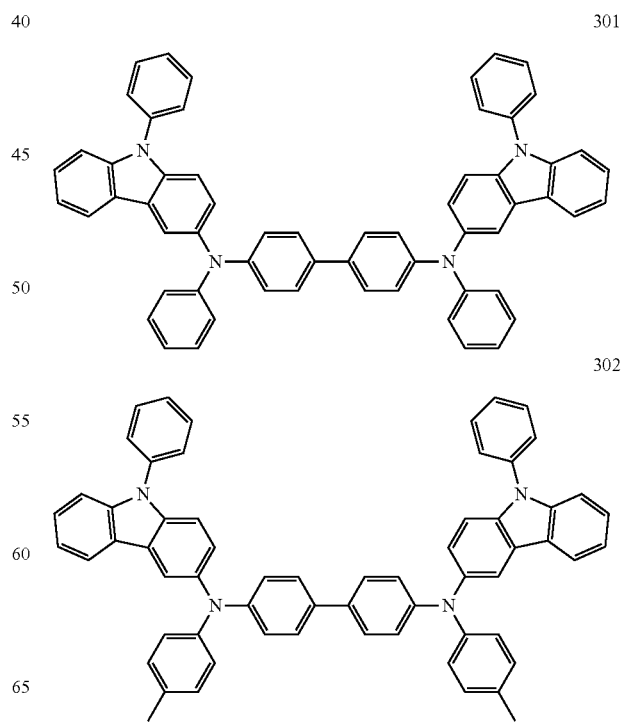

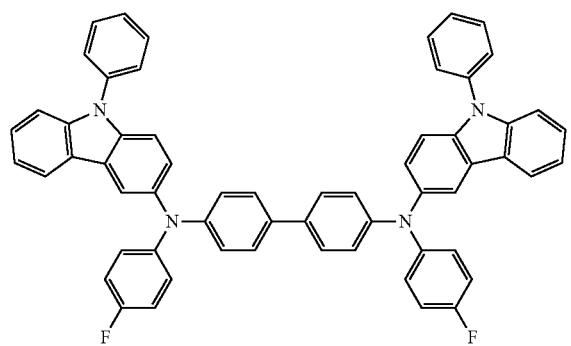
303
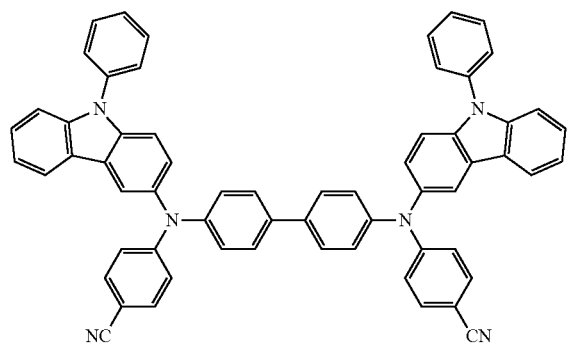
304
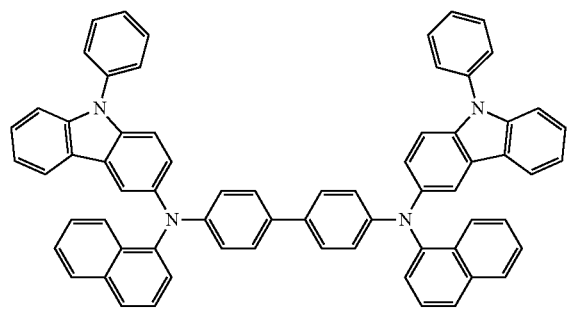
305
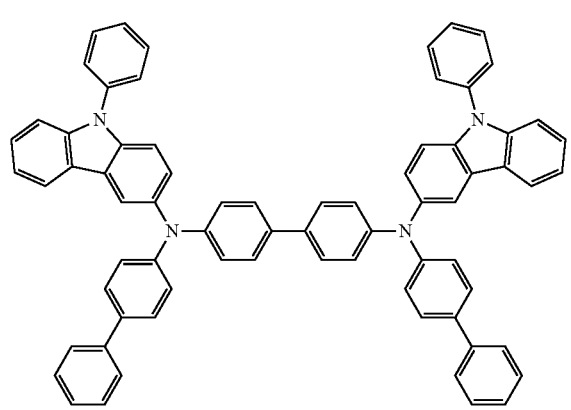
306
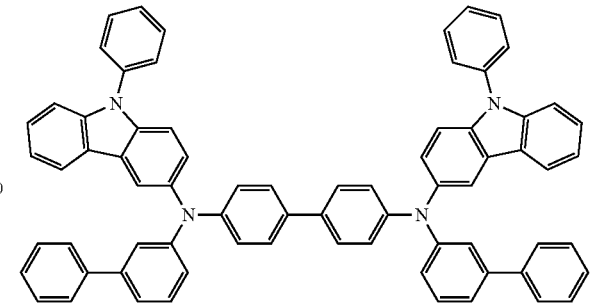
307
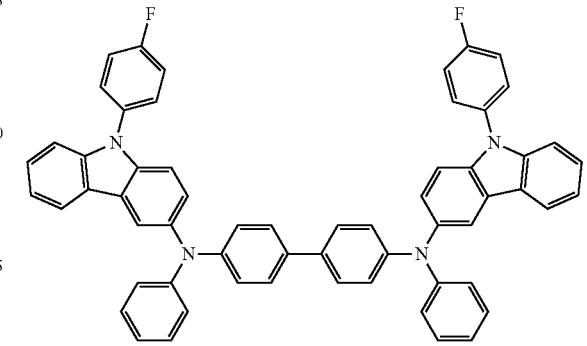
308
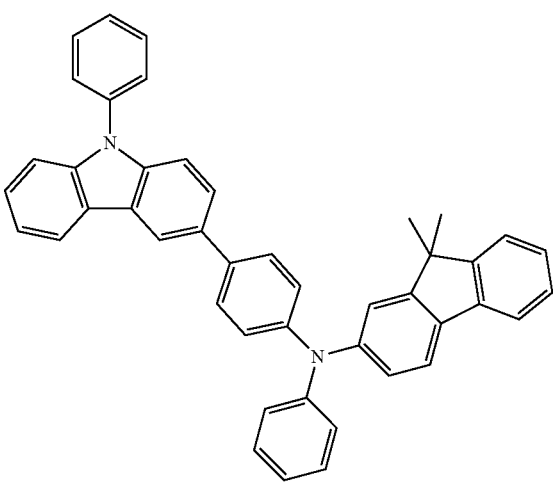
309

310
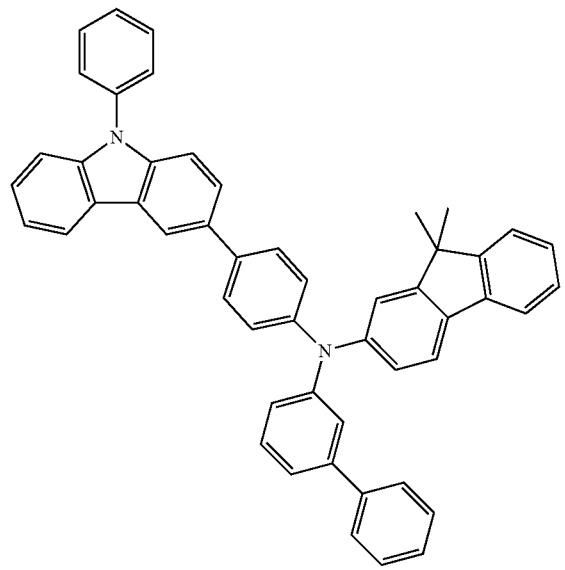
311
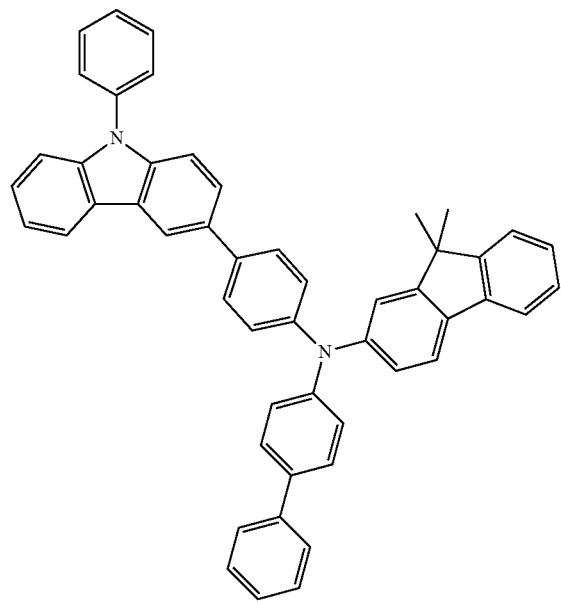
312
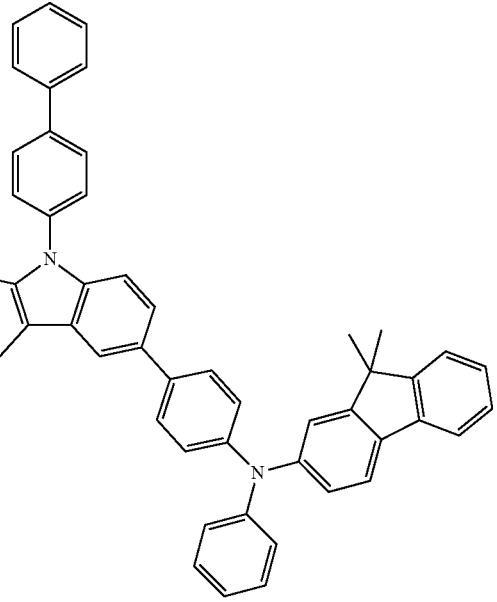
313
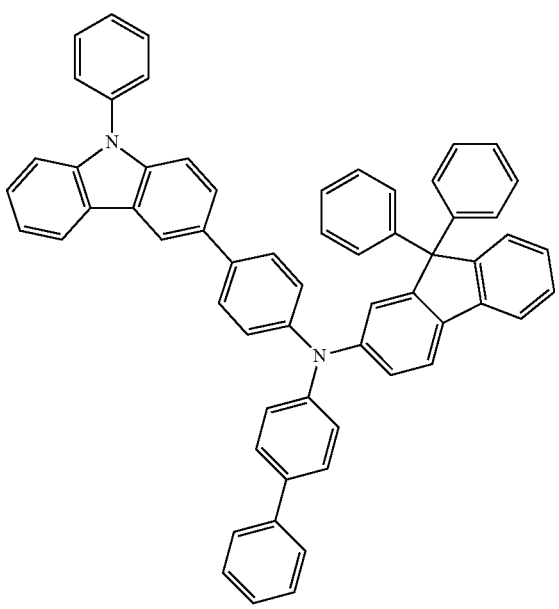

314
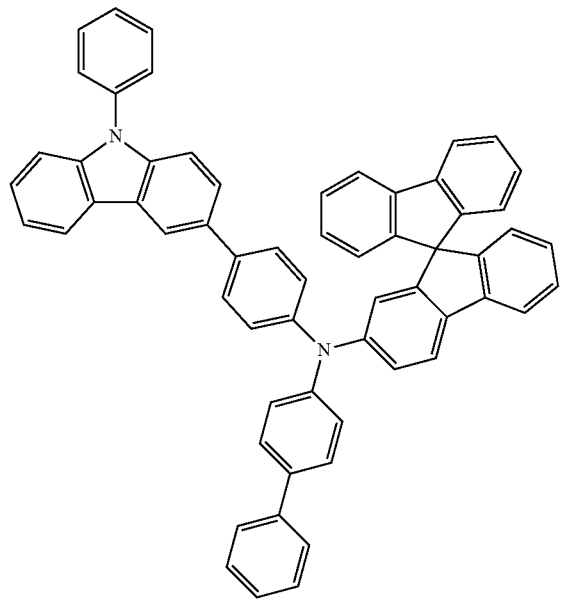
315
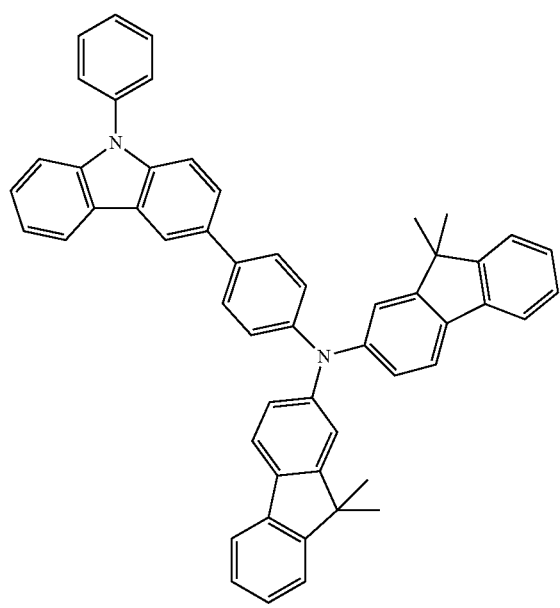
316
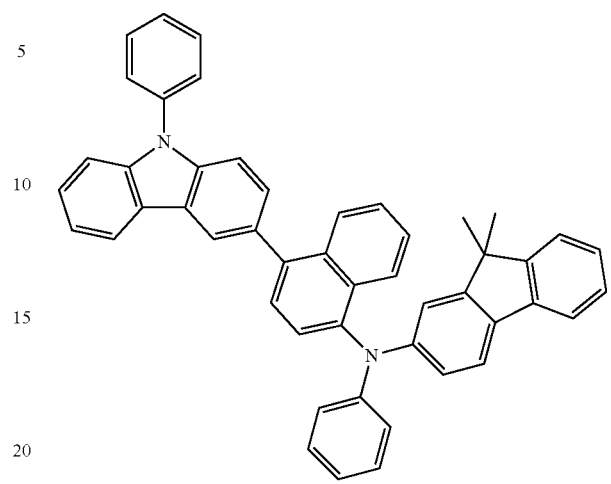
317
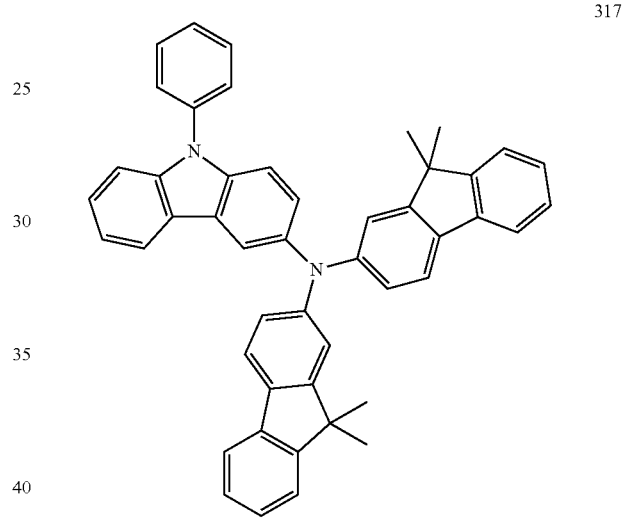
318
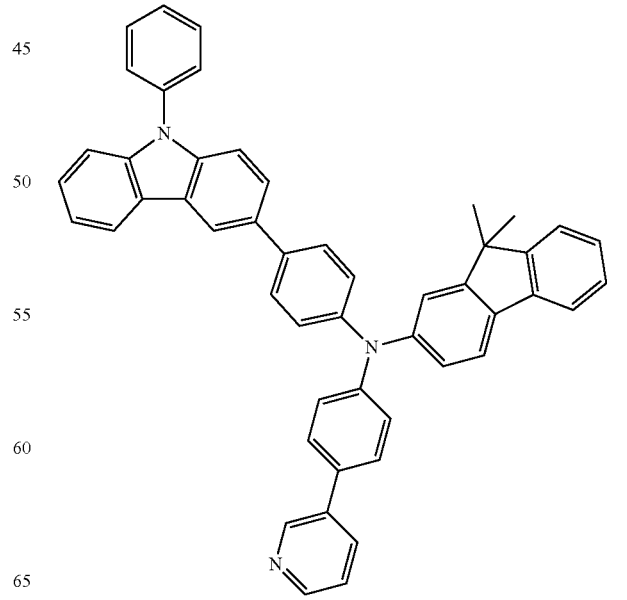

-continued

319

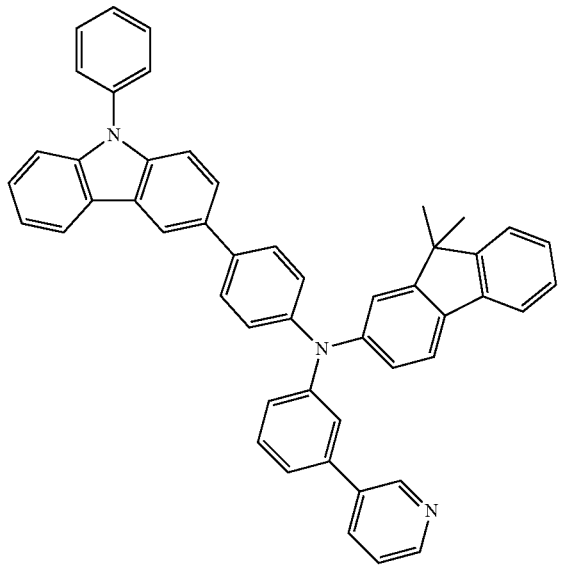

320

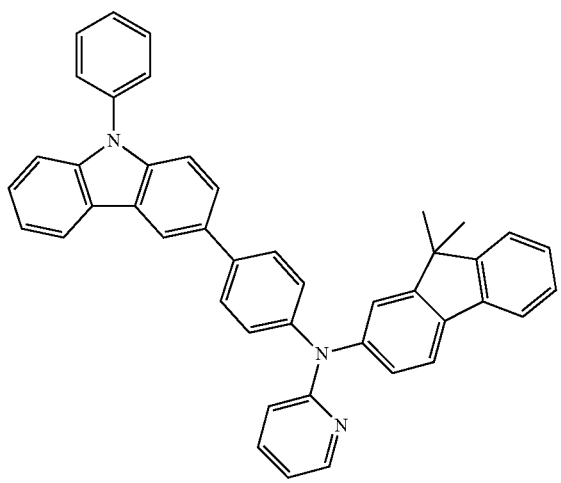

At least one of the HIL, the HTL, and the H-functional layer may further include a charge-generating material so as to increase the conductivity of the layers, in addition to the known hole injection material, the known hole transporting material and/or the material for forming the H-functional layer having hole injection and hole transport abilities.

The charge-generating material may be, for example, a p-dopant. The p-dopant may be one of a quinone derivative, a metal oxide, and a cyano-containing compound, but is not limited thereto. Examples of the p-dopant may include, but are not limited to, quinone derivatives such as tetra-cyano-quinodimethane (TCNQ) and 2,3,5,6-tetrafluoro-tetra-cyano-1,4-benzoquinodimethane (F4-TCNQ); metal oxides such as an tungsten oxide and a molybdenum oxide; and cyano-containing compounds such as Compound 200 below and the like.

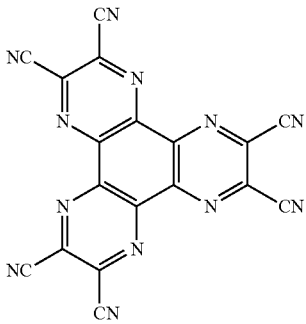

Compound 200

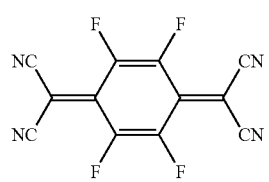

F4-TCNQ

When the HIL, the HTL, or the H-functional layer further includes the charge-generating material, the charge-generating material may be homogeneously or inhomogeneously dispersed in the HIL, the HTL, or the H-functional layer.

A buffer layer may be interposed between the EML and at least one of the HIL, the HTL, and the H-functional layer. The buffer layer increases efficiency by compensating for an optical resonance distance according to the wavelength of light emitted from the EML. The buffer layer may include a known hole injection material and a known hole transporting material. Also, the buffer layer may include the same material as one of the materials included in the HIL, the HTL, and the H-functional layer.

An EML may be formed on the HTL, the H-functional layer, or the buffer layer by vacuum deposition, spin coating, casting, or LB deposition. When the EML is formed by vacuum deposition or spin coating, the deposition and coating conditions may vary according to a used compound. However, in general, the deposition and coating conditions may be almost the same as the condition for forming the HIL.

The EML may include a host and a dopant.

Examples of the host may include, but are not limited to, Tris(8-hydroxyquinolinato)aluminium (Alq3), 4,4'-N,N'-di-cabazole-biphenyl (CBP), poly(n-vinylcabazole) (PVK), 9,10-di(naphthalene-2-yl)anthracene (ADN), 4,4',4''-tris(N-carbazolyl)-triphenylamine (TCTA), 1,3,5-tris(N-phenyl-benzimidazole-2-yl)benzene (TPBI), 3-tert-butyl-9,10-di (naphth-2-yl) anthracene (TBADN), E3, and distyrylarylene (DSA), dmCBP (see Formula below), and Compounds 501 through 509 below.

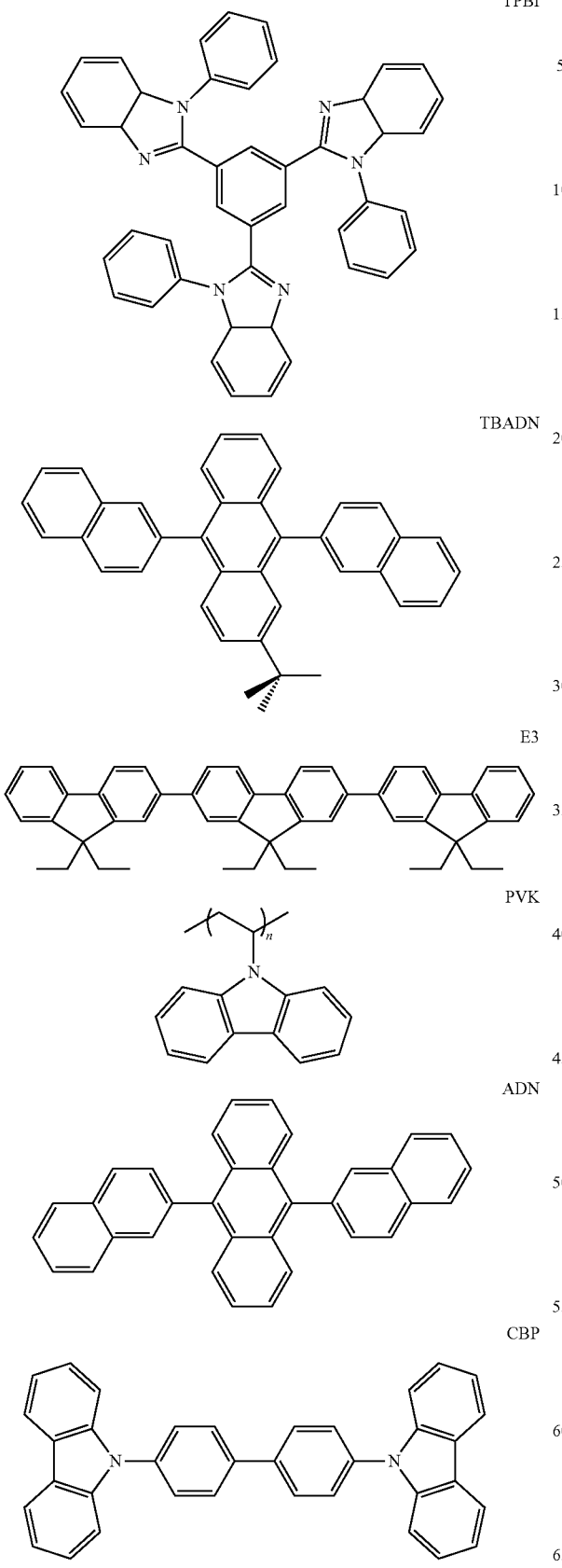
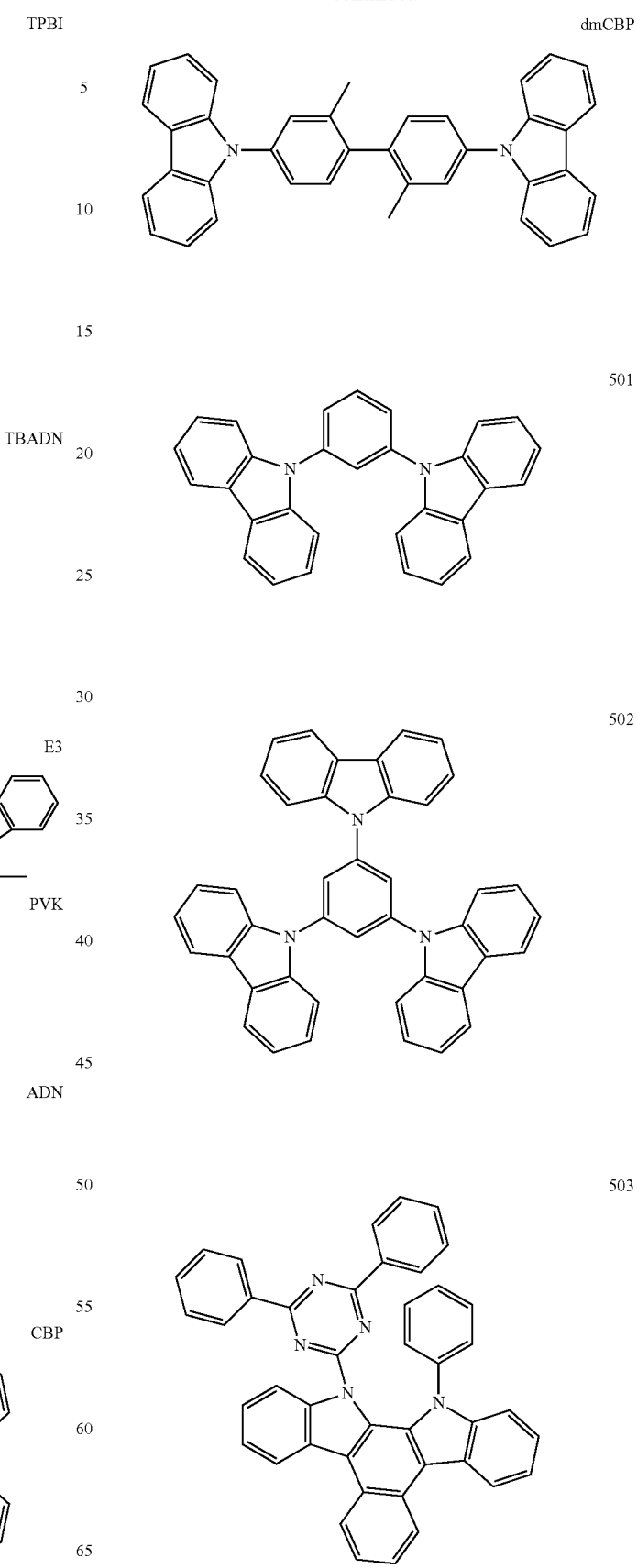

504

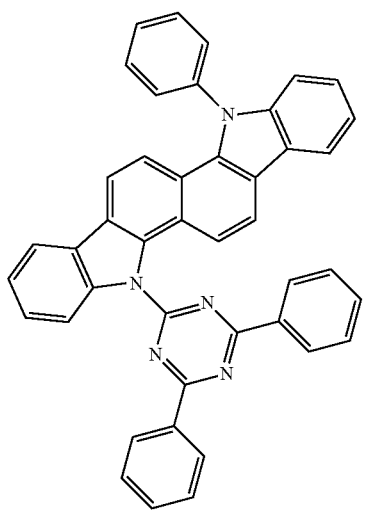

505

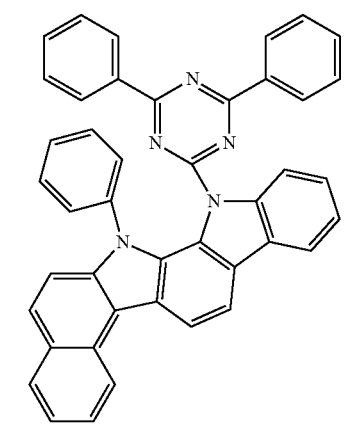

506

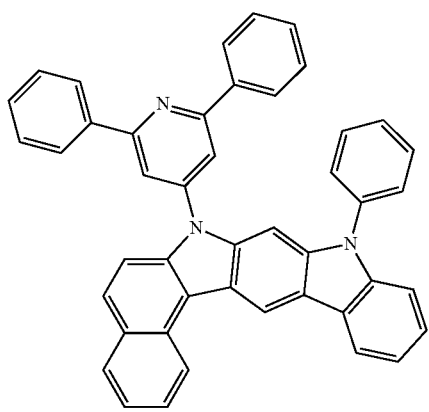

507

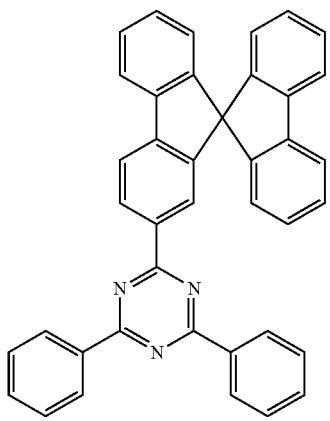

508

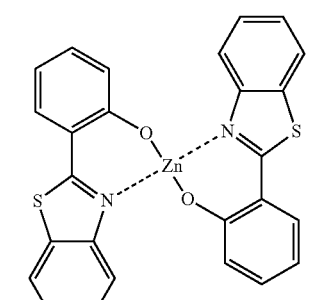

509

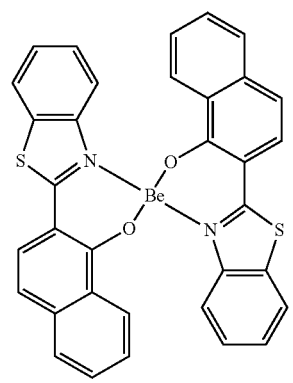

Also, the host may be an anthracene-based compound represented by Formula 400 below:

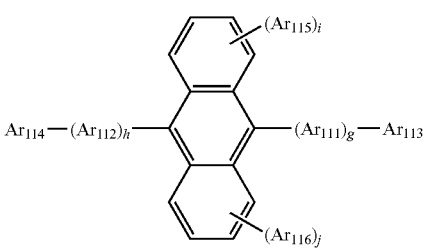

Formula 400

In Formula 400, $Ar_{111}$ and $Ar_{112}$ may be each independently a substituted or unsubstituted $C_6$-$C_{60}$ arylene group; $Ar_{113}$ through $Ar_{116}$ may be each independently a substituted or unsubstituted $C_1$-$C_{10}$ alkyl group or a substituted or unsubstituted $C_6$-$C_{60}$ aryl group; and g, h, i, and j may be each independently an integer of 0 to 4.

For example, in Formula 400 above, $Ar_{111}$ and $Ar_{112}$ may be each independently a phenylene group; a naphthylene group; a phenanthrenylene group; a pyrenylene group; or a phenylene group, a naphthylene group, a phenanthrenylene group, a fluorenyl group, or a pyrenylene group that is substituted with at least one of a phenyl group, a naphthyl group, and an anthryl group, but are not limited thereto.

In Formula 400 above, g, h, i, and j may be each independently 0, 1, or 2.

In Formula 400 above, $Ar_{113}$ through $Ar_{116}$ may be each independently, but are not limited to, a $C_1$-$C_{10}$ alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that is substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

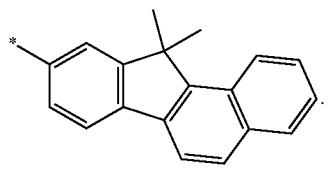 [SMILES: *c1ccc2c(c1)C(C)(C)c1c-2ccc2ccccc12]

For example, the anthracene-based compound of Formula 400 may be, but is not limited to, one of the compounds below:

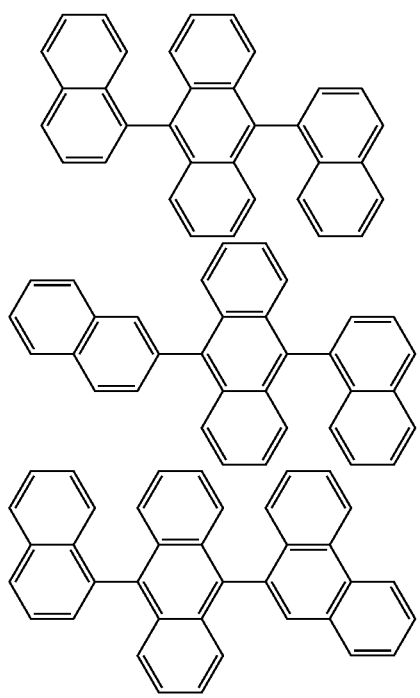

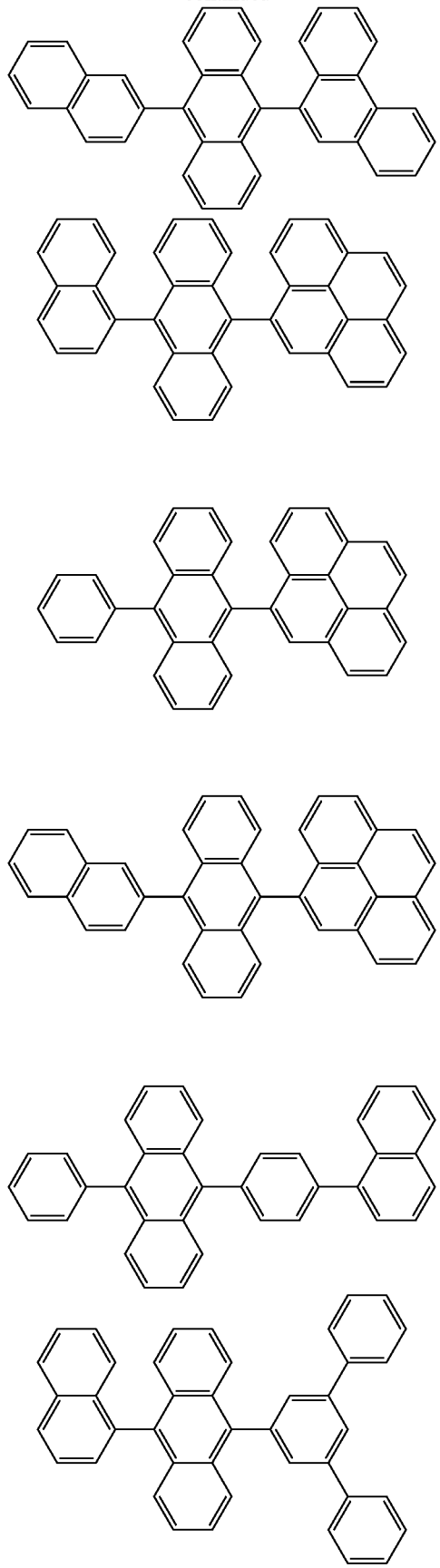

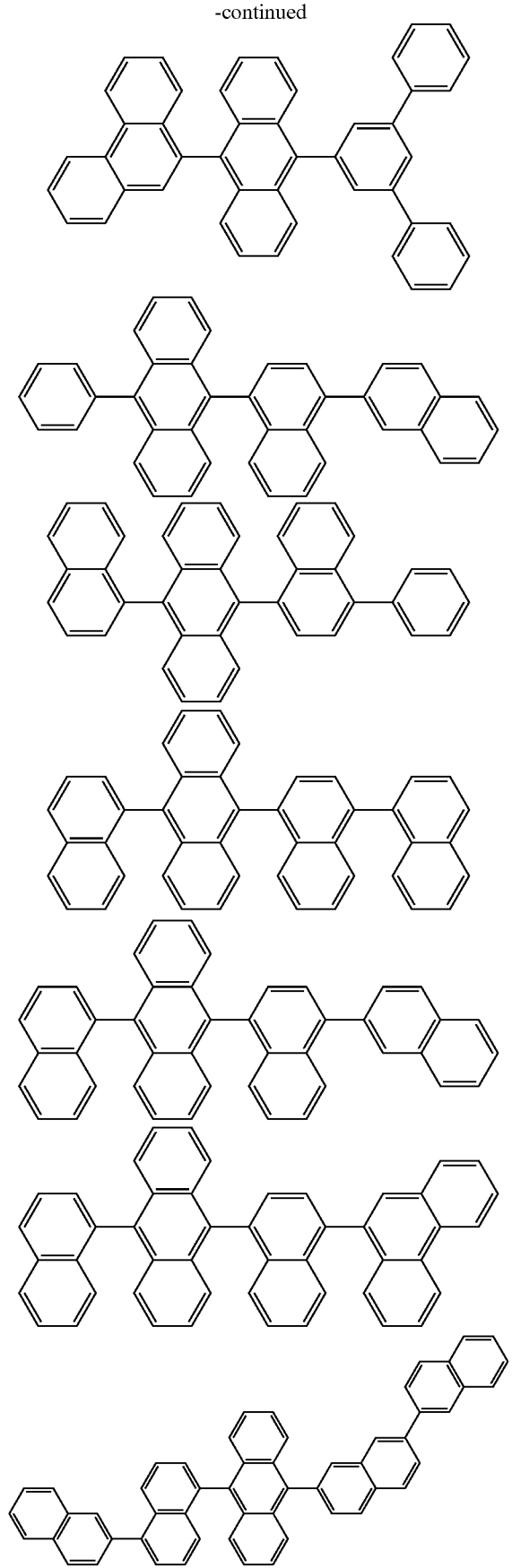
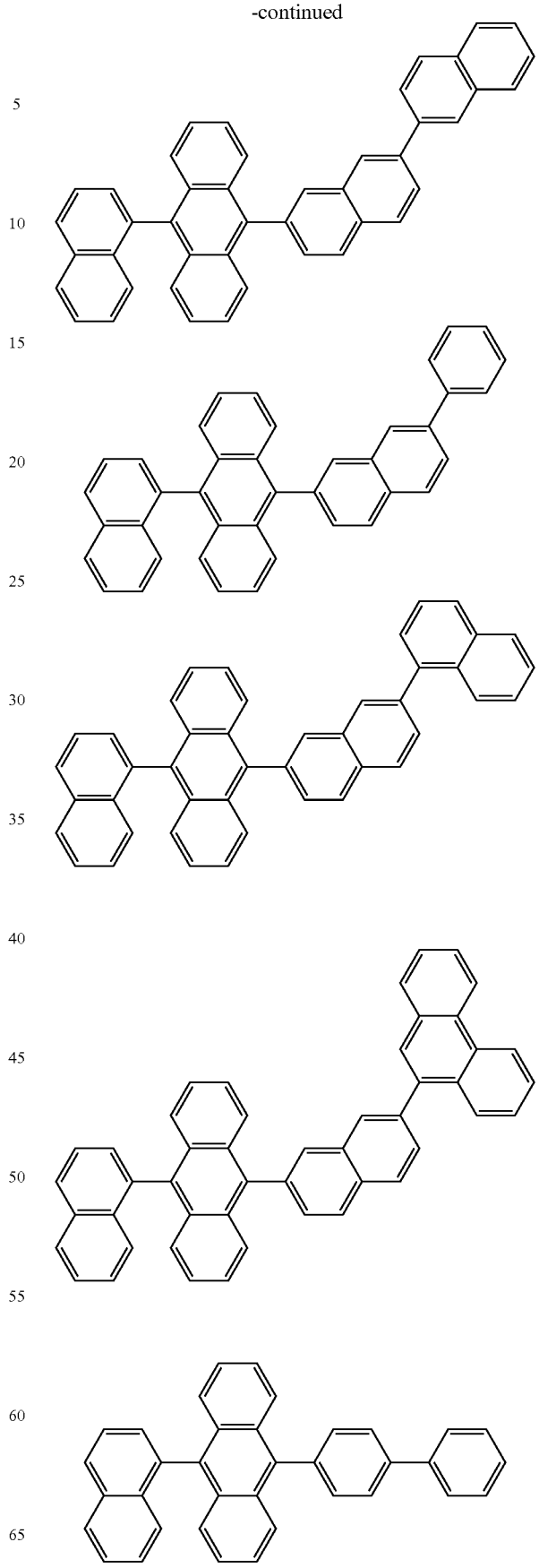

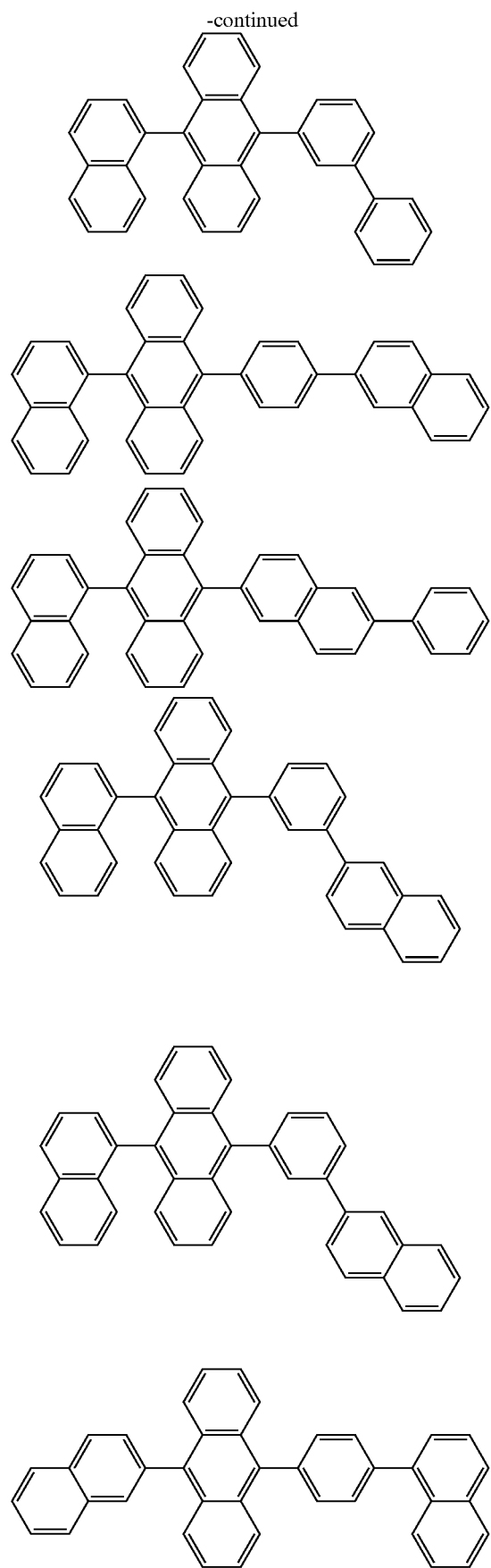

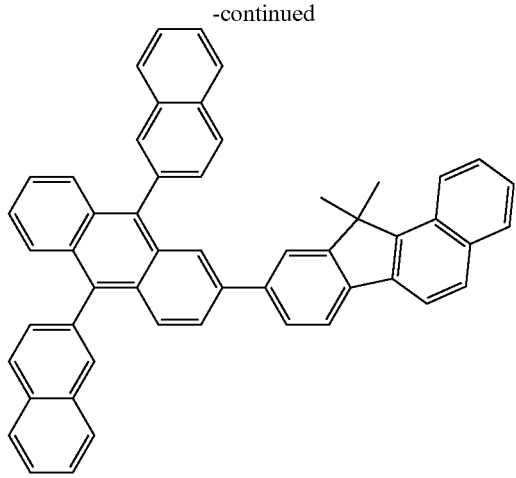

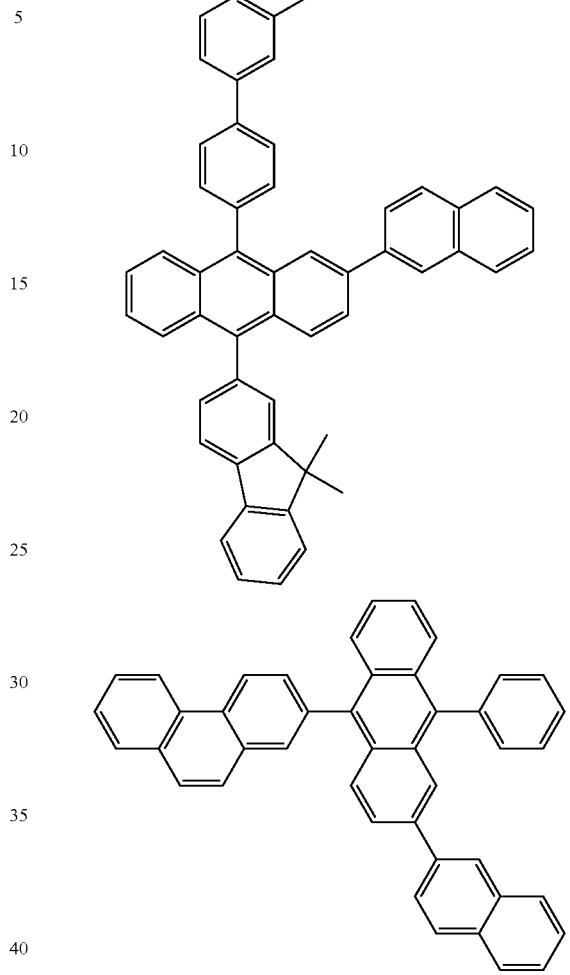

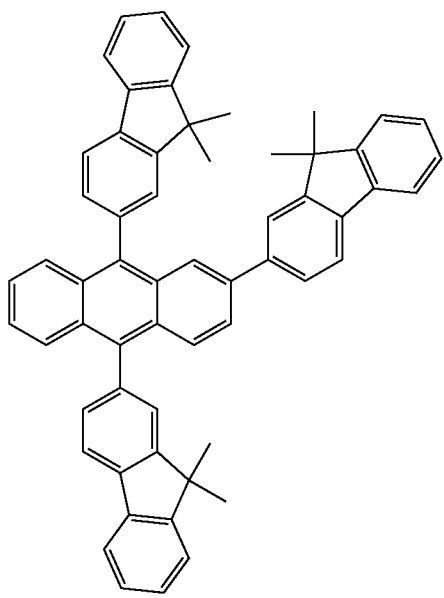

Also, an anthracene-based compound represented by Formula 401 below may be used as the host:

Formula 401

In Formula 401, a detailed description of $Ar_{122}$ through $Ar_{125}$ is provided above in the description of $Ar_{113}$ of Formula 400.

In Formula 401 above, $Ar_{126}$ and $Ar_{127}$ may be each independently a $C_1$-$C_{10}$ alkyl group (e.g., a methyl group, an ethyl group, or a propyl group).

In Formula 401 above, k and l may be each independently an integer of 0 to 4. For example, k and l may be each independently 0, 1, or 2.

For example, the anthrecene-based compound of Formula 401 may be, but is not limited to, one of the following compounds.

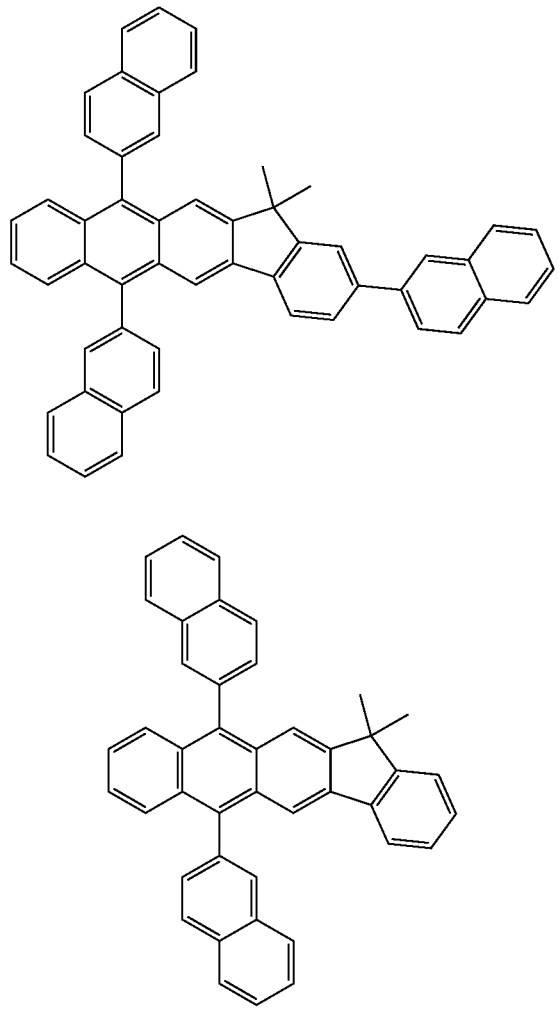

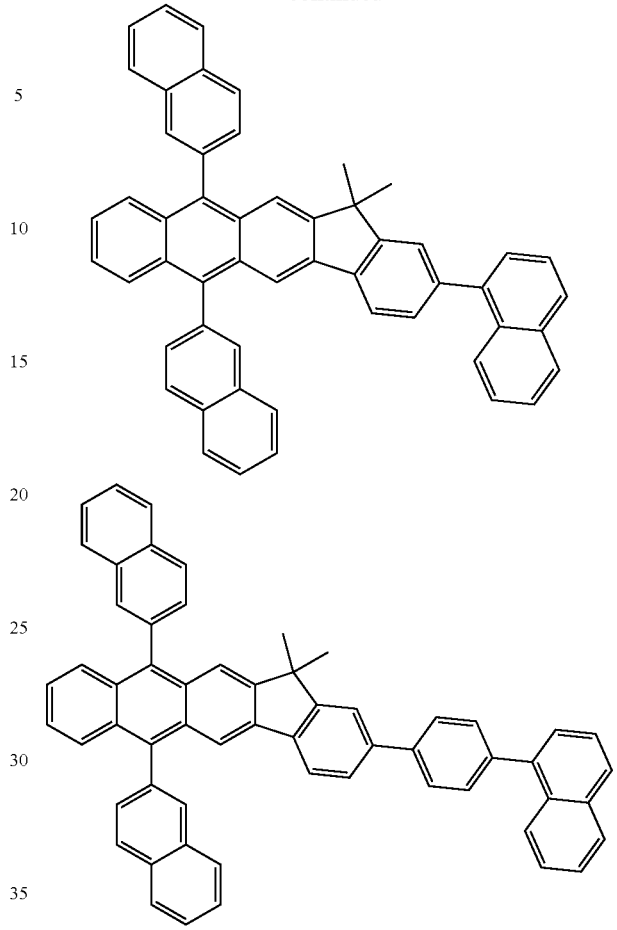

When the OLED is a full-color OLED, the EML may be patterned as a red EML, a green EML, and a blue EML.

In this regard, at least one of the red EML, the green EML, and the blue EML may include the following dopants (ppy=phenylpyridine).

For example, compounds described below may be used as blue dopants, but are not limited thereto.

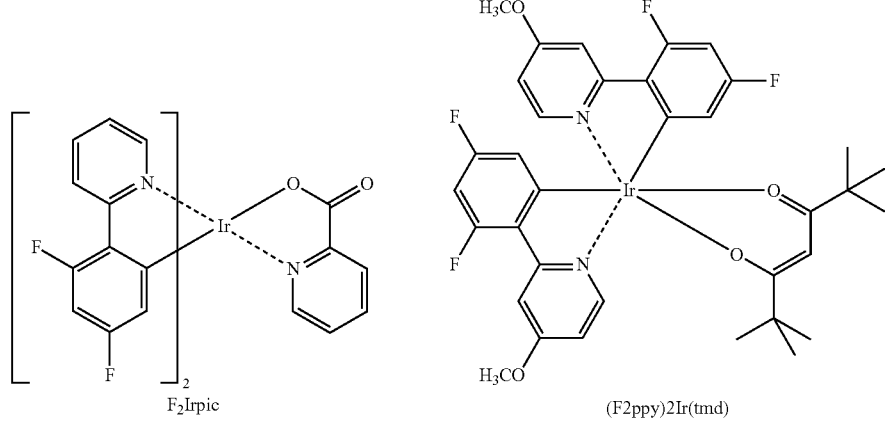

F₂Irpic      (F2ppy)2Ir(tmd)

-continued
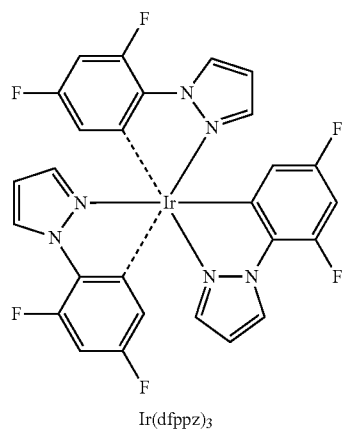
Ir(dfppz)₃
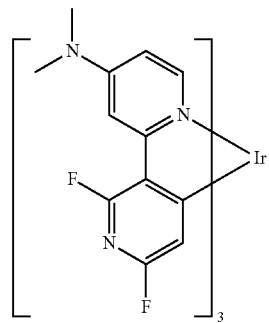
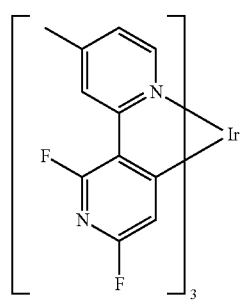
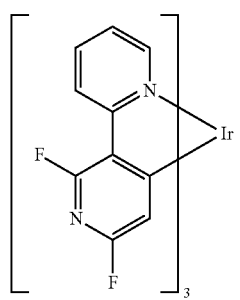
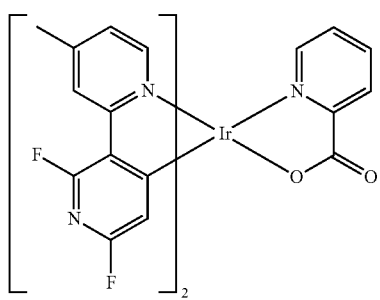
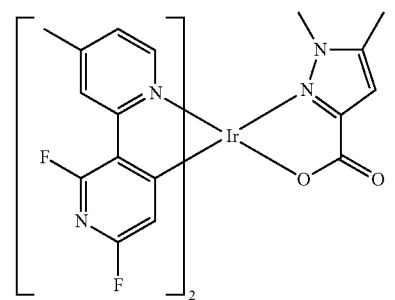
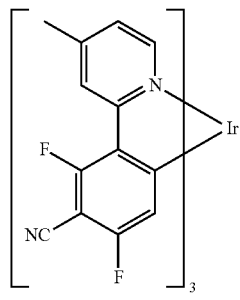
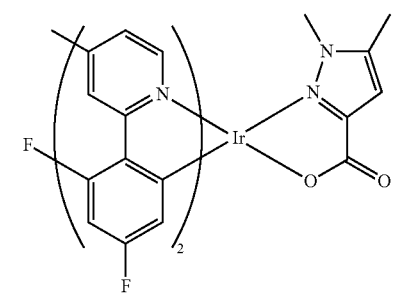
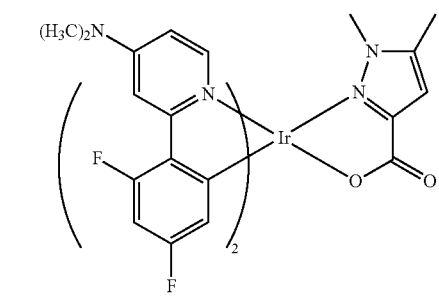
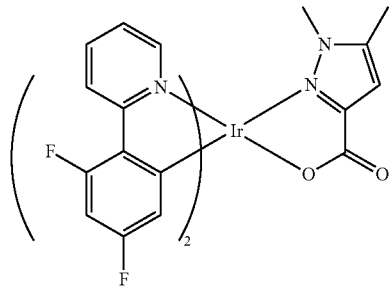
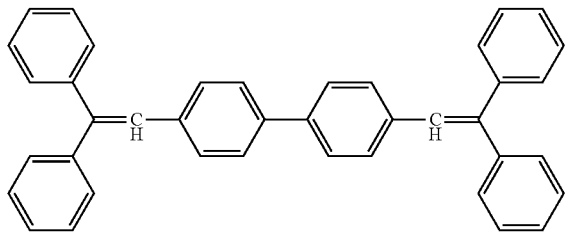
DPVBi
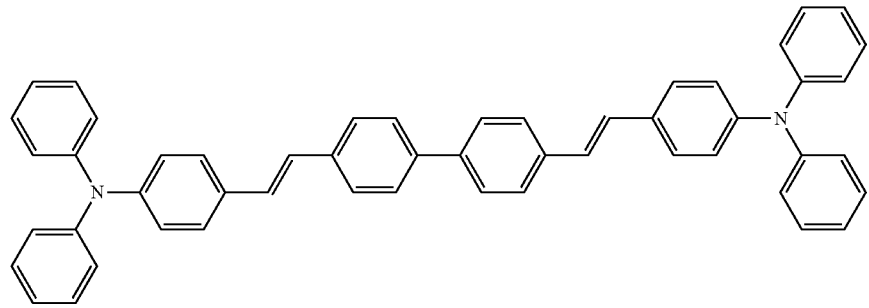
DPAVBi

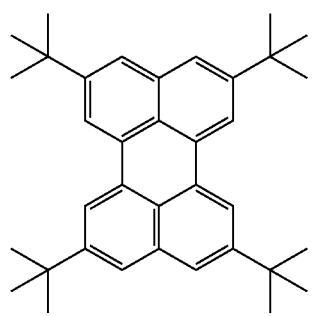
TBPe
For example, compounds described below may be used as red dopants, but are not limited thereto. Alternatively, DCM or DCJTB, which will be described below, may be used as the red dopant.
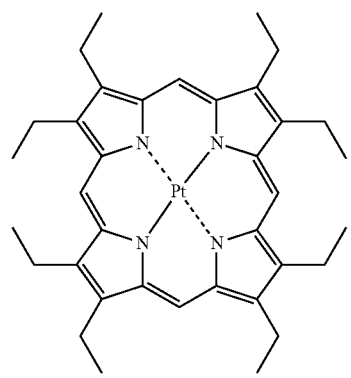
PtOEP
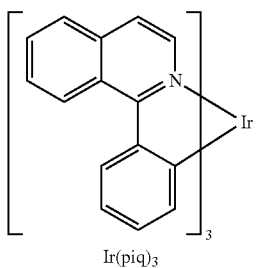
Ir(piq)₃
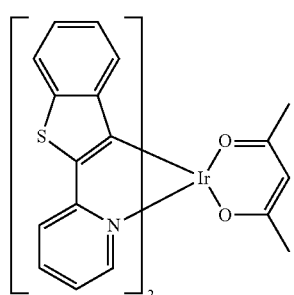
Btp₂Ir(acac)
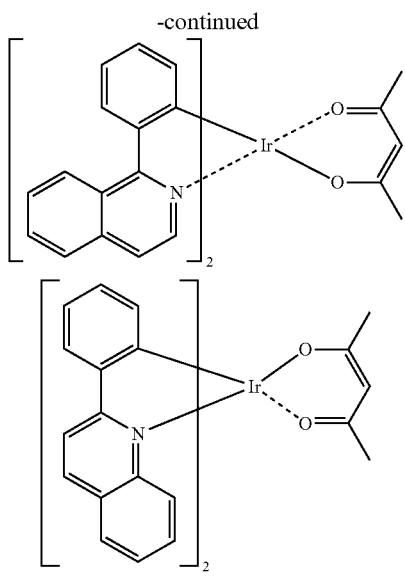
Ir(pq)₂(acac)
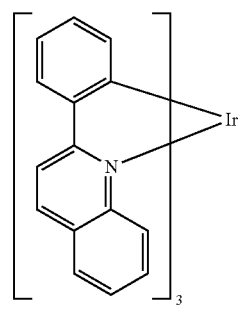
Ir(2-phq)₃
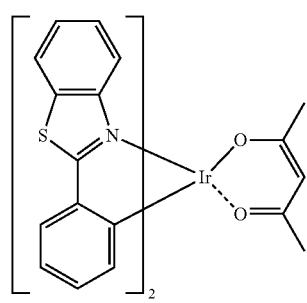
Ir(BT)₂(acac)

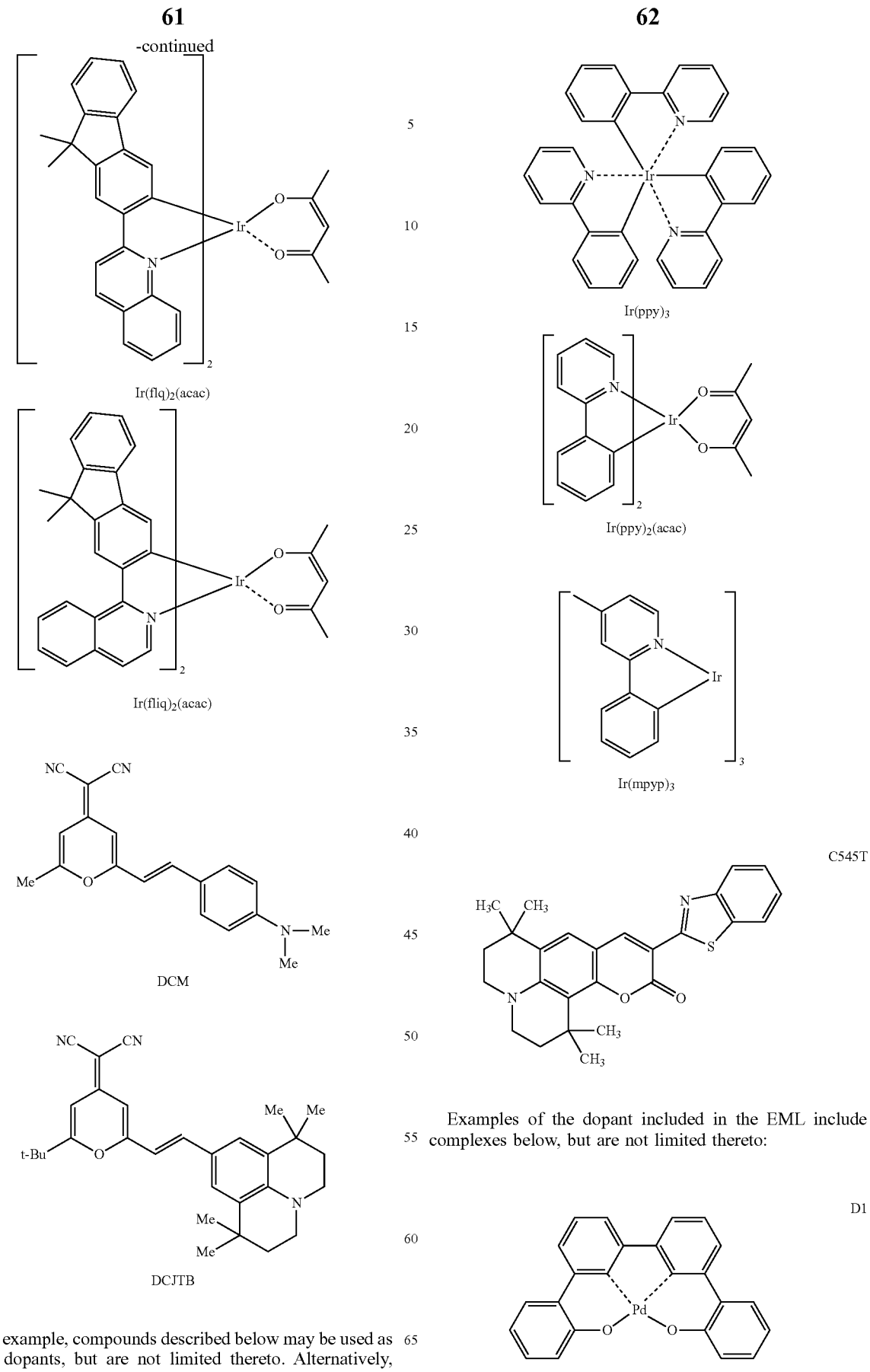
For example, compounds described below may be used as green dopants, but are not limited thereto. Alternatively, C545T below may be used as a green dopant.
Examples of the dopant included in the EML include complexes below, but are not limited thereto:

-continued
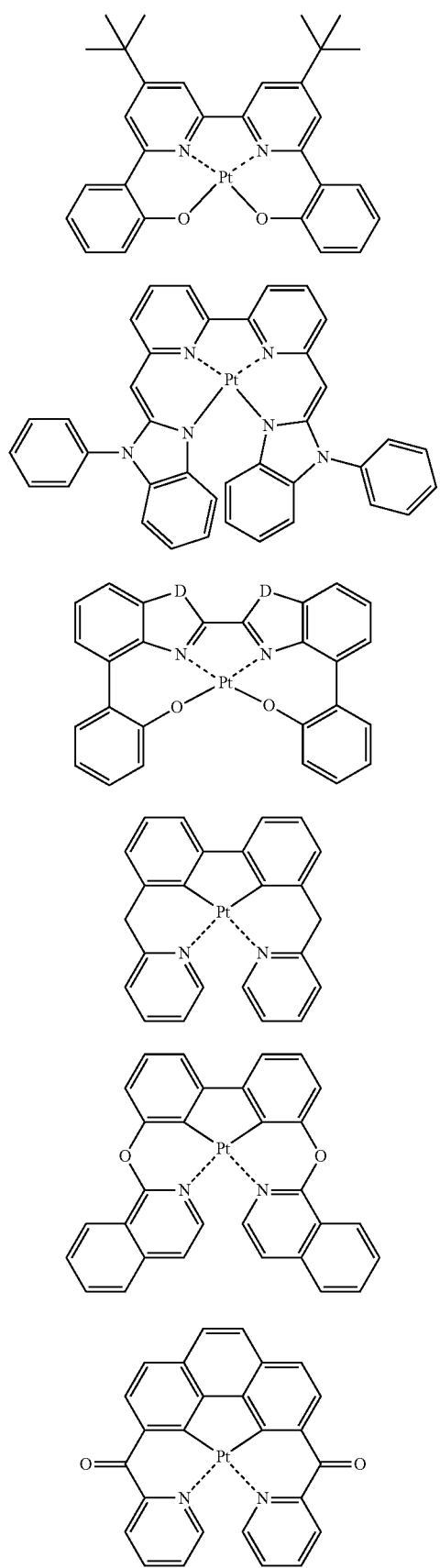
-continued
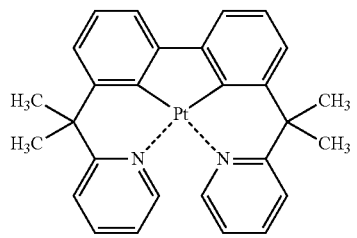
D8
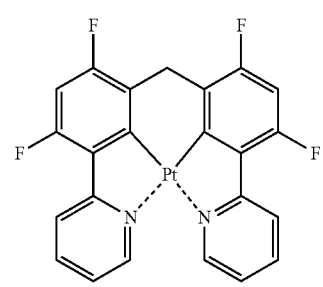
D9
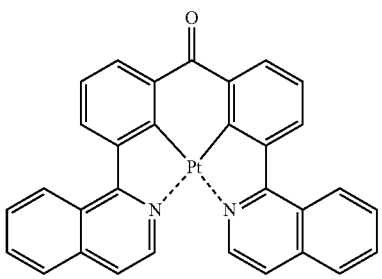
D10
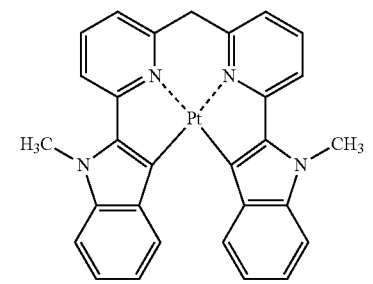
D11
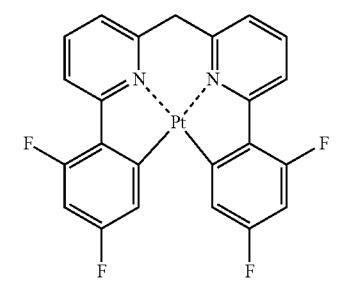
D12
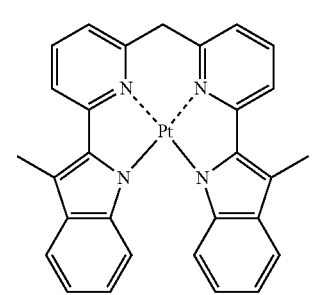
D13

D14 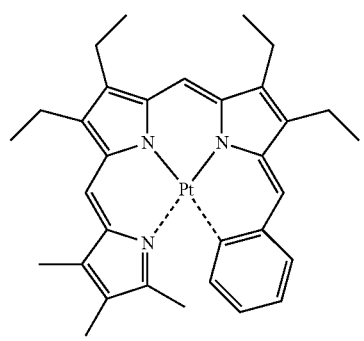
D15 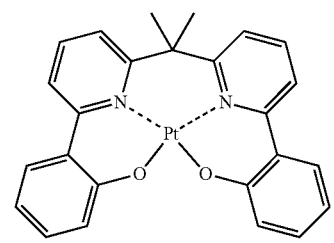
D16 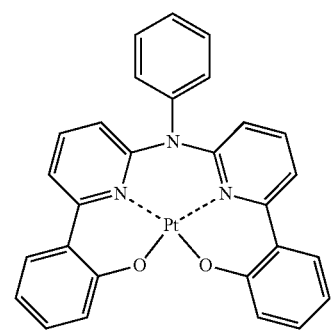
D17 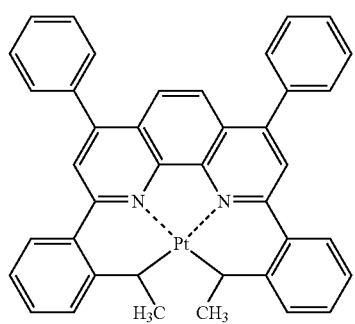
D18 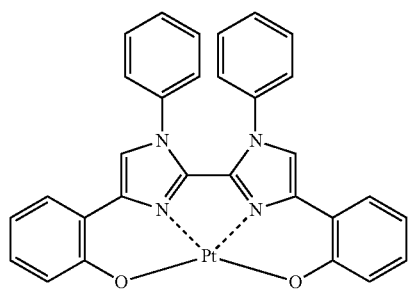
D19 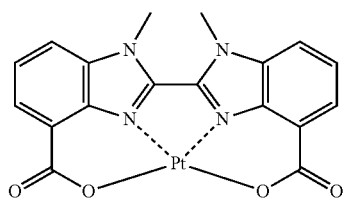
D20 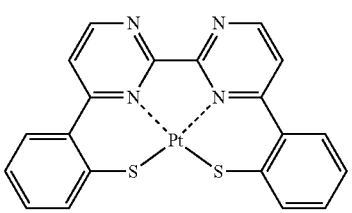
D21 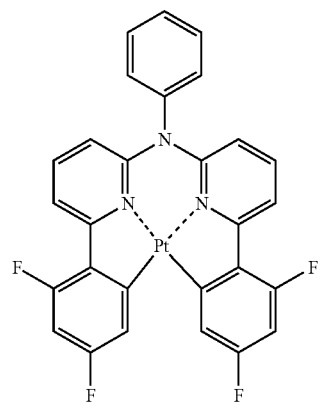
D22 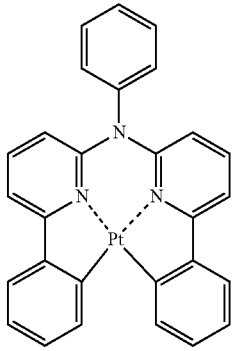
D23 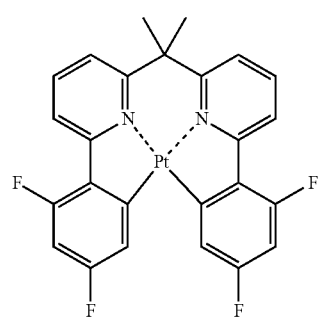

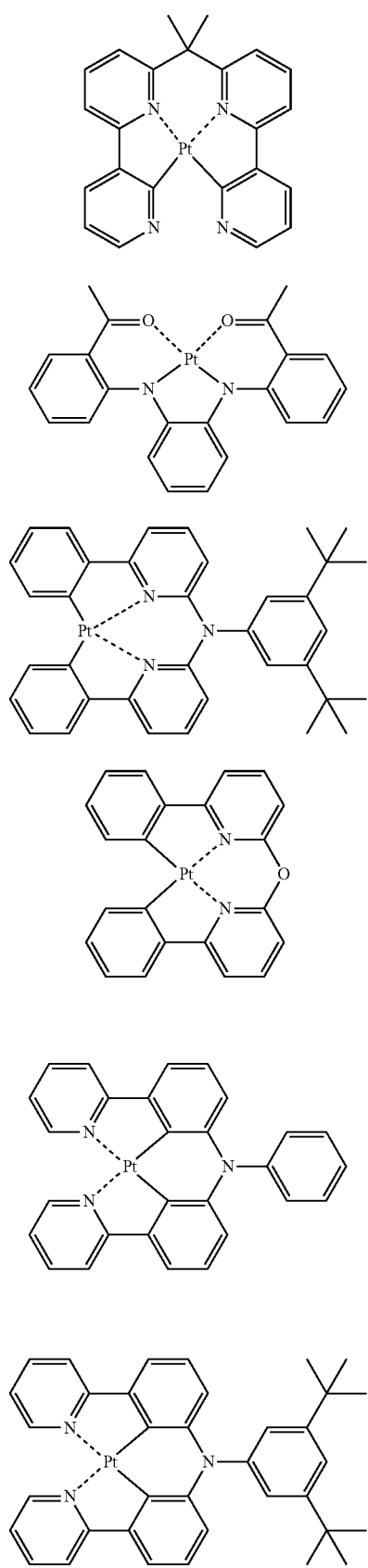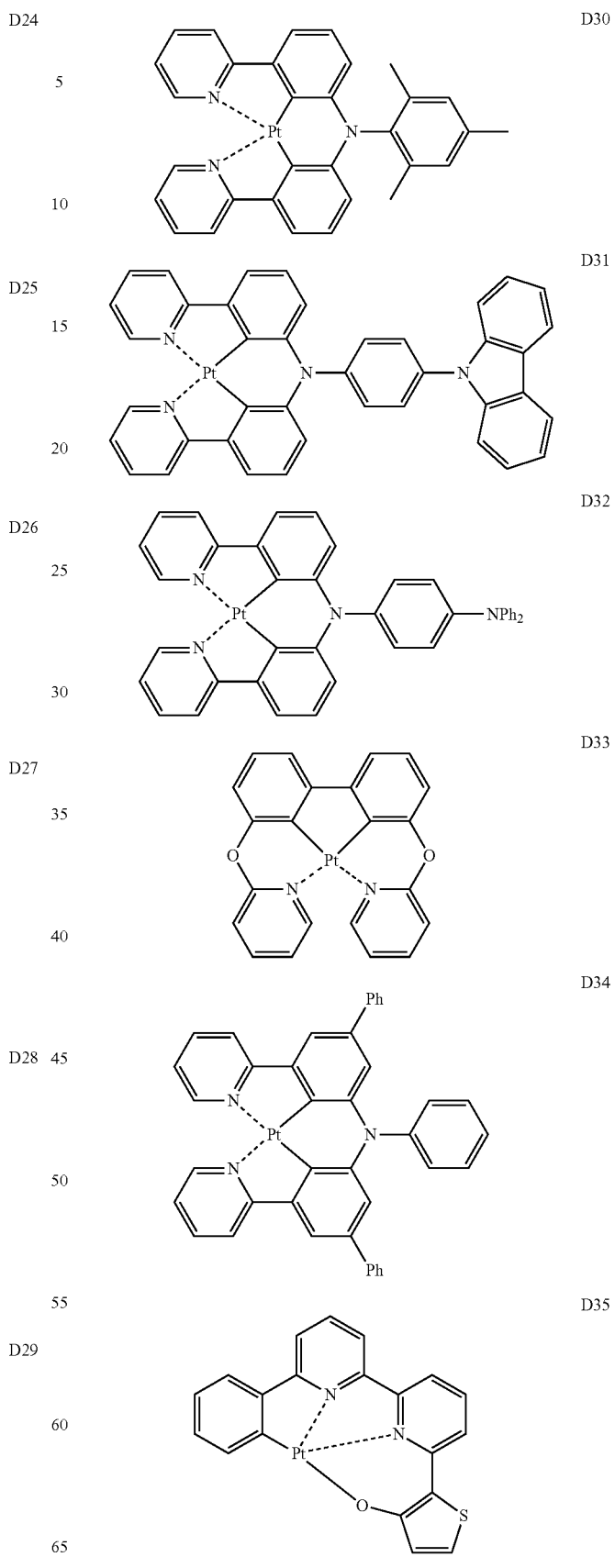

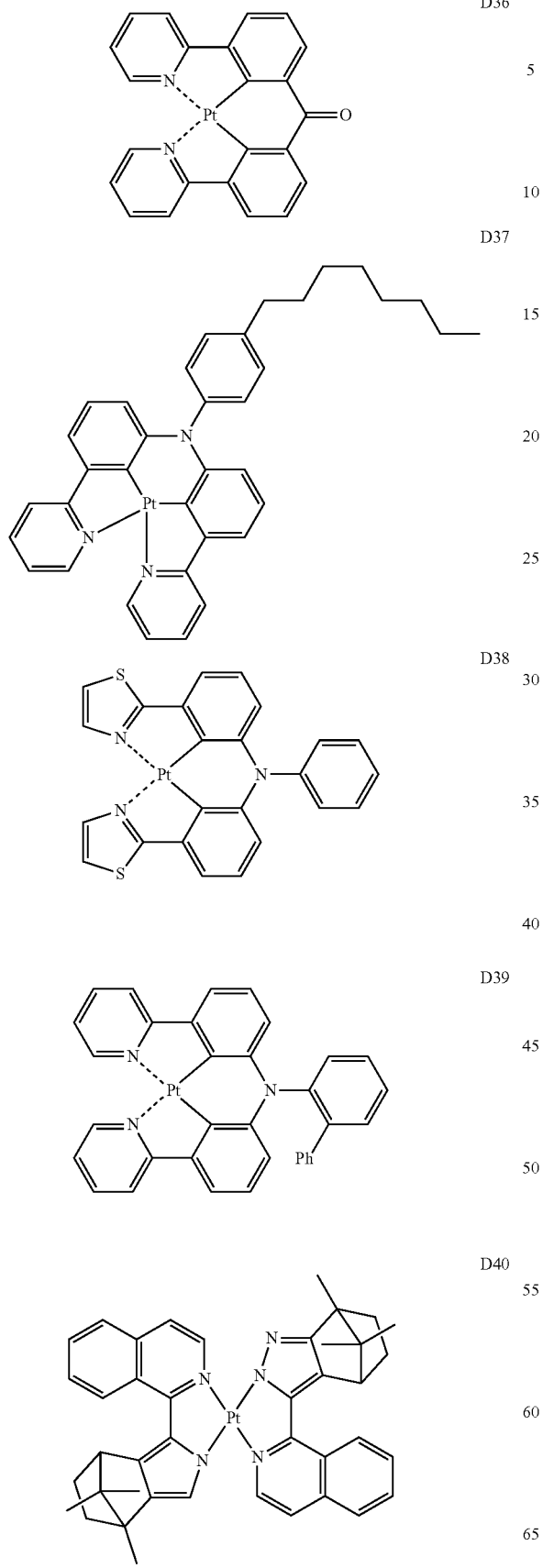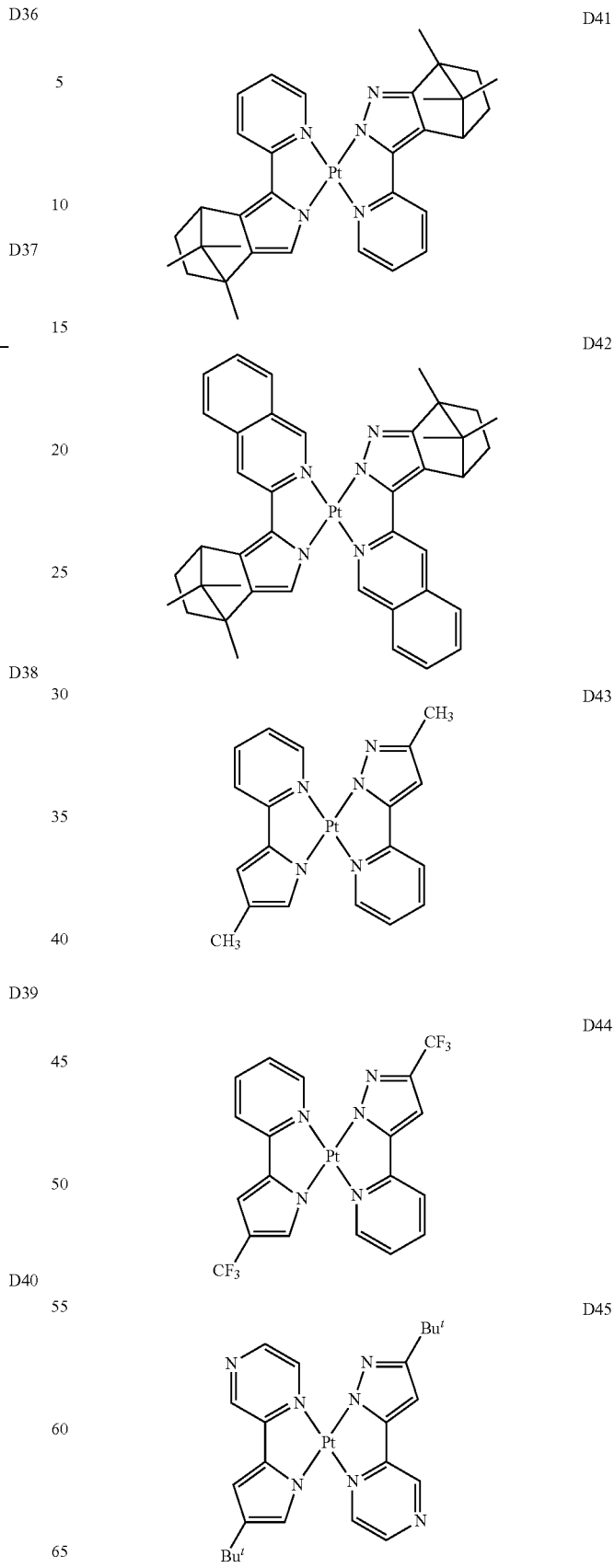

-continued

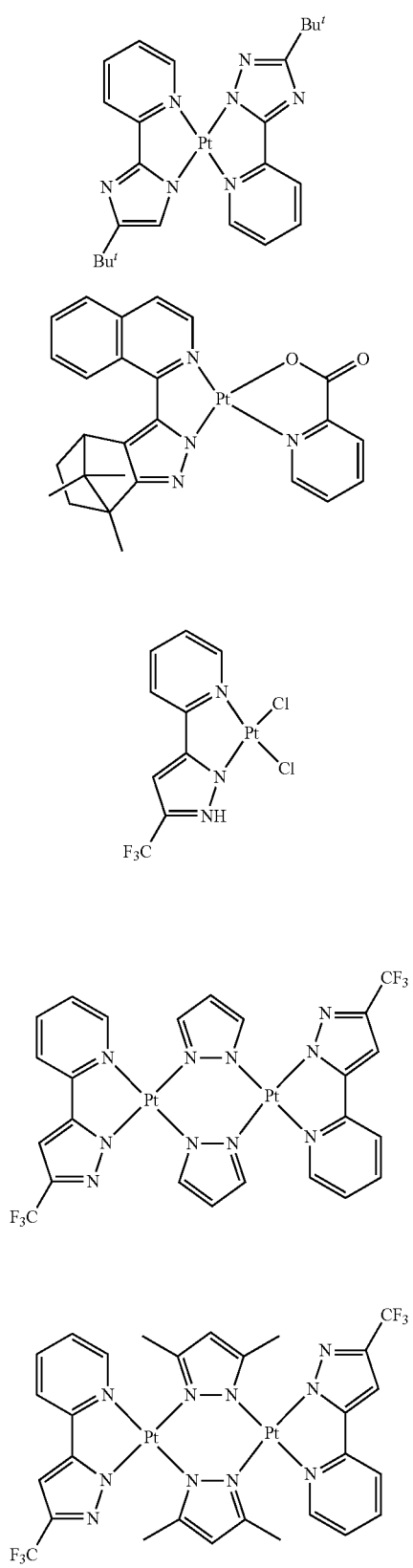

Also, examples of the dopant included in the EML may include, but are not limited to, Os-complexes:

D46

Os(fppz)₂(CO)₂

D47

Os(fppz)₂(PPh₂Me)₂

D48

Os(bppz)₂(PPh₃)₂

D49

Os(fptz)₂(PPh₂Me)₂

D50

Os(hptz)₂(PPhMe₂)₂

When the EML includes a host and a dopant, the amount of the dopant in the EML may be generally in the range of about 0.01 to about 15 parts by weight based on 100 parts by weight of the host, but is not limited thereto.

The thickness of the EML may be in the range of about 100 Å to about 1,000 Å. In some embodiments, the thickness of the EML may be in the range of about 200 Å to about 600 Å. When the thickness of the EML is within these ranges, excellent luminescent properties may be obtained without a substantial increase in driving voltage.

An ETL may be formed on the EML by using various methods such as vacuum deposition, spin coating, or casting. When the ETL is formed by vacuum deposition or spin coating, the deposition and coating conditions may vary according to a used compound. However, in general, the deposition and coating conditions may be almost the same as the condition for forming the HIL. A material for forming the ETL may be the condensed-cyclic compound of Formula 1 described above that stably transports electrons injected from a cathode.

The thickness of the ETL may be in the range of about 100 Å to about 1,000 Å. In some embodiments, the thickness of the ETL may be in the range of about 150 Å to about 500 Å. When the thickness of the ETL is within these ranges, satisfactory electron transport properties may be obtained without a substantial increase in driving voltage In addition, the ETL may further include a metal-containing material, in addition to the condensed-cyclic compound of Formula 1 described above.

The metal-containing material may include a Li-complex. Examples of the Li-complex may include, but are not limited to, lithium quinolate (LiQ) and Compound 203 below:

Compound 203

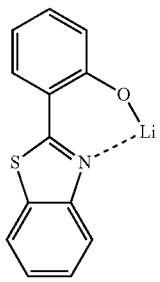

Also, an EIL, which facilitates electron injection from a cathode, may be formed on the ETL, and a material for forming the EIL is not particularly limited.

The material for forming the EIL may include a known material for forming an EIL, such as LiF, NaCl, CsF, $Li_2O$, or BaO. The deposition condition of the EIL may vary according a used compound. However, in general, the condition may be almost the same as the condition for forming the HIL.

The thickness of the EIL may be in the range of about 1 Å to about 100 Å. In some embodiments, the thickness of the EIL may be in the range of about 3 Å to about 90 Å. When the thickness of the EIL is within these ranges, satisfactory electron injection properties may be obtained without a substantial increase in driving voltage.

A second electrode 17 is formed on the organic layer 15. The second electrode 17 may be a cathode, which is an electron injection electrode. In this regard, a metal for forming the second electrode 17 may include a metal having low work function, such as metal, an alloy, an electric conducting compound, and mixtures thereof. The second electrode 17 may be formed as a thin film by using lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type organic light-emitting diode, the second electrode 17 may be formed as a transparent electrode by using ITO or IZO.

The OLED has been described with reference to FIG. 1, but is not limited thereto.

Also, when a phosphorescent dopant is included in the EML, a HBL may be formed between the ETL and the EML or between the H-functional layer and the EML by vacuum deposition, spin coating, casting or LB deposition so as to prevent triplet excitons or holes from being diffused to the ETL. When the HBL is formed by vacuum deposition or spin coating, the conditions thereof may vary according to a used compound. However, in general, the deposition and coating conditions may be almost the same as the condition for forming the HIL. The HBL may include a known hole blocking material. Examples of the known hole blocking material include an oxadiazole derivative, a triazole derivative, and a phenanthroline derivative. For example, BCP may be used as a hole blocking material.

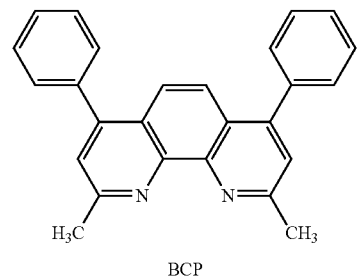 [SMILES: Cc1cc(-c2ccccc2)c2ccc3c(-c4ccccc4)cc(C)nc3c2n1 ; "BCP"]

BCP

The thickness of the HBL may be in the range of about 20 Å to about 1,000 Å. In some embodiments, the thickness of the HBL may be in the range of about 30 Å to about 300 Å. When the thickness of the HBL is within these ranges, excellent hole blocking properties may be obtained without a substantial increase in driving voltage.

Examples of the unsubstituted $C_1$-$C_{60}$ alkyl group (or $C_1$-$C_{60}$ alkyl group) include $C_1$-$C_{60}$ linear or branched alkyl groups such as methyl, ethyl, propyl, isobutyl, sec-butyl, pentyl, iso-amyl, hexyl, and the like. The substituted $C_1$-$C_{60}$ alkyl group may be a group in which at least one hydrogen of the unsubstituted $C_1$-$C_{60}$ alkyl group is substituted with deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, $-N(Q_{11})(Q_{12})$, and $-Si(Q_{13})(Q_{14})(Q_{15})$ (where $Q_{11}$ through $Q_{15}$ may be each independently selected from hydrogen, a $C_1$-$C_{60}$ alkyl group, a $C_2$-$C_{60}$ alkenyl group, a $C_2$-$C_{60}$ alkynyl group, a $C_6$-$C_{60}$ aryl group, and a $C_2$-$C_{60}$ heteroaryl group).

The unsubstituted $C_1$-$C_{60}$ alkoxy group (or $C_1$-$C_{60}$ alkoxy group) has a formula of —OA (in this regard, A is the unsubstituted $C_1$-$C_{60}$ alkyl group as described above) and examples thereof include methoxy, ethoxy, isopropyloxy, and the like. At least one hydrogen atom of the unsubstituted $C_1$-$C_{60}$ alkoxy group may be substituted with the same substituent as in the substituted $C_1$-$C_{60}$ alkyl group described above.

The unsubstituted $C_2$-$C_{60}$ alkenyl group (or $C_2$-$C_{60}$ alkenyl group) is interpreted to contain at least one carbon-carbon double bond in the center or at a terminal of the unsubstituted $C_2$-$C_{60}$ alkyl group. Examples of the unsubstituted $C_2$-$C_{60}$ alkenyl group include ethenyl, propenyl, butenyl, and the like. At least one hydrogen atom of the unsubstituted $C_2$-$C_{60}$ alkenyl group may be substituted with the same substituent as in the substituted $C_1$-$C_{60}$ alkyl group described above.

The unsubstituted $C_2$-$C_{60}$ alkynyl group (or $C_2$-$C_{60}$ alkynyl group) is interpreted to contain at least one carbon-carbon triple bond in the center or at a terminal of the $C_2$-$C_{60}$ alkyl group defined above. Examples of the unsubstituted $C_2$-$C_{60}$ alkynyl group include ethynyl, propynyl, and the like. At least one hydrogen atom of the unsubstituted $C_2$-$C_{60}$ alkynyl group may be substituted with the same substituent as in the substituted $C_1$-$C_{60}$ alkyl group described above.

The unsubstituted $C_6$-$C_{60}$ aryl group indicates a monovalent group having an aromatic carbocyclic system that has 5 to 60 carbon atoms and at least one aromatic ring and the unsubstituted $C_6$-$C_{60}$ arylene group indicates a divalent group having an aromatic carbocyclic system that has 5 to 60 carbon atoms and at least one aromatic ring. If the $C_6$-$C_{60}$ aryl group and the $C_6$-$C_{60}$ arylene group each independently have two or more aromatic rings, the rings may be fused with each other. At least one hydrogen atom of each of the unsubstituted $C_6$-$C_{60}$ aryl group and the unsubstituted $C_6$-$C_{60}$ arylene group may be substituted with the same substituent as in the substituted $C_1$-$C_{60}$ alkyl group described above.

Examples of the substituted or unsubstituted $C_6$-$C_{60}$ aryl group include, but are not limited to, a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- and p-fluorophenyl group, and a dichlorophenyl group), a dicyanophenyl group, a trifluoromethoxyphenyl group, an o-, m-, and p-tolyl group, an o-, m- and p-cumenyl group, a mesityl group, a phenoxyphenyl group, an (α,α-dimethylbenzene)phenyl group, a (N,N'-dimethyl)aminophenyl group, a (N,N'-diphenyl) aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl, a pyranthrenyl group, and an ovalenyl group. Examples of the substituted $C_6$-$C_{60}$ aryl group may be easily understood with reference to the examples of the unsubstituted $C_6$-$C_{60}$ aryl group described above and the substituents of the substituted $C_1$-$C_{60}$ alkyl group. Examples of the substituted or unsubstituted $C_6$-$C_{60}$ arylene group may be easily understood with reference to the substituted or unsubstituted $C_6$-$C_{60}$ aryl group described above.

The unsubstituted $C_2$-$C_{60}$ heteroaryl group indicates a monovalent group having at least one aromatic ring system including carbon rings and at least one hetero atom selected from the group consisting of N, O, P, and S, and the unsubstituted $C_2$-$C_{60}$ heteroarylene group indicates a divalent group having at least one aromatic ring system including carbon rings and at least one hetero atom selected from the group consisting of N, O, P, and S. In this regard, if the $C_2$-$C_{60}$ heteroaryl group and the $C_2$-$C_{60}$ heteroarylene group each independently have two or more aromatic rings, the rings may be fused with each other. At least one hydrogen atom of each of the unsubstituted $C_2$-$C_{60}$ heteroaryl group and the unsubstituted $C_2$-$C_{60}$ heteroarylene group may be substituted with the same substituents as in the $C_1$-$C_{60}$ alkyl group described above.

Examples of the unsubstituted $C_2$-$C_{60}$ heteroaryl group include, but are not limited to, a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily understood with reference to the examples of the substituted or unsubstituted $C_2$-$C_{60}$ arylene group.

The substituted or unsubstituted $C_6$-$C_{60}$ aryloxy group has a formula of —OA2 wherein A2 is the substituted or unsubstituted $C_6$-$C_{60}$ aryl group as described above, and the substituted or unsubstituted $C_6$-$C_{60}$ arylthio group has a formula of —SA3 wherein $A_3$ is the substituted or unsubstituted $C_6$-$C_{60}$ aryl group described above.

An OLED according to an embodiment will now be described in greater detail with reference to the following Examples. These Examples are for illustrative purposes only and are not intended to limit the scope of the embodiments.

EXAMPLES

Synthesis Example 1

Synthesis of Compound 6

Compound 6 was synthesized according to Reaction Scheme 1 below:

Reaction scheme 1

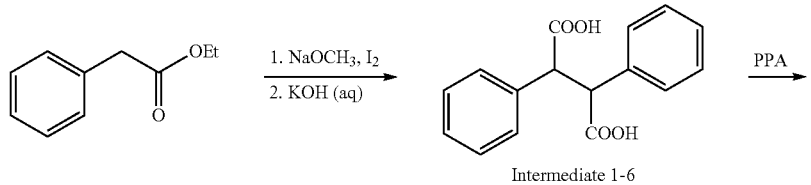

Intermediate 1-6

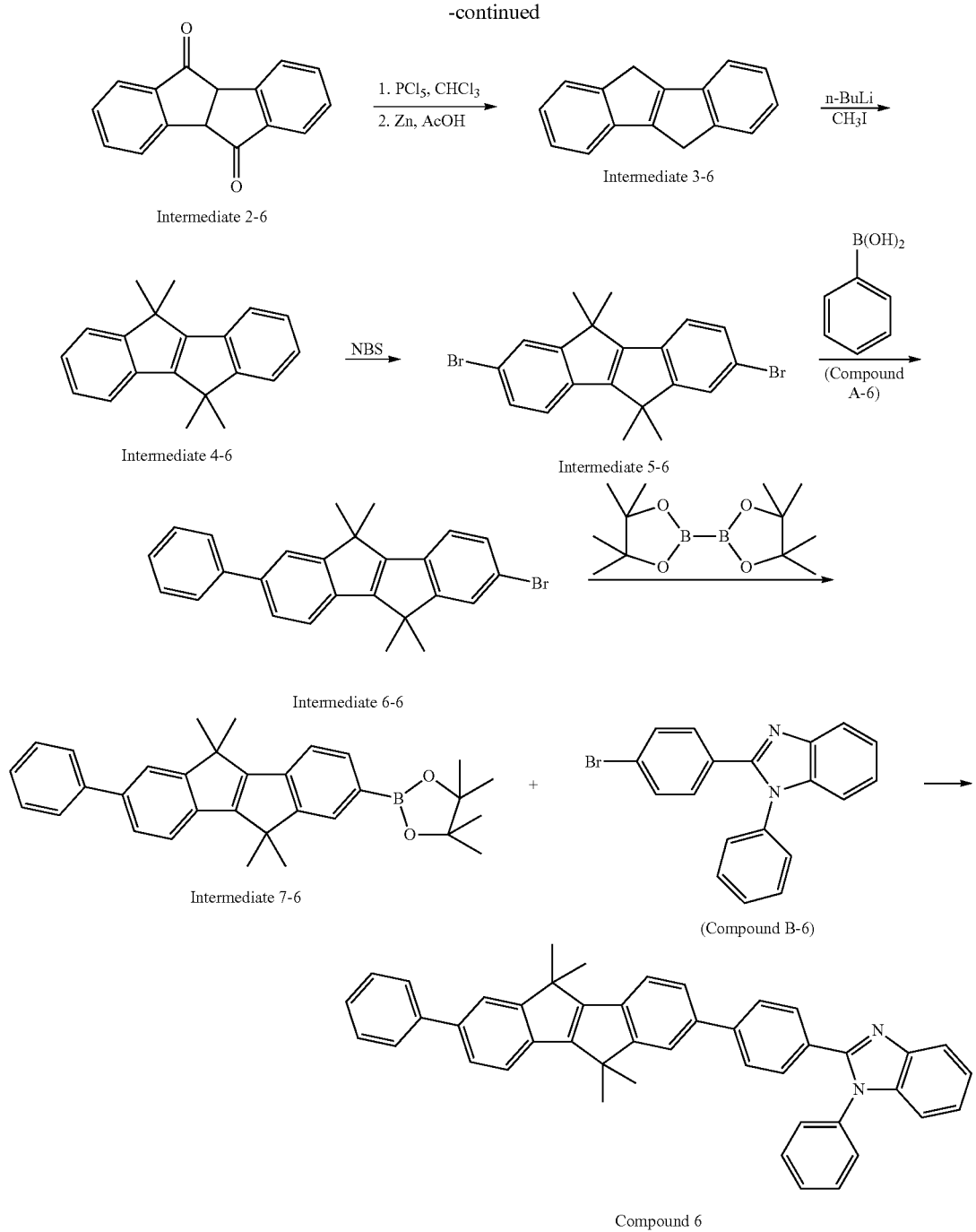

Synthesis of Intermediate 1-6

A solution prepared by dissolving 2.54 g (10 mmol) of $I_2$ in 12 ml of THF was added to a reactant prepared by dissolving 3.3 ml (20 mmol) of ethyl phenylacetate and 1.08 g (20 mmol) of $NaOCH_3$ in 25 ml of THF. The reaction solution was stirred at −78° C. for 10 minutes and 5 ml of 5% $NaHSO_4$(aq) was then added to the reaction solution at room temperature. Thereafter, 4.21 g (75 mmol) of KOH dissolved in 65 ml of water was added to the resulting reaction solution and stirred at 40° C. for 5 hours, and 5 ml of concentrated HCl was added thereto. The obtained reaction solution was cooled down to room temperature to obtain a precipitate. The precipitate was filtered, the filtrate was washed with 5 ml of water and dried in vacuum for 24 hours to obtain 2.66 g of Intermediate 1-6 (yield: 49%). The obtained compound was confirmed by mass spectrometry/fast atom bombardment (MS/FAB).

$C_{16}H_{14}O_4$: calc. 270.09. found 270.25.

Synthesis of Intermediate 2-6

5.41 g (20 mmol) of Intermediate 1-6 was added to 500 ml of a polyphosphoric acid (PPA) solution heated at 100° C. and the resulting solution was then stirred at 125° C. for 21 hours. Subsequently, the reaction solution was further heated at 150° C. for 2 hours. The reaction solution was cooled down to 80° C., 600 ml of water was added thereto, and the resulting reaction solution was stirred for 2 hours to obtain a precipitate. The precipitate was filtered, the filtrate was dissolved in 140 ml of hot aqueous $NaHCO_3$ solution, and the resultant solution was stirred for 30 hours to obtain a precipitate. The precipitate was filtered and the filtrate was dried in vacuum for 12 hours to obtain 4.03 g of Intermediate 2-6 (yield: 86%). The obtained compound was confirmed by MS/FAB.

$C_{16}H_{10}O_2$: calc. 234.07. found 234.20.

Synthesis of Intermediate 3-6

4.69 g (20 mmol) of Intermediate 2-6 was dissolved in 20 ml of chloroform, 8.75 g (42 mmol) of $PCl_5$ was added thereto, and the resulting solution was refluxed at 50° C. for 30 hours. The reaction solution was cooled down to room temperature and the solvent was removed in vacuum therefrom to obtain a crude product. The crude product was diluted with boiling acetic acid and 25 g of zinc dust was slowly added thereto. The obtained precipitate was filtered and washed with boiling acetic acid. Thereafter, the obtained crude product was purified with silicagel column chromatography to obtain 3.71 g of Intermediate 3-6 (yield: 91%). The obtained compound was confirmed by MS/FAB.

$C_{16}H_{12}$: calc. 204.09. found 204.31.

Synthesis of Intermediate 4-6

2.04 g (10 mmol) of Intermediate 3-6 and 37.5 ml (60 mmol) of n-BuLi (1.60M hexane solution) were mixed in THF at −78° C. to induce a reaction therebetween. Subsequently, 3.8 ml (60 mmol) of iodomethane was added to the reaction solution, the resulting solution was stirred at room temperature for 3 hours, and 5 ml of 1N HCl (aq) was added thereto. An organic layer was separated from the reaction solution and the remaining water layer was extracted twice with 100 ml of dichloromethane. The obtained organic layer was dried with magnesium sulfate and a solvent was evaporated therefrom to obtain a crude product. The crude product was purified with silicagel column chromatography to obtain 2.03 g of Intermediate 4-6 (yield: 78%). The obtained compound was confirmed by MS/FAB.

$C_{20}H_{20}$: calc. 260.15. found 260.21.

Synthesis of Intermediate 5-6

3.56 g (20 mmol) of N-bromosuccinimide (NBS) was completely dissolved in 50 ml of dimethylformamide (DMF), 2.60 g (10 mmol) of Intermediate 4-6 was then added thereto, and the resulting solution was stirred at room temperature for 24 hours. The reaction solution was extracted twice with 50 ml of water and 50 ml of dichloromethane. The obtained organic layer was dried with magnesium sulfate and a solvent was evaporated therefrom to obtain a crude product. The crude product was purified with silicagel column chromatography to obtain 2.55 g of Intermediate 5-6 (yield: 61%). The obtained compound was confirmed by MS/FAB.

$C_{20}H_{18}Br_2$: calc. 415.97. found 416.11.

Synthesis of Intermediate 6-6

2.11 g (5.09 mmol) of Intermediate 5-6, 0.34 g (2.99 mmol) of phenyl boronic acid (Compound A-6), 0.29 g (0.25 mmol) of tetrakis(triphenylphosphin)palladium (Pd(PPh$_3$)$_4$), and 0.62 g (4.48 mmol) of $K_2CO_3$ were dissolved in 60 ml of a mixed solution of THF and $H_2O$ (a volume ratio of 2:1), and the resultant solution was then stirred at 70° C. for 5 hours. The reaction solution was cooled down to room temperature, 40 ml of water was added thereto, and the resultant solution was extracted three times with 50 ml of ethylether. The obtained organic layer was dried with magnesium sulfate and a solvent was evaporated therefrom to obtain a crude product. The crude product was purified with silicagel column chromatography to obtain 0.88 g of Intermediate 6-6 (yield: 74%). The obtained compound was confirmed by MS/FAB.

$C_{26}H_{23}Br$: calc. 414.09. found 414.21.

Synthesis of Intermediate 7-6

4.15 g (10.0 mmol) of Intermediate 6-6, 2.54 g (10.0 mmol) of bis(pinacolato)diborane, 0.36 g (0.5 mmol) of [1,1'-bis(diphenylphosphino)ferrocene]dichloro palladium (II) ($PdCl_2(dppf)_2$), and 2.94 g (30.0 mmol) of KOAc were dissolved in 40 ml of DMSO, and the resultant solution was stirred at 80° C. for 6 hours. The reaction solution was cooled down to room temperature and then extracted three times with 50 ml of water and 50 ml of diethylether. The obtained organic layer was dried with magnesium sulfate and a solvent was evaporated therefrom to obtain a crude product. The crude product was purified with silicagel column chromatography to obtain 3.69 g of Intermediate 7-6 (yield: 80%). The obtained compound was confirmed by MS/FAB.

$C_{32}H_{35}BO_2$: calc. 462.27. found 462.33.

Synthesis of Compound 6

1.02 g (2.20 mmol) of Intermediate 7-6, 0.69 g (2.20 mmol) of 2-(4-bromophenyl)-1-phenyl-1-benzoimidazole (Compound B-6), 0.127 g (0.11 mmol) of Pd(PPh$_3$)$_4$, and 0.45 g (3.3 mmol) of $K_2CO_3$ were dissolved in 40 ml of a mixed solution of THF and $H_2O$ (a volume ratio of 2:1), and the resultant solution was stirred at 70° C. for 5 hours. The reaction solution was cooled down to room temperature, 30 ml of water was added thereto, and the resultant solution was then extracted three times with 30 ml of ethylether. The obtained organic layer was dried with magnesium sulfate and a solvent was evaporated therefrom to obtain a crude product. The crude product was purified with silicagel column chromatography to obtain 1.01 g of Compound 6 (yield: 76%). The obtained compound was confirmed by $^1$H nuclear magnetic resonance (NMR) and MS/FAB.

$^1$H NMR (CDCl$_3$, 400 MHz) □ δ: 8.82-8.78 (m, 4H), 8.28 (dd, 1H), 7.98-7.96 (m, 1H), 7.85 (d, 1H), 7.73 (d, 1H), 7.67-7.59 (m, 6H), 7.53-7.47 (m, 2H), 7.43-7.37 (m, 4H), 7.35-7.33 (m, 1H), 1.45 (s, 6H), 1.35 (s, 6H)

$C_{45}H_{36}N_2$: calc. 604.28. found 605.33.

Synthesis Example 2

Synthesis of Compound 15

Compound 15 was synthesized in the same manner as in Synthesis Example 1, except that pyridin-2-yl-2-boronic acid was used instead of phenyl boronic acid (Compound A-6) in the synthesis of Intermediate 6-6 and 3-(3-bromo-5-(pyridin-3-yl)phenyl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.96-8.94 (m, 2H), 8.68-8.65 (m, 3H), 8.34 (dd, 1H), 8.14 (d, 1H), 8.05 (dt, 2H), 7.97-7.88 (m, 4H), 7.77-7.66 (m, 3H), 7.50-7.43 (m, 3H), 7.38-7.35 (m, 1H), 7.16 (dd, 1H) 1.45 (s, 6H), 1.37 (s, 6H))

C$_{41}$H$_{33}$N$_3$: calc. 567.26. found 568.38.

Synthesis Example 3

Synthesis of Compound 28

Compound 28 was synthesized in the same manner as in Synthesis Example 1, except that naphthalen-2-yl-2-boronic acid was used instead of phenyl boronic acid (Compound A-6) in the synthesis of Intermediate 6-6 and 2-bromo-4,6-diphenyl-1,3,5-triazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.83-8.78 (m, 4H), 8.28 (dd, 1H), 8.20-8.18 (m, 1H), 8.02 (d, 1H), 7.97-7.96 (m, 1H), 7.93-7.85 (m, 4H), 7.80-7.72 (m, 2H), 7.63-7.57 (m, 5H), 7.44-7.38 (m, 4H), 1.47 (s, 6H), 1.37 (s, 6H)

C$_{45}$H$_{35}$N$_3$: calc. 617.28. found 618.39.

Synthesis Example 4

Synthesis of Compound 41

Compound 41 was synthesized in the same manner as in Synthesis Example 1, except that quinolin-2-yl-2-boronic acid was used instead of phenyl boronic acid (Compound A-6) in the synthesis of Intermediate 6-6 and 2-(2-bromonaphthalen-6-yl)pyrazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.94 (t, 1H), 8.69-8.67 (m, 1H), 8.53 (t, 1H), 8.47-8.43 (m, 2H), 8.40-8.38 (m, 1H), 8.32-8.28 (m, 2H), 8.19-8.17 (m, 1H), 8.05-7.97 (m, 4H), 7.93-7.65 (m, 6H), 7.42 (d, 1H), 7.38-7.36 (m, 1H), 1.43 (s, 6H), 1.38 (s, 6H)

C$_{43}$H$_{33}$N$_3$: calc. 591.26. found 592.29.

Synthesis Example 5

Synthesis of Compound 49

Compound 49 was synthesized in the same manner as in Synthesis Example 1, except that phenanthren-9-yl-9-boronic acid was used instead of phenyl boronic acid (Compound A-6) in the synthesis of Intermediate 6-6 and 2-bromo-6-(pyridin-4-yl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.66-8.63 (m, 3H), 8.43-8.41 (m, 1H), 8.37 (dd, 1H), 8.20 (d, 1H), 8.05-7.96 (m, 4H), 7.89-7.85 (m, 1H), 7.80-7.61 (m, 7H), 7.54-7.51 (m, 2H), 7.22-7.20 (m, 1H), 7.15-7.12 (m, 1H), 1.42 (s, 6H), 1.37 (s, 6H)

C$_{43}$H$_{34}$N$_2$: calc. 590.27. found 591.30.

Synthesis Example 6

Synthesis of Compound 57

Compound 57 was synthesized in the same manner as in Synthesis Example 1, except that 1,10-phenanthrolin-2-yl-2-boronic acid was used instead of phenyl boronic acid (Compound A-6) in the synthesis of Intermediate 6-6 and Compound B-57 below was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 9.17 (dd, 1H), 8.48 (dd, 1H), 8.33-8.26 (m, 2H), 8.20-8.16 (m, 2H), 8.10-8.08 (m, 1H), 7.91-7.88 (m, 1H), 7.83-7.76 (m, 4H), 7.72-7.69 (m, 2H), 7.65-7.58 (m, 4H), 7.50-7.40 (m, 3H), 1.42 (s, 6H), 1.38 (s, 6H)

C$_{45}$H$_{33}$N$_3$: calc. 615.26. found 616.37.

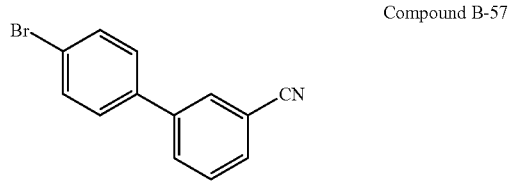 [SMILES: N#Cc1cccc(-c2ccc(Br)cc2)c1]

Compound B-57

Synthesis Example 7

Synthesis of Compound 1

Compound 1 was synthesized in the same manner as in Synthesis Example 1, except that 2-bromopyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.68-8.65 (m, 1H), 8.33 (dd, 1H), 7.93-7.91 (m, 1H), 7.85 (d, 1H), 7.77-7.73 (m, 1H), 7.69-7.65 (m, 4H), 7.54-7.47 (m, 2H), 7.44-7.38 (m, 2H), 7.35-7.33 (m, 1H), 7.18-7.15 (m, 1H), 1.47 (s, 6H), 1.37 (s, 6H)

C$_{31}$H$_{27}$N: calc. 413.21. found 414.32.

Synthesis Example 8

Synthesis of Compound 2

Compound 2 was synthesized in the same manner as in Synthesis Example 1, except that 6-bromoquinoline was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.73 (dd, 1H), 8.25-8.23 (m, 1H), 8.18-8.15 (m, 2H), 8.05-8.00 (m, 2H), 7.85 (d, 1H), 7.67-7.65 (m, 2H), 7.55-7.45 (m, 4H), 7.43-7.38 (m, 2H), 7.33-7.31 (m, 2H), 1.45 (s, 6H), 1.37 (s, 6H)

C$_{35}$H$_{29}$N: calc. 463.23. found 464.31.

Synthesis Example 9

Synthesis of Compound 5

Compound 5 was synthesized in the same manner as in Synthesis Example 1, except that 2-bromo-4,6-diphenyl-1,3,5-triazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.82-8.78 (m, 4H), 8.28 (dd, 1H), 7.98-7.96 (m, 1H), 7.85 (d, 1H), 7.73 (d, 1H), 7.67-7.59 (m, 6H), 7.53-7.47 (m, 2H), 7.43-7.37 (m, 4H), 7.35-7.33 (m, 1H), 1.45 (s, 6H), 1.35 (s, 6H)

C$_{41}$H$_{33}$N$_3$: calc. 567.26. found 568.31.

Synthesis Example 10

Synthesis of Compound 8

Compound 8 was synthesized in the same manner as in Synthesis Example 1, except that 2-(4-bromo-phenyl)-4,6-diphenyl-1,3,5-triazine was used instead of 2-(4-bromophenyl)-1-phenyl-1-benzoimidazole (Compound B-6) in the synthesis of Compound 6. The synthesized compound was confirmed by $^1$H NMR and MS/FAB.

1H NMR (CDCl$_3$, 400 MHz) δ: 8.10-8.04 (m, 4H), 7.90 (d, 1H), 7.85 (d, 1H), 7.79-7.77 (m, 1H), 7.65-7.58 (m, 6H), 7.52-7.28 (m, 9H), 7.21-7.17 (m, 3H), 1.48 (s, 6H), 1.37 (s, 6H)

C$_{45}$H$_{36}$N$_2$: calc. 643.29. found 644.32.

Synthesis Example 11

Synthesis of Compound 11

Compound 11 was synthesized in the same manner as in Synthesis Example 1, except that 3-(6-bromopyridin-3-yl)quinoline was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 9.13-9.11 (m, 1H), 8.89-8.85 (m, 1H), 8.58-8.57 (m, 1H), 8.35 (dd, 1H), 8.16-8.14 (m, 1H), 8.05-8.01 (m, 2H), 7.96-7.94 (m, 1H), 7.90-7.84 (m, 2H), 7.71-7.65 (m, 4H), 7.51-7.48 (m, 3H), 7.42-7.38 (m, 2H), 7.34-7.31 (1H), 1.42 (s, 6H), 1.37 (s, 6H)

C$_{40}$H$_{32}$N$_2$: calc. 540.25. found 541.36.

Synthesis Example 12

Synthesis of Compound 13

Compound 13 was synthesized in the same manner as in Synthesis Example 1, except that pyridin-2-yl-2-boronic acid was used instead of phenyl boronic acid (Compound A-6) in the synthesis of Intermediate 6-6 and 3-bromo-9-phenyl-9H-carbazole was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 8.68-8.65 (m, 1H), 8.33 (dd, 1H), 8.24-8.22 (m, 1H), 8.08-8.06 (m, 1H), 7.95-7.93 (m, 2H), 7.77-7.66 (m, 5H), 7.54-7.47 (m, 6H), 7.39-7.28 (m, 3H), 7.21-7.15 (m, 2H), 1.42 (s, 6H), 1.37 (s, 6H)

C$_{43}$H$_{34}$N$_2$: calc. 578.27. found 579.39.

Synthesis Example 13

Synthesis of Compound 16

Compound 16 was synthesized in the same manner as in Synthesis Example 1, except that pyridin-2-yl-2-boronic acid was used instead of phenyl boronic acid (Compound A-6) in the synthesis of Intermediate 6-6 and Compound B-16 below was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 8.68-8.66 (m, 1H), 8.35-8.30 (m, 3H), 8.03-8.01 (m, 1H), 7.94-7.85 (m, 5H), 7.77-7.75 (m, 1H), 7.68-7.65 (m, 2H), 7.47-7.40 (m, 3H), 7.37-7.33 (m, 1H), 7.16 (dd, 1H) 1.43 (s, 6H), 1.36 (s, 6H)

C$_{37}$H$_{31}$N$_2$S: calc. 546.21. found 547.33.

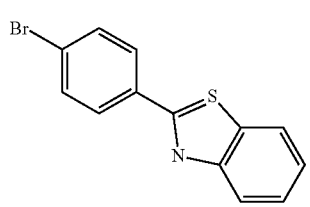

Compound B-16

Synthesis Example 14

Synthesis of Compound 17

Compound 17 was synthesized in the same manner as in Synthesis Example 1, except that pyridin-2-yl-2-boronic acid was used instead of phenyl boronic acid (Compound A-6) in the synthesis of Intermediate 6-6 and Compound B-17 below was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.68-8.66 (m, 1H), 8.33 (dd, 1H), 8.23-8.20 (m, 2H), 7.94-7.59 (m, 2H), 7.83-7.81 (m, 1H), 7.77-7.66 (m, 5H), 7.45-7.39 (m, 4H), 7.29-7.23 (m, 1H), 7.18-7.15 (m, 1H) 1.42 (s, 6H), 1.37 (s, 6H)

C$_{37}$H$_{31}$N$_2$O: calc. 530.23. found 531.34.

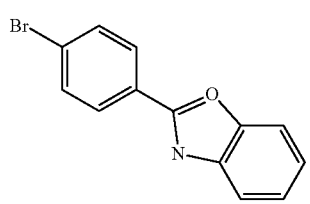

Compound B-17

Synthesis Example 15

Synthesis of Compound 21

Compound 21 was synthesized in the same manner as in Synthesis Example 1, except that pyridin-2-yl-2-boronic acid was used instead of phenyl boronic acid (Compound A-6) in the synthesis of Intermediate 6-6 and 2-bromo-5-(3,5-difluorophenyl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 9.01-9.00 (m, 1H), 8.68-8.67 (m, 1H), 8.37-8.32 (m, 2H), 8.05-7.94 (m, 4H), 7.77-7.66 (m, 4H), 7.21-7.15 (m, 3H), 6.72-6.77 (m, 1H), 1.43 (s, 6H), 1.38 (s, 6H)

C$_{36}$H$_{29}$N$_2$F$_2$: calc. 526.22. found 527.31.

Synthesis Example 16

Synthesis of Compound 23

Compound 23 was synthesized in the same manner as in Synthesis Example 1, except that pyridin-2-yl-2-boronic acid was used instead of phenyl boronic acid (Compound A-6) in the synthesis of Intermediate 6-6 and 2-(2-bromonaphthalen-6-yl)pyrazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.94-8.92 (m, 1H), 8.69-8.66 (m, 2H), 8.55-8.53 (m, 1H), 8.46-8.44 (m, 1H), 8.40-8.29 (m, 3H), 8.03-7.97 (m, 2H), 7.94-7.88 (m, 3H), 7.77-7.73 (m, 1H), 7.68-7.66 (m, 2H), 7.44-7.38 (m, 2H), 7.16 (dd, 1H), 1.42 (s, 6H), 1.37 (s, 6H)

$C_{39}H_{32}N_3$: calc. 541.25. found 542.39.

Synthesis Example 17

Synthesis of Compound 27

Compound 27 was synthesized in the same manner as in Synthesis Example 1, except that naphthalen-2-yl-2-boronic acid was used instead of phenyl boronic acid (Compound A-6) in the synthesis of Intermediate 6-6 and 2-bromo-6-(pyridin-4-yl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.65-8.63 (m, 2H), 8.37 (dd, 1H), 8.20-8.18 (m, 1H), 8.04-8.01 (m, 3H), 7.97-7.96 (m, 1H), 7.93-7.85 (m, 4H), 7.80-7.70 (m, 4H), 7.62-7.57 (m, 1H), 7.53-7.49 (m, 1H), 7.44-7.41 (m, 1H), 7.38-7.36 (m, 1H), 1.42 (s, 6H), 1.37 (s, 6H)

$C_{39}H_{32}N_3$: calc. 540.25. found 541.36.

Synthesis Example 18

Synthesis of Compound 29

Compound 29 was synthesized in the same manner as in Synthesis Example 1, except that naphthalen-2-yl-2-boronic acid was used instead of phenyl boronic acid (Compound A-6) in the synthesis of Intermediate 6-6. The synthesized compound was confirmed by $^1$H NMR and MS/FAB.

$^1$H NMR (CDCl$_3$, 400 MHz) δ: 8.18-8.17 (m, 1H), 8.07-8.01 (m, 3H), 7.93-7.83 (m, 4H), 7.80-7.74 (m, 4H), 7.66 (dd, 1H), 7.62-7.49 (m, 4H), 7.45-7.35 (m, 7H), 7.32-7.28 (m, 1H), 7.24-7.20 (m, 1H), 1.45 (s, 6H), 1.35 (s, 6H)

$C_{49}H_{38}N_2$: calc. 654.30. found 655.45.

Synthesis Example 19

Synthesis of Compound 32

Compound 32 was synthesized in the same manner as in Synthesis Example 1, except that naphthalen-2-yl-2-boronic acid was used instead of phenyl boronic acid (Compound A-6) in the synthesis of Intermediate 6-6 and 2-(2-bromo-9,9-dimethyl-9H-fluoren-7-yl)pyrazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.87 (t, 1H), 8.46 (dt, 2H), 8.20-8.18 (m, 1H), 8.07-7.98 (m, 3H), 7.93-7.72 (m, 9H), 7.65-7.58 (m, 5H), 7.53-7.51 (m, 1H), 7.44-7.41 (m, 1H), 7.38-7.35 (m, 5H), 1.63 (m, 6H), 1.37 (s, 6H)

$C_{49}H_{37}N_2$: calc. 656.31. found 657.33.

Synthesis Example 20

Synthesis of Compound 33

Compound 33 was synthesized in the same manner as in Synthesis Example 1, except that quinolin-2-yl-2-boronic acid was used instead of phenyl boronic acid (Compound A-6) in the synthesis of Intermediate 6-6 and 2-bromo-4,6-diphenylpyrimidine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.45 (dd, 1H), 8.31-8.26 (m, 5H), 8.19-8.15 (m, 2H), 8.05-8.01 (m, 2H), 7.99 (s, 1H), 7.88-7.83 (m, 2H), 7.80-7.65 (m, 4H), 7.53-7.48 (m, 4H), 7.31-7.26 (m, 2H), 1.47 (m, 6H), 1.42 (s, 6H)

$C_{45}H_{35}N_3$: calc. 617.28. found 618.31.

Synthesis Example 21

Synthesis of Compound 34

Compound 34 was synthesized in the same manner as in Synthesis Example 1, except that quinolin-2-yl-2-boronic acid was used instead of phenyl boronic acid (Compound A-6) in the synthesis of Intermediate 6-6 and 4-(3-bromo-5-(pyridin-4-yl)phenyl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.80-8.76 (m, 4H), 8.45 (dd, 1H), 8.29 (d, 1H), 8.19-8.14 (m, 2H), 8.05-8.01 (m, 2H), 7.97-7.96 (m, 1H), 7.93-7.91 (m, 2H), 7.86-7.65 (m, 4H), 7.55-7.50 (m, 4H), 7.43 (d, 1H), 7.38-7.36 (m, 1H), 1.42 (s, 6H), 1.37 (s, 6H)

$C_{40}H_{35}N3$: calc. 617.28. found 618.39.

Synthesis Example 22

Synthesis of Compound 38

Compound 38 was synthesized in the same manner as in Synthesis Example 1, except that quinolin-2-yl-2-boronic acid was used instead of phenyl boronic acid (Compound A-6) in the synthesis of Intermediate 6-6 and 4-(6-bromopyridin-2-yl)benzonitrile was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) ☐ δ: 8.45 (dd, 1H), 8.37 (dd, 1H), 8.34-8.28 (m, 3H), 8.19-8.15 (m, 1H), 8.05-8.01 (m, 2H), 7.97-7.95 (m, 1H), 7.86-7.72 (m, 7H), 7.69-7.63 (m, 3H), 1.45 (s, 6H), 1.35 (s, 6H)

$C_{41}H_{31}N_3$: calc. 565.25. found 566.37.

Synthesis Example 23

Synthesis of Compound 40

Compound 40 was synthesized in the same manner as in Synthesis Example 1, except that quinolin-2-yl-2-boronic acid was used instead of phenyl boronic acid (Compound A-6) in the synthesis of Intermediate 6-6 and Compound B-40 below was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 8.46-8.43 (m, 3H), 8.37 (dd, 1H), 8.30-8.25 (m, 2H), 8.19-8.17 (m, 1H), 8.10-8.08 (m, 1H), 8.05-8.01 (m, 2H), 7.97-7.95 (m, 1H), 7.86-7.84 (m, 1H), 7.80-7.72 (m, 6H), 7.68-7.65 (m, 2H), 7.46-7.35 (m, 2H), 1.42 (s, 6H), 1.37 (s, 6H)

C$_{46}$H$_{33}$N$_2$S: calc. 646.24. found 647.35.

Synthesis Example 24

Synthesis of Compound 43

Compound 43 was synthesized in the same manner as in Synthesis Example 1, except that phenanthren-9-yl-9-boronic acid was used instead of phenyl boronic acid (Compound A-6) in the synthesis of Intermediate 6-6 and 3-bromopyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 8.97-8.95 (m, 1H), 8.66-8.63 (m, 2H), 8.43-8.41 (m, 1H), 8.20 (d, 1H), 8.08 (dt, 1H), 8.00 (dd, 1H), 7.91 (d, 1H), 7.80-7.75 (m, 2H), 7.68-7.61 (m, 3H), 7.54-7.46 (m, 3H), 7.42-7.40 (m, 1H), 7.20-7.11 (m, 2H), 1.39 (s, 6H), 1.37 (s, 6H)

C$_{39}$H$_{31}$N: calc. 513.24. found 514.35.

Synthesis Example 25

Synthesis of Compound 44

Compound 44 was synthesized in the same manner as in Synthesis Example 1, except that phenanthren-9-yl-9-boronic acid was used instead of phenyl boronic acid (Compound A-6) in the synthesis of Intermediate 6-6 and 2-bromo-4,6-diphenyl-1,3,5-triazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.85-8.78 (m, 4H), 8.65-8.63 (m, 1H), 8.43-8.41 (m, 1H), 8.28 (dd, 1H), 8.21-8.19 (m, 1H), 8.01-7.97 (m, 2H), 7.80-7.77 (m, 1H), 7.73 (d, 1H), 7.69-7.59 (m, 7H), 7.54-7.50 (m, 2H), 7.42-7.38 (m, 2H), 7.20-7.18 (m, 1H), 7.15-7.12 (m, 1H), 1.47 (s, 6H), 1.39 (s, 6H)

C$_{49}$H$_{37}$N$_3$: calc. 667.29. found 668.39.

Synthesis Example 26

Synthesis of Compound 45

Compound 45 was synthesized in the same manner as in Synthesis Example 1, except that phenanthren-9-yl-9-boronic acid was used instead of phenyl boronic acid (Compound A-6) in the synthesis of Intermediate 6-6 and 3-(3-bromo-5-(pyridin-3-yl)phenyl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.80-8.78 (m, 4H), 8.65-8.63 (m, 1H), 8.43-8.41 (m, 1H), 8.20 (d, 1H), 8.15 (d, 1H), 8.01-7.93 (m, 4H), 7.80-7.78 (m, 1H), 7.68-7.61 (m, 3H), 7.54-7.50 (m, 6H), 7.44 (dd, 1H), 7.38-7.36 (m, 1H), 7.22-7.20 (m, 1H), 7.15-7.12 (m, 1H), 1.39 (s, 6H), 1.37 (s, 6H)

C$_{50}$H$_{38}$N$_2$: calc. 666.30. found 667.31.

Synthesis Example 27

Synthesis of Compound 47

Compound 47 was synthesized in the same manner as in Synthesis Example 1, except that phenanthren-9-yl-9-boronic acid was used instead of phenyl boronic acid (Compound A-6) in the synthesis of Intermediate 6-6 and Compound B-47 below was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.65-8.63 (m, 1H), 8.48 (dd, 1H), 8.43-8.41 (m, 2H), 8.21-8.15 (m, 3H), 7.99 (dd, 1H), 7.94-7.89 (m, 4H), 7.80-7.77 (m, 1H), 7.68-7.61 (m, 3H), 7.54-7.50 (m, 2H), 7.43-7.40 (m, 2H), 7.22-7.20 (m, 1H), 7.15-7.12 (m, 1H), 6.81 (dd, 1H), 1.39 (s, 6H), 1.37 (s, 6H)

C$_{46}$H$_{39}$N$_3$: calc. 629.28. found 630.39.

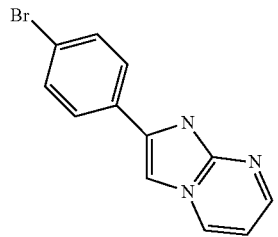

Compound B-47

Synthesis Example 28

Synthesis of Compound 50

Compound 50 was synthesized in the same manner as in Synthesis Example 1, except that phenanthren-9-yl-9-boronic acid was used instead of phenyl boronic acid (Compound A-6) in the synthesis of Intermediate 6-6 and 2-bromo-5-(3,5-difluorophenyl)pyridine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 9.02-9.00 (m, 1H), 8.65-8.63 (m, 1H), 8.43-8.41 (m, 1H), 8.36 (dd, 1H), 8.05-7.95 (m, 4H), 7.80-7.77 (m, 1H), 7.71-7.61 (m, 4H), 7.54-7.50 (m, 3H), 7.21-7.12 (m, 4H), 6.72-6.67 (m, 1H), 1.42 (s, 6H), 1.39 (s, 6H)

C$_{45}$H$_{33}$NF$_3$: calc. 625.25. found 626.35.

Synthesis Example 29

Synthesis of Compound 52

Compound 52 was synthesized in the same manner as in Synthesis Example 1, except that 1,10-phenanthrolin-2-yl-2-boronic acid was used instead of phenyl boronic acid (Compound A-6) in the synthesis of Intermediate 6-6 and 3-bromoquinoline was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 9.19 (dd, 1H), 9.06-9.04 (m, 1H), 8.59-8.57 (m, 1H), 8.49 (dd, 1H), 8.35-8.28 (m, 3H), 8.20-8.14 (m, 2H), 8.09-8.05 (m, 2H), 7.84-7.76 (m, 3H), 7.72-7.66 (m, 2H), 7.60-7.57 (m, 1H), 7.52-7.48 (m, 1H), 7.36 (s, 1H), 1.42 (s, 6H), 1.37 (s, 6H)

C$_{41}$H$_{31}$N$_3$: calc. 565.25. found 566.36.

Synthesis Example 30

Synthesis of Compound 55

Compound 55 was synthesized in the same manner as in Synthesis Example 1, except that 1,10-phenanthrolin-2-yl-2-boronic acid was used instead of phenyl boronic acid (Compound A-6) in the synthesis of Intermediate 6-6 and Compound B-55 below was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 9.19 (dd, 1H), 8.50 (dd, 1H), 8.33-8.26 (m, 2H), 8.20-8.09 (m, 3H), 7.83-7.78 (m, 4H), 7.74-7.66 (m, 6H), 7.59 (dd, 1H), 7.49-7.37 (m, 8H), 1.42 (s, 6H), 1.37 (s, 6H)

C$_{50}$H$_{38}$N$_2$: calc. 666.30. found 667.41.

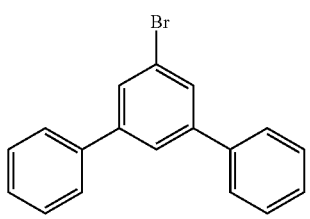

Compound B-55

Synthesis Example 31

Synthesis of Compound 56

Compound 56 was synthesized in the same manner as in Synthesis Example 1, except that 1,10-phenanthrolin-2-yl-2-boronic acid was used instead of phenyl boronic acid (Compound A-6) in the synthesis of Intermediate 6-6. The synthesized compound was confirmed by $^1$H NMR and MS/FAB.

$^1$H NMR (CDCl$_3$, 400 MHz) □ δ: 9.19 (dd, 1H), 8.50 (dd, 1H), 8.33-8.26 (m, 2H), 8.20-8.18 (m, 1H), 8.10-8.03 (m, 3H), 7.90-7.88 (m, 1H), 7.83-7.55 (m, 10H), 7.45-7.37 (m, 5H), 7.33-7.20 (m, 2H), 1.43 (s, 6H), 1.40 (s, 6H)

C$_{51}$H$_{38}$N$_4$: calc. 706.30. found 707.31.

Synthesis Example 32

Synthesis of Compound 58

Compound 58 was synthesized in the same manner as in Synthesis Example 1, except that 3,5-difluorophenylboronic acid was used instead of phenyl boronic acid (Compound A-6) in the synthesis of Intermediate 6-6 and 2-bromo-4,6-diphenyl-1,3,5-triazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.81-8.78 (m, 4H), 8.33-8.27 (m, 2H), 7.97-7.95 (m, 1H), 7.73 (d, 1H), 7.63-7.59 (m, 4H), 7.48-7.40 (m, 3H), 7.35-7.33 (m, 1H), 7.14-7.07 (m, 2H), 6.67-6.62 (m, 1H), 1.47 (s, 6H), 1.37 (s, 6H)

C$_{41}$H$_{31}$N$_3$F$_2$: calc. 603.24. found 604.35.

Synthesis Example 33

Synthesis of Compound 63

Compound 63 was synthesized in the same manner as in Synthesis Example 1, except that iodobenzene was used instead of iodomethane in the synthesis of Intermediate 4-6 and 2-bromopyrazine was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) □ δ: 9.02-9.00 (m, 1H), 8.56-8.55 (m, 1H), 8.46-8.42 (m, 2H), 8.05-8.01 (m, 2H), 7.82 (d, 1H), 7.75-7.72 (m, 1H), 7.61-7.59 (m, 1H), 7.52-7.48 (m, 2H), 7.42-7.40 (m, 1H), 7.35-7.33 (m, 1H), 7.19-7.10 (m, 12H), 7.05-6.97 (m, 9H)

C$_{50}$H$_{59}$N$_2$: calc. 662.27. found 663.37.

Synthesis Example 34

Synthesis of Compound 65

Compound 65 was synthesized according to Reaction Scheme 2 below:

Reaction Scheme 2

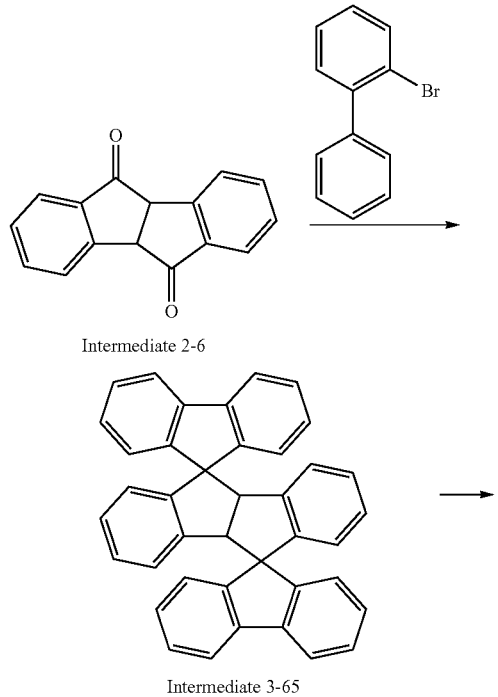

Intermediate 2-6

Intermediate 3-65

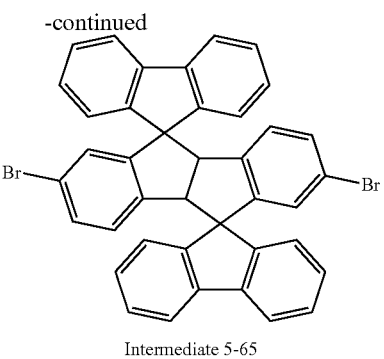

Intermediate 5-65

Compound 65

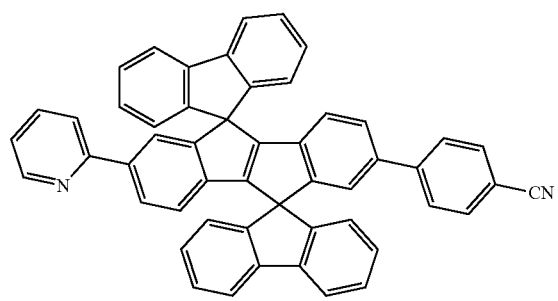

Synthesis of Intermediate 3-65

5.00 g (21.4 mmol) of 2-bromobiphenyl was dissolved in 11.0 ml of THF and 0.57 g (23.3 mmol) of magnesium was added thereto at room temperature. When a Grenia product was produced therefrom, a solution prepared by dissolving 5.06 g (21.4 mmol) of Intermediate 2-6 in 5 ml of THF was added to the resulting solution, the resultant solution was stirred at 85° C. for 4 hours, and the temperature thereof was cooled down to room temperature to obtain a yellow precipitate. The yellow precipitate was washed with methanol to obtain 6.83 g of Intermediate 3-65 (yield: 63%). The synthesized compound was confirmed by MS/FAB.

$C_{40}H_{26}$: calc. 506.20. found 507.30.

Synthesis of Intermediate 5-65

Intermediate 5-65 was synthesized in the same manner as Synthesis of Intermediate 5-6 in Synthesis Example 1, except that Intermediate 3-65 was used instead of Intermediate 4-6.

Synthesis of Compound 65

Compound 65 was synthesized in the same manner as in Synthesis Example 1, except that pyridine boronic acid was used instead of phenyl boronic acid (Compound A-6) in the synthesis of Intermediate 6-6, Intermediate 5-65 was used instead of Intermediate 5-6, and benzonitrile was used instead of 2-(4-bromophenyl)-1-phenyl-1-benzoimidazole (Compound B-6) in the synthesis of Compound 6. The synthesized compound was confirmed by $^1$H NMR and MS/FAB.

$^1$H NMR (CDCl$_3$, 400 MHz) δ: 8.68-8.66 (m, 1H), 8.29-8.27 (m, 1H), 8.19 (dd, 1H), 8.00 (d, 2H), 7.83-7.72 (m, 7H), 7.67-7.60 (m, 4H), 7.49-7.47 (m, 1H), 7.36-7.32 (m, 4H), 7.18-7.15 (m, 1H), 7.05-7.01 (m, 4H), 6.53-6.50 (m, 4H)

$C_{52}H_{30}N_2$: calc. 682.24. found 683.34.

Synthesis Example 35

Synthesis of Compound 68

Compound 68 was synthesized in the same manner as in Synthesis Example 1, except that iodoethane was used instead of iodomethane in the synthesis of Intermediate 4-6. The synthesized compound was confirmed by $^1$H NMR and MS/FAB.

$^1$H NMR (CDCl$_3$, 400 MHz) δ: 8.27-8.24 (m, 2H), 8.07-8.03 (m, 2H), 7.96 (d, 1H), 7.91 (d, 1H), 7.80-7.74 (m, 3H), 7.68-7.64 (m, 3H), 7.58-7.55 (m, 2H), 7.51-7.47 (m, 2H), 7.44-7.35 (m, 6H), 7.32-7.28 (m, 1H), 7.25-7.20 (m, 1H), 1.81-1.72 (m, 4H), 1.58-1.53 (m, 4H), 0.79-0.74 (m, 12H)

$C_{49}H_{44}N_2$: calc. 660.35. found 661.46.

Example 1

As an anode, a 15 Ω/cm2 (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was mounted on a vacuum depositor.

2-TNATA was deposited on the ITO glass substrate to form a HIL having a thickness of 600 Å and 4,4'-bis[N-(1-naphthyl)-N-phenylamino]biphenyl (NPB) was then deposited on the HIL to form a HTL having a thickness of 300 Å.

Next, 9,10-di-naphthalene-2-yl-anthracene (ADN) as host and DPVBi as a dopant were co-deposited on the HTL at a weight ratio of 98:2 to form an EML having a thickness of 300 Å.

Thereafter, Compound 6 was deposited on the EML to form an ETL having a thickness of 300 Å, LiF was deposited on the ETL to form an EIL having a thickness of 10 Å, and Al was deposited on the EIL to form a second electrode (cathode) having a thickness of 3,000 Å, thereby completing the manufacture of an OLED.

Example 2

An OLED was manufactured in the same manner as in Example 1, except that Compound 15 was used instead of Compound 6 in the formation of the ETL.

Example 3

An OLED was manufactured in the same manner as in Example 1, except that Compound 28 was used instead of Compound 6 in the formation of the ETL.

Example 4

An OLED was manufactured in the same manner as in Example 1, except that Compound 41 was used instead of Compound 6 in the formation of the ETL.

Example 5

An OLED was manufactured in the same manner as in Example 1, except that Compound 49 was used instead of Compound 6 in the formation of the ETL.

Example 6

An OLED was manufactured in the same manner as in Example 1, except that Compound 57 was used instead of Compound 6 in the formation of the ETL.

Comparative Example 1

An OLED was manufactured in the same manner as in Example 1, except that Alq3 was used instead of Compound 6 in the formation of the ETL.

Comparative Example 2

An OLED was manufactured in the same manner as in Example 1, except that Compound E1 below was used instead of Compound 6 in the formation of the ETL.

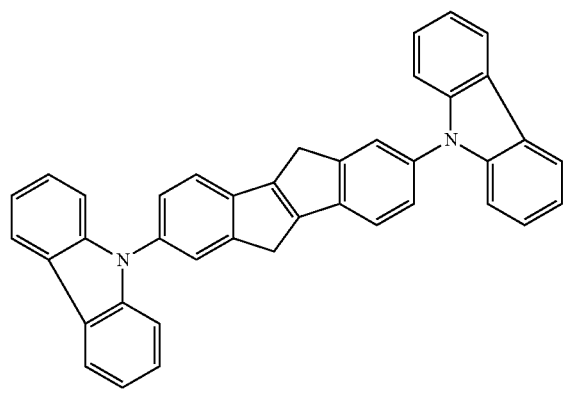

Compound E1

Comparative Example 3

An OLED was manufactured in the same manner as in Example 1, except that Compound E2 below was used instead of Compound 6 in the formation of the ETL.

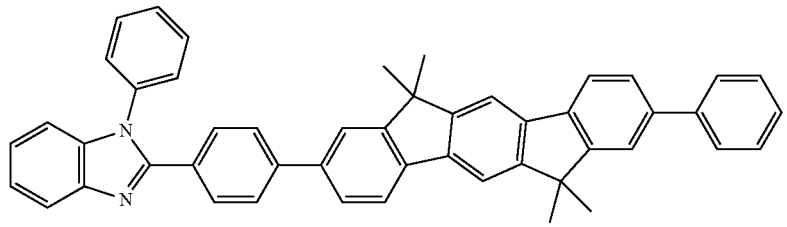

Compound E2

Evaluation Example 1

Driving voltage, current density, brightness, emission color, efficiency, and half lifetime (@100 mA/cm$^2$) of each of the OLEDs of Examples 1 through 6 and Comparative Examples 1 through 3 were evaluated using PR650 Spectroscan Source Measurement Unit (available from PhotoResearch), and the results are shown in Table 1 below.

TABLE 1

| | ETL | Driving voltage (V) | Current density (mA/cm$^2$) | Brightness (cd/m$^2$) | Efficiency (cd/A) | Emission color | Half lifetime (hr) |
|---|---|---|---|---|---|---|---|
| Example 1 | Compound 6 | 5.27 | 50 | 2,254 | 4.50 | blue | 293 |
| Example 2 | Compound 15 | 5.53 | 50 | 2,257 | 4.51 | blue | 245 |
| Example 3 | Compound 28 | 5.22 | 50 | 2,430 | 4.86 | blue | 224 |
| Example 4 | Compound 41 | 5.24 | 50 | 2,108 | 4.21 | blue | 285 |
| Example 5 | Compound 49 | 5.48 | 50 | 2,260 | 4.52 | blue | 251 |
| Example 6 | Compound 57 | 5.32 | 50 | 2,221 | 4.44 | blue | 298 |
| Comparative Example 1 | Alq3 | 7.85 | 50 | 1,560 | 3.12 | blue | 113 |
| Comparative Example 2 | Compound E1 | 7.35 | 50 | 1,680 | 3.36 | blue | 125 |
| Comparative Example 3 | Compound E2 | 6.15 | 50 | 1,870 | 3.74 | blue | 156 |

From the results shown in Table 1, it is confirmed that the OLEDs of Examples 1 through 6 have higher driving voltage, higher brightness, higher efficiency, higher color purity, and longer lifetime than the OLEDs of Comparative Examples 1 through 3.

As described above, according to the one or more embodiments, an OLED including the condensed-cyclic compound may have a low driving voltage, high brightness, high efficiency, and long lifetime.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:

1. An organic light-emitting diode comprising: a first electrode; a second electrode facing the first electrode; and an organic layer interposed between the first electrode and the second electrode, wherein the organic layer comprises an emission layer and an electron transport layer and the electron transport layer comprises at least one compound represented by Formula 1 below:

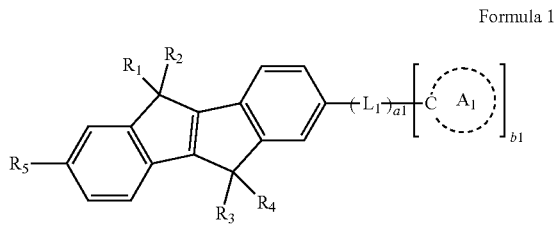

Formula 1 wherein A1 is a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted isoquinolinyl group, a substituted or unsubstituted phenanthrolinyl group, a substituted or unsubstituted benzothiazolyl group, or a substituted or unsubstituted benzooxazolyl group;

$L_1$ is a substituted or unsubstituted $C_6$-$C_{60}$ arylene group or a substituted or unsubstituted $C_2$-$C_{60}$ heteroarylene group;

a1 is an integer of 0 to 5;

b1 is an integer of 1 to 5; and $R_1$ through $R_5$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

2. The organic light-emitting diode of claim 1, wherein A1 is one of Formulae 3A through 3O below:

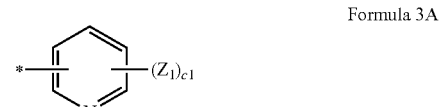

Formula 3A

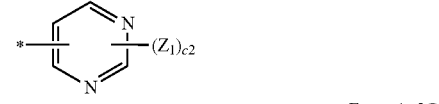

Formula 3B

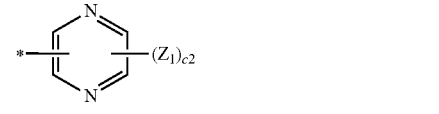

Formula 3C

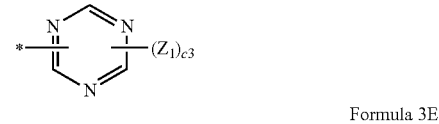

Formula 3D

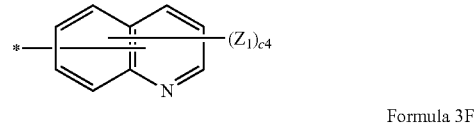

Formula 3E

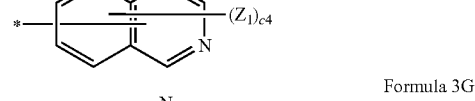

Formula 3F

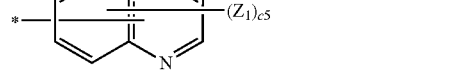

Formula 3G

-continued

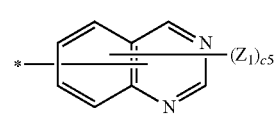
Formula 3H

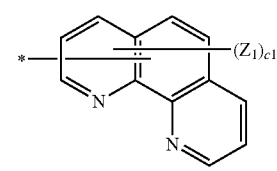
Formula 3I

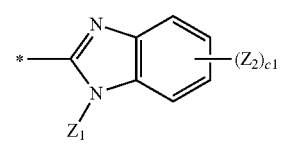
Formula 3J

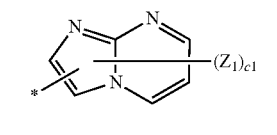
Formula 3K

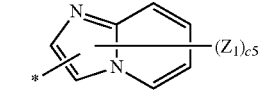
Formula 3L

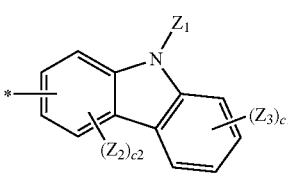
Formula 3M

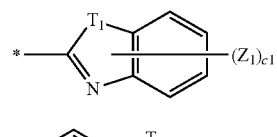
Formula 3N

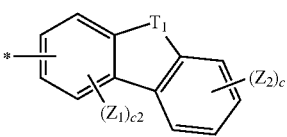
Formula 3O

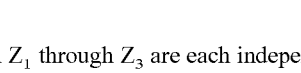

wherein $Z_1$ through $Z_3$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_3$-$C_{60}$ cycloalkenyl group, a $C_6$-$C_{60}$ aryl group, a $C_6$-$C_{60}$ aryl group that is substituted with at least one of —F, —CN, and a $C_1$-$C_{10}$ alkyl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

c1 is an integer of 1 to 4;
c2 is an integer of 1 to 3;
c3 is an integer of 1 to 2;
c4 is an integer of 1 to 6;
c5 is an integer of 1 to 5; and
$T_1$ is O or S.

3. The organic light-emitting diode of claim 1, wherein $A_1$ is one of Formulae 4A through 4R below:

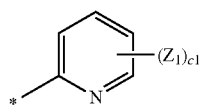
Formula 4A

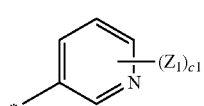
Formula 4B

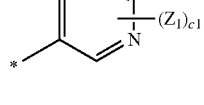
Formula 4C

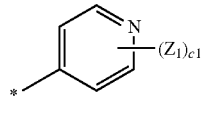
Formula 4D

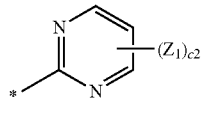
Formula 4E

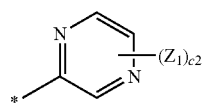
Formula 4F

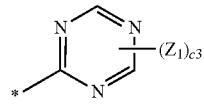
Formula 4G

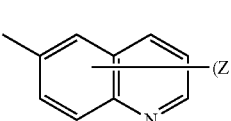
Formula 4H

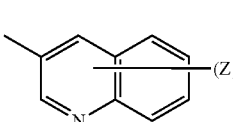
Formula 4I

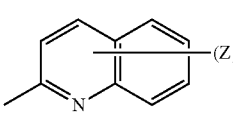
Formula 4J

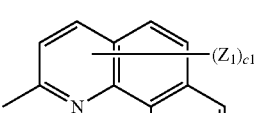
Formula 4K

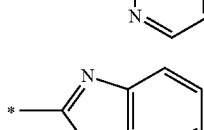
Formula 4L

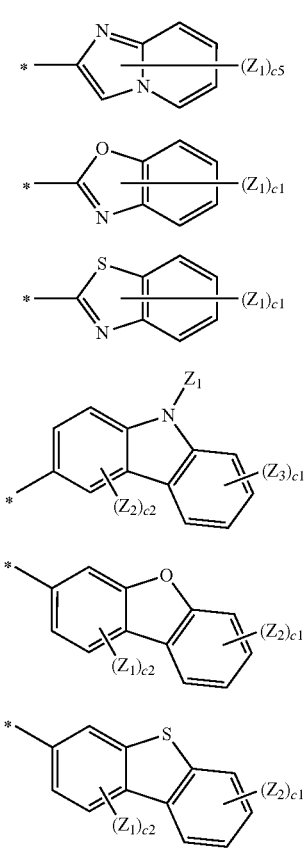

Formula 4M
Formula 4N
Formula 4O
Formula 4P
Formula 4Q
Formula 4R wherein $Z_1$ through $Z_3$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, a phenyl group, a naphthyl group, an anthryl group, a fluorenyl group, a pyrenyl group, a phenyl group that is substituted with at least one of —F, —CN, and a $C_1$-$C_{10}$ alkyl group, a naphthyl group that is substituted with at least one of —F, —CN, and a $C_1$-$C_{10}$ alkyl group, an anthryl group that is substituted with at least one of —F, —CN, and a $C_1$-$C_{10}$ alkyl group, a fluorenyl group that is substituted with at least one of —F, —CN, and a $C_1$-$C_{10}$ alkyl group, a pyrenyl group that is substituted with at least one of —F, —CN, and a $C_1$-$C_{10}$ alkyl group, a pyridinyl group, a dibenzothiophenyl group, or a dibenzofuranyl group; and c1 through c5 are 1 or 2.

4. The organic light-emitting diode of claim 3, wherein $Z_1$ through $Z_3$ are each independently hydrogen, a phenyl group, a naphthyl group, an anthryl group, a fluorenyl group, a pyrenyl group, a phenyl group that is substituted with at least one of —F, —CN, and a $C_1$-$C_{10}$ alkyl group, a naphthyl group that is substituted with at least one of —F, —CN, and a $C_1$-$C_{10}$ alkyl group, an anthryl group that is substituted with at least one of —F, —CN, and a $C_1$-$C_{10}$ alkyl group, a fluorenyl group that is substituted with at least one of —F, —CN, and a $C_1$-$C_{10}$ alkyl group, a pyrenyl group that is substituted with at least one of —F, —CN, and a $C_1$-$C_{10}$ alkyl group, a pyridinyl group, a dibenzothiophenyl group, or a dibenzofuranyl group.

5. The organic light-emitting diode of claim 1, wherein $L_1$ is a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene, a substituted or unsubstituted isoindolylene group, a substituted or unsubstituted indolylene group, a substituted or unsubstituted indazolylene group, a substituted or unsubstituted purinylene group, a substituted or unsubstituted quinolinylene group, a substituted or unsubstituted benzoquinolinylene group, a substituted or unsubstituted phthalazinylene group, a substituted or unsubstituted naphthyridinylene group, a substituted or unsubstituted quinoxalinylene group, a substituted or unsubstituted quinazolinylene group, a substituted or unsubstituted cinnolinylene group, a substituted or unsubstituted carbazolylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzooxazolylene group, a substituted or unsubstituted benzoimidazolylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted thiazolylene group, a substituted or unsubstituted isothiazolylene group, a substituted or unsubstituted benzothiazolylene group, a substituted or unsubstituted isoxazolylene group, a substituted or unsubstituted oxazolylene group, a substituted or unsubstituted triazolylene group, a substituted or unsubstituted tetrazolylene group, a substituted or unsubstituted oxadiazolylene group, a substituted or unsubstituted triazinylene group, a substituted or unsubstituted benzooxazolylene group, a substituted or unsubstituted dibenzofuranylene group, a substituted or unsubstituted dibenzothiophenylene, or a substituted or unsubstituted benzocarbazolylene group.

6. The organic light-emitting diode of claim 1, wherein $L_1$ is one of Formulae 5A through 5M below:

Formula 5A

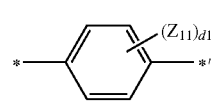

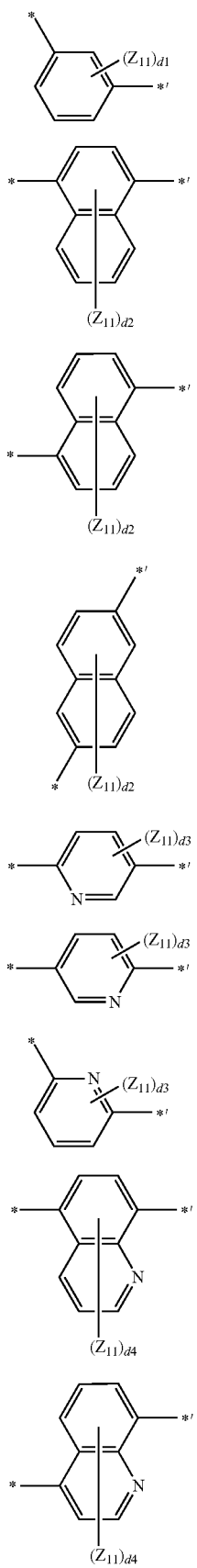

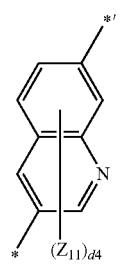

wherein $Z_{11}$ and $Z_{12}$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_3$-$C_{60}$ cycloalkenyl group, a $C_6$-$C_{60}$ aryl group, a $C_6$-$C_{60}$ aryl group that is substituted with at least one of —F, —CN, and a $C_1$-$C_{10}$ alkyl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

d1 is an integer of 1 to 4;
d2 is an integer of 1 to 6;
d3 is an integer of 1 to 3;
d4 is an integer of 1 to 5;
*' denotes a binding side with $A_1$.

7. The organic light-emitting diode of claim 6, wherein $Z_{11}$ and $Z_{12}$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, a phenyl group, a naphthyl group, an anthryl group, a fluorenyl group, a pyrenyl group, a phenyl group that is substituted with at least one of —F, —CN, and a $C_1$-$C_{10}$ alkyl group, a naphthyl group that is substituted with at least one of —F, —CN, and a $C_1$-$C_{10}$ alkyl group, an anthryl group that is substituted with at least one of —F, —CN, and a $C_1$-$C_{10}$ alkyl group, a fluorenyl group that is substituted with at least one of —F, —CN, and a $C_1$-$C_{10}$ alkyl group, a pyrenyl group that is substituted with at least one of —F, —CN, and a $C_1$-$C_{10}$ alkyl group, a pyridinyl group, a dibenzothiophenyl group, or a dibenzofuranyl group.

8. The organic light-emitting diode of claim 1, wherein a1 is 0 or 1; and b1 is 1 or 2.

9. The organic light-emitting diode of claim 1, wherein $R_1$ through $R_4$ are each independently a methyl group, an ethyl group, a propyl group, a butyl group, a pentyl group, a phenyl group, a naphthyl group, an anthryl group, or a fluorenyl group.

10. The organic light-emitting diode of claim 1, wherein $R_1$ through $R_4$ are identical.

11. A compound represented by Formula 1 below:

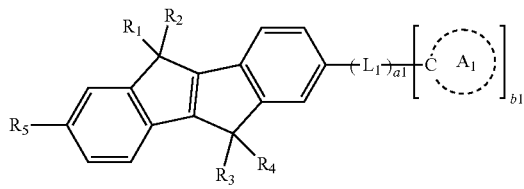

Formula 1 wherein A1 is a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted isoquinolinyl group, a substituted or unsubstituted phenanthrolinyl group, a substituted or unsubstituted benzothiazolyl group, or a substituted or unsubstituted benzooxazolyl group;

L1 is a substituted or unsubstituted C6-C60 arylene group or a substituted or unsubstituted C2-C60 heteroarylene group;

a1 is an integer of 0 to 5;

b1 is an integer of 1 to 5; and

R1 through R5 are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C60 cycloalkyl group, a substituted or unsubstituted C3-C60 cycloalkenyl group, a substituted or unsubstituted C6-C60 aryl group, a substituted or unsubstituted C6-C60 aryloxy group, a substituted or unsubstituted C6-C60 arylthio group, or a substituted or unsubstituted C2-C60 heteroaryl group, wherein $R_1$ and $R_2$ are linked to each other by a single bond, and $R_3$ and $R_4$ are linked to each other by a single bond.

12. The organic light-emitting diode of claim 1, wherein the compound is represented by Formula 1A or 1B:

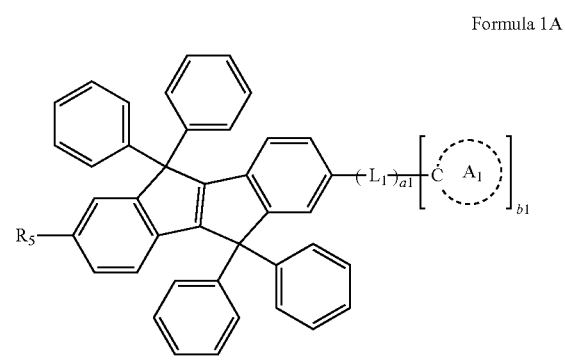

Formula 1A

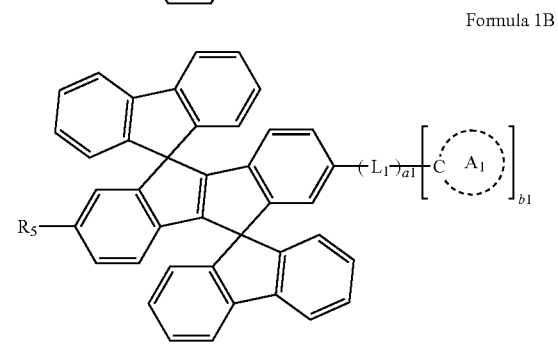

Formula 1B wherein $L_1$, $a_1$, $b_1$, $A_1$ ring, and $R_5$ are the same as defined in claim 1.

13. The organic light-emitting diode of claim 1, wherein $R_5$ is a substituted or unsubstituted phenyl group, a substituted or unsubstituted pentalenyl group, a substituted or unsubstituted indenyl group, a substituted or unsubstituted naphtyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted isoquinolinyl group, a substituted or unsubstituted phenanthrolinyl group, a substituted or unsubstituted benzothiazolyl group, or a substituted or unsubstituted benzooxazolyl group.

14. A compound of Compounds 1 through 74 below:

1

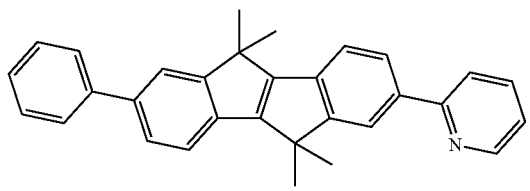

2

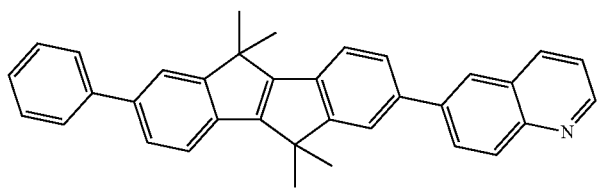

3

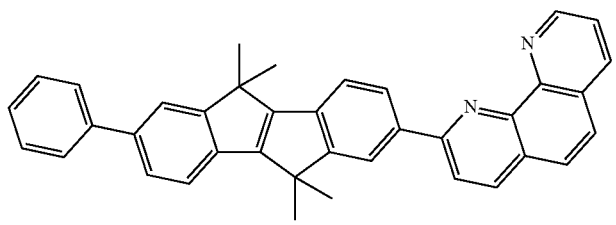

4

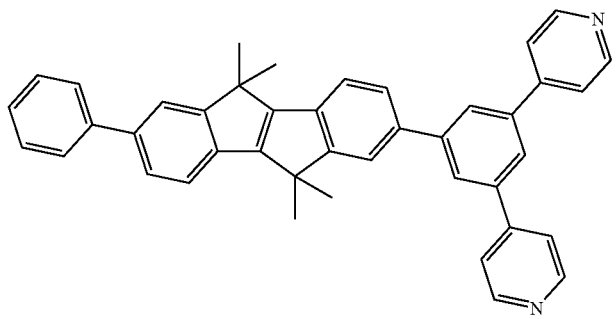

-continued
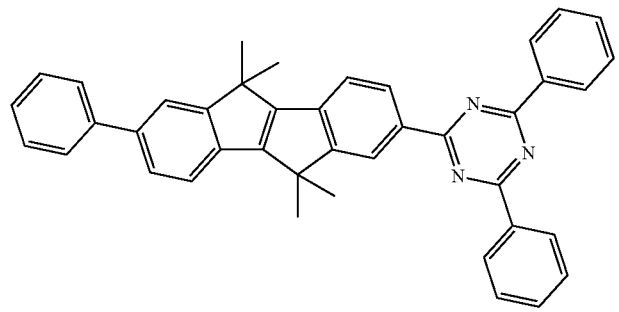
5
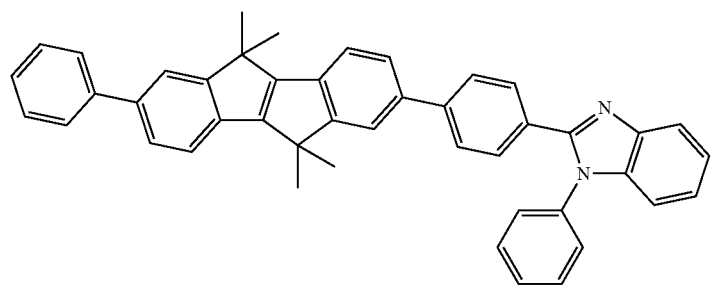
6
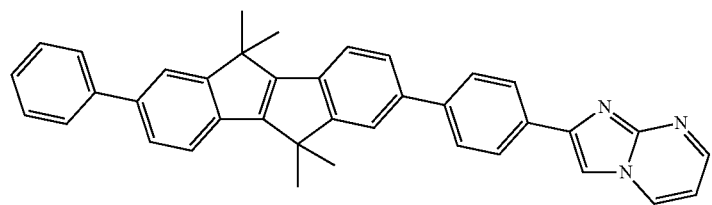
7
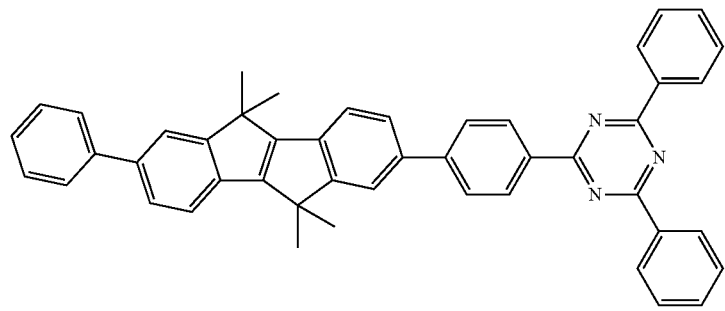
8
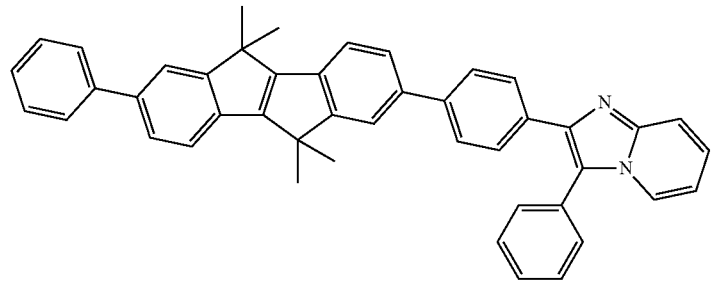
9

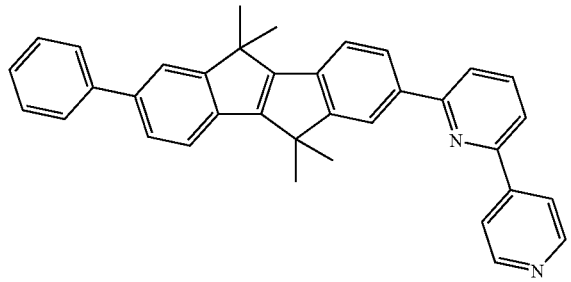
10
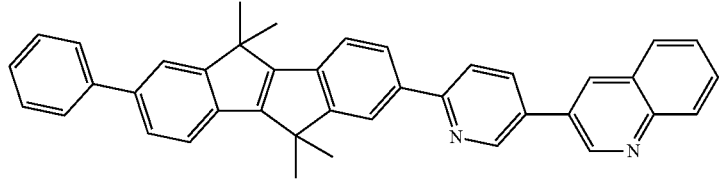
11
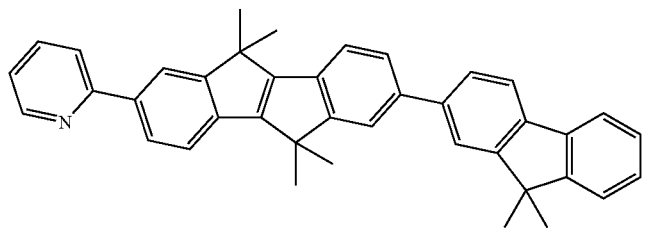
12
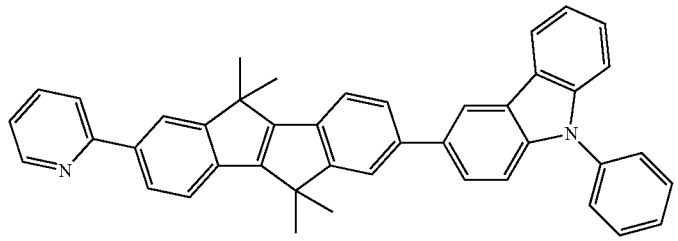
13
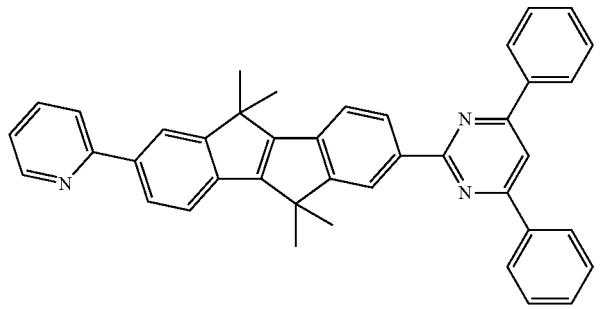
14
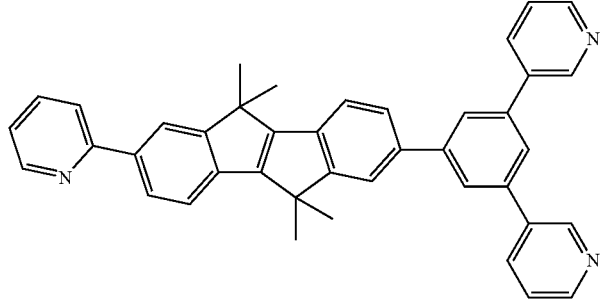
15

16
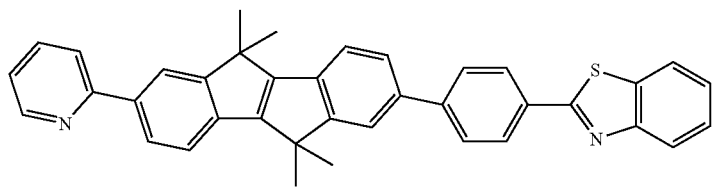
17
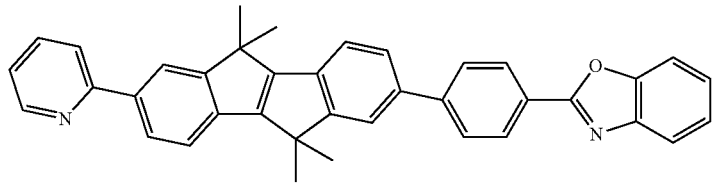
18
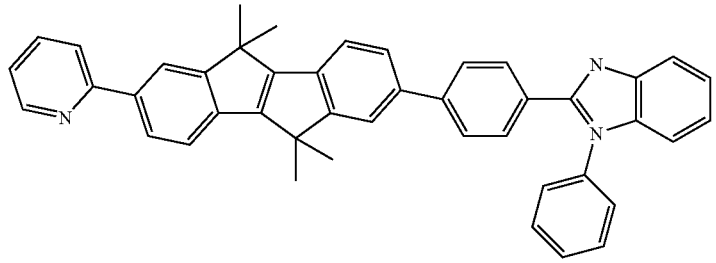
19
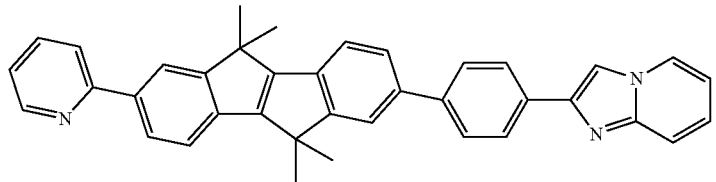
20
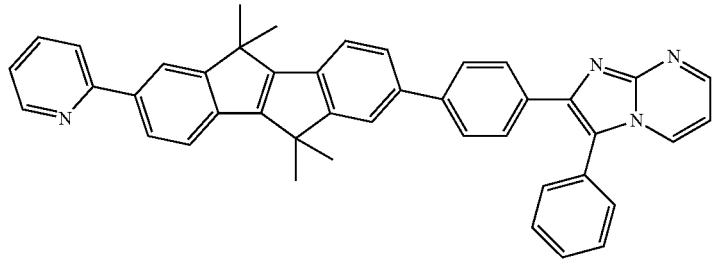
21
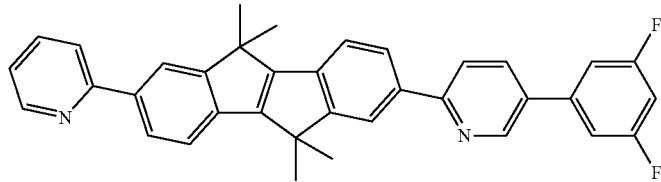
22
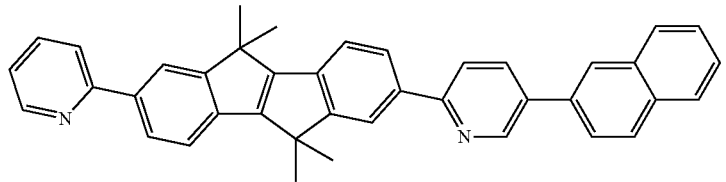

23
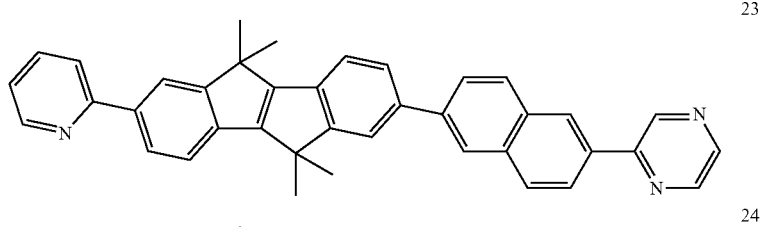
24
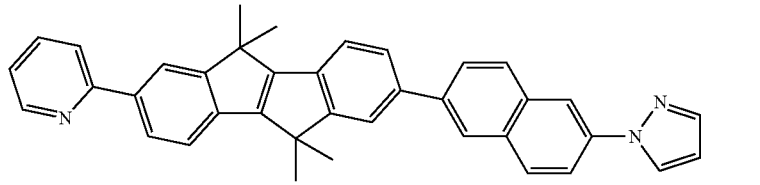
25
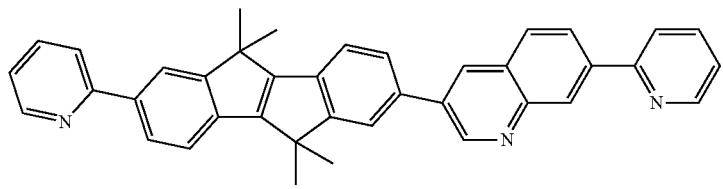
26
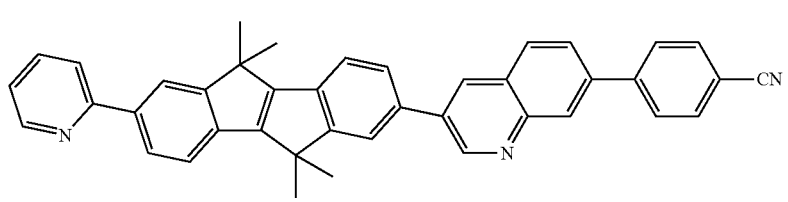
27
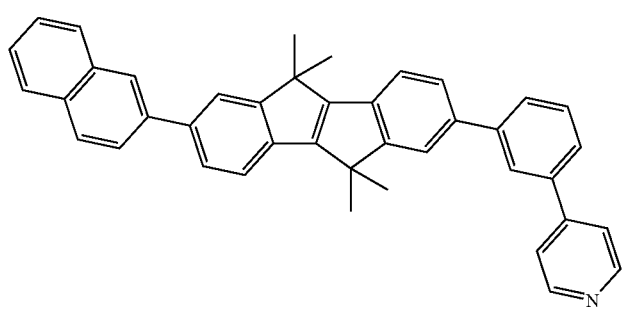
28
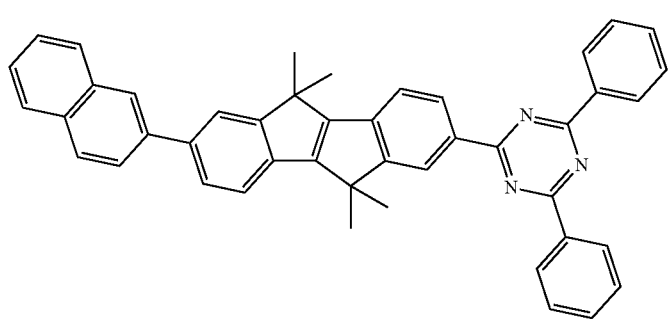
29
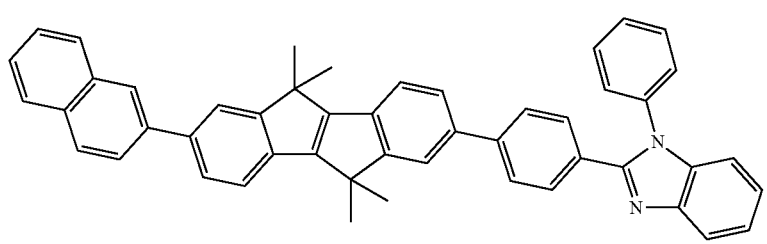

30
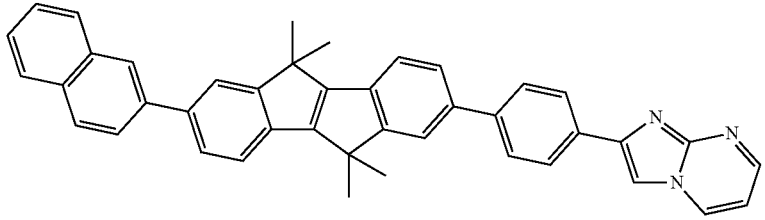
31
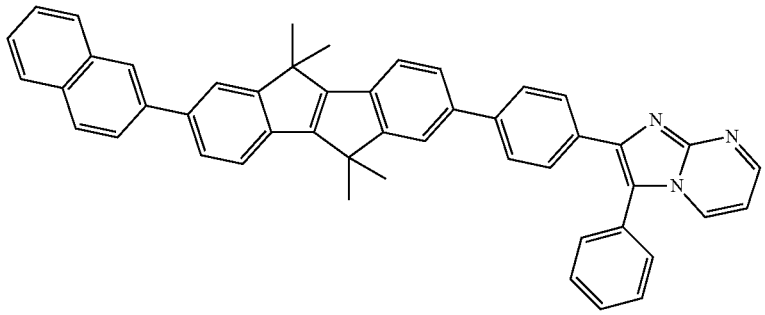
32
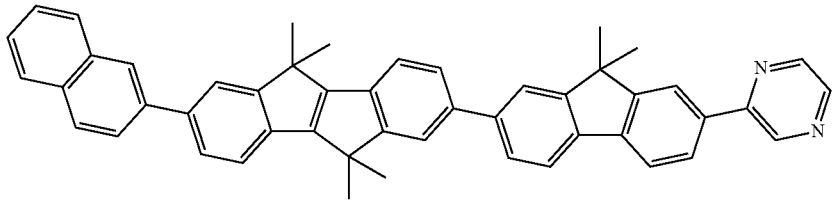
33
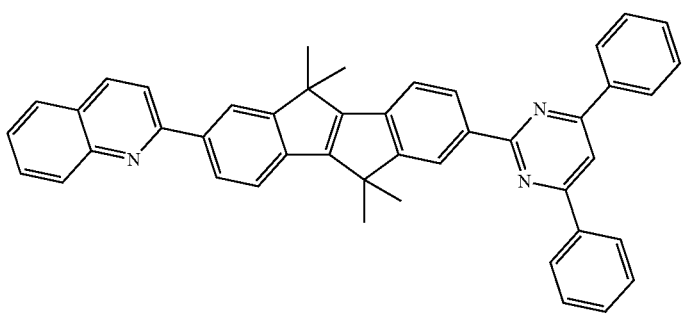
34
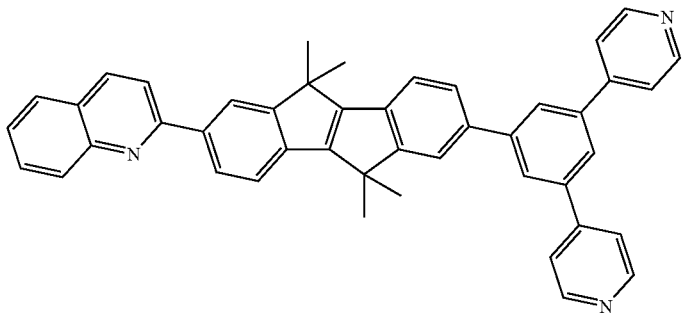

35
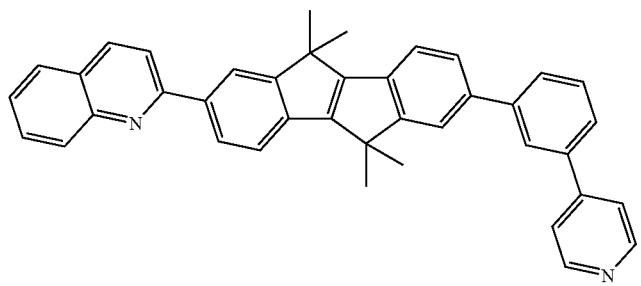
36
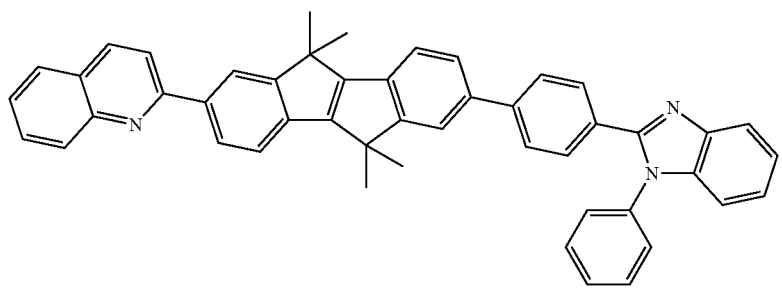
37
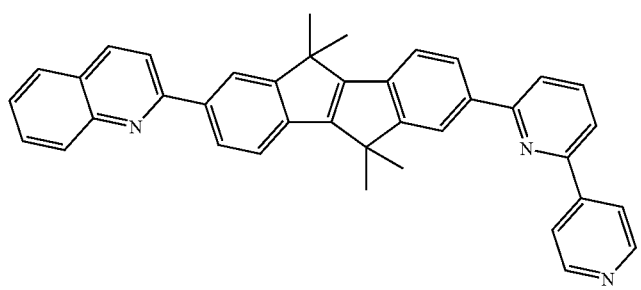
38
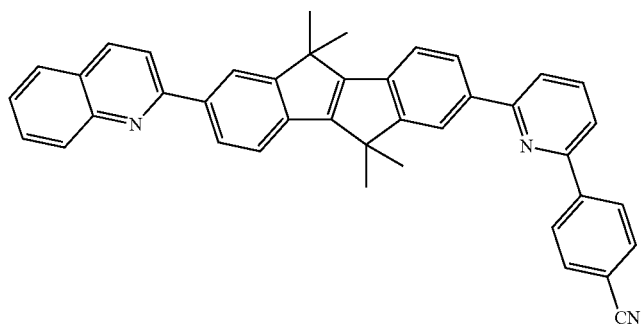
39
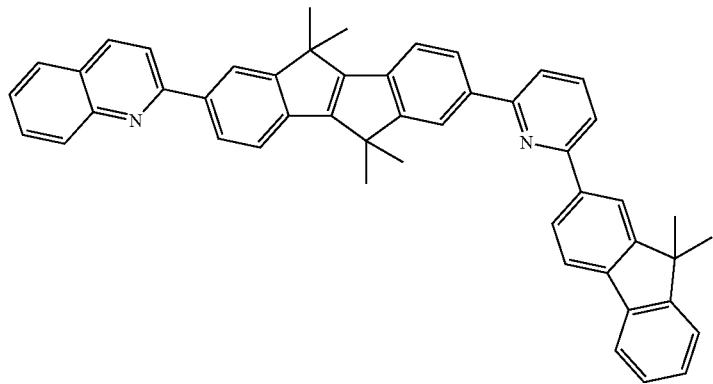

40
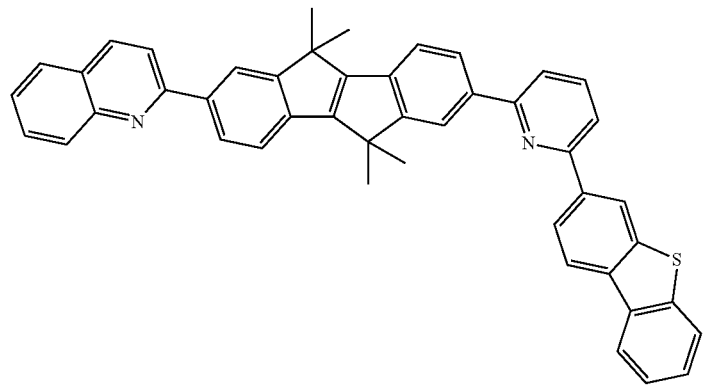
41
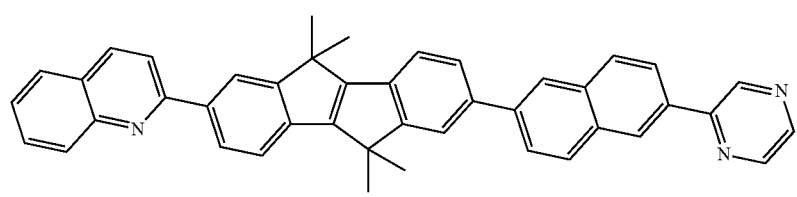
42
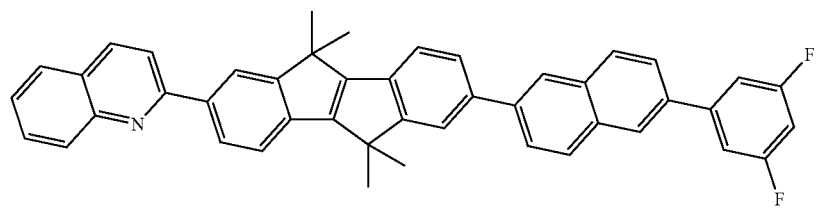
43
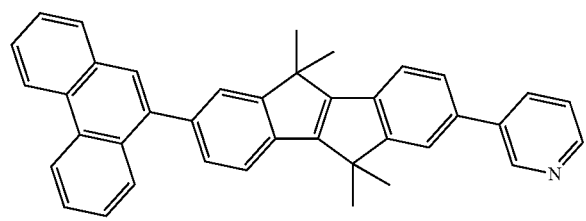
44
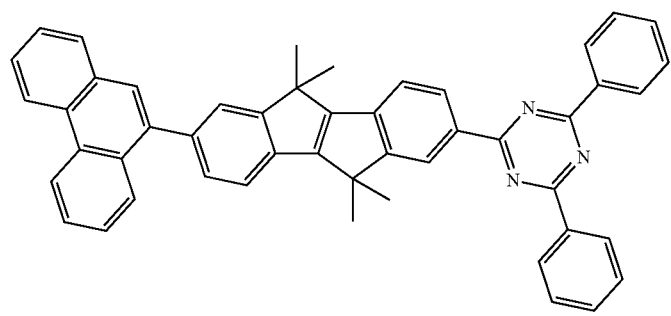

45
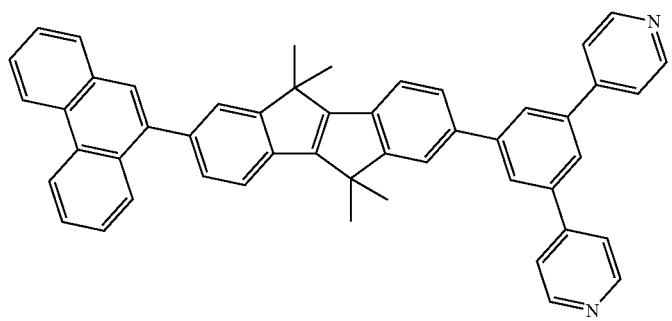
46
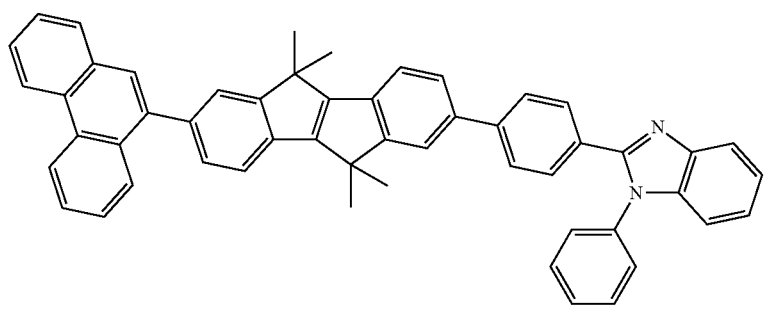
47
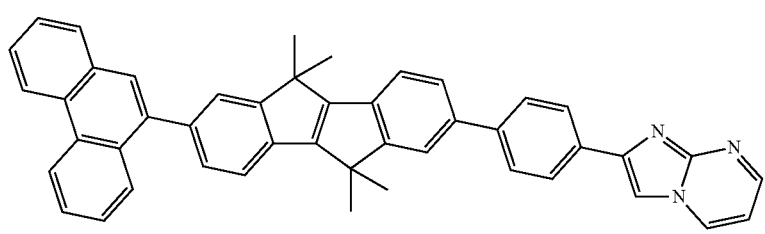
48
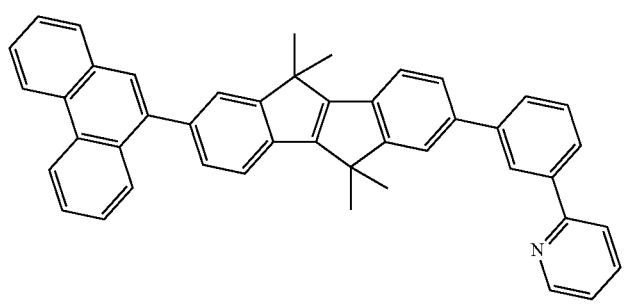
49
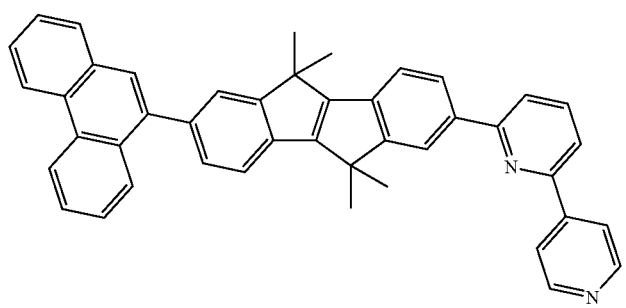

50
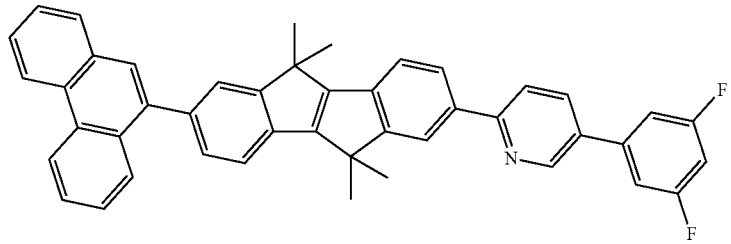
51
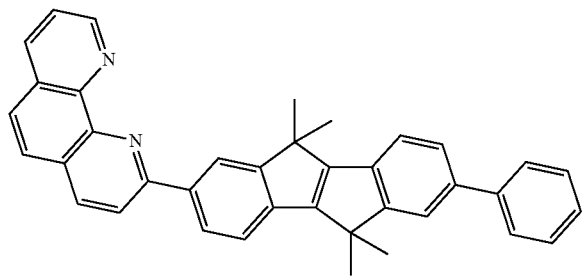
52
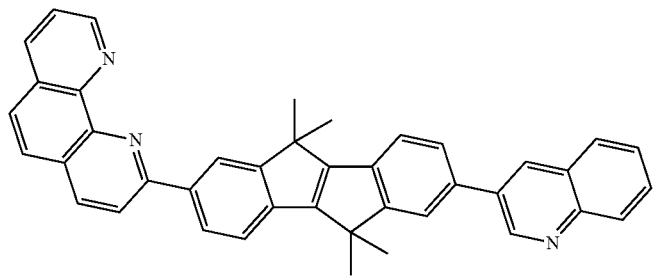
53
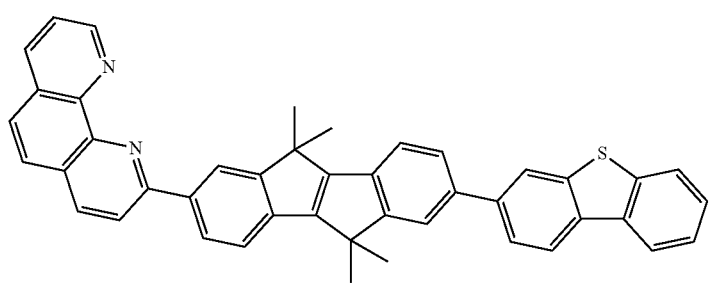
54
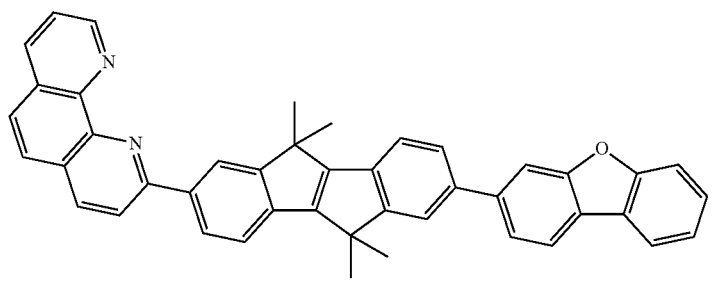

-continued
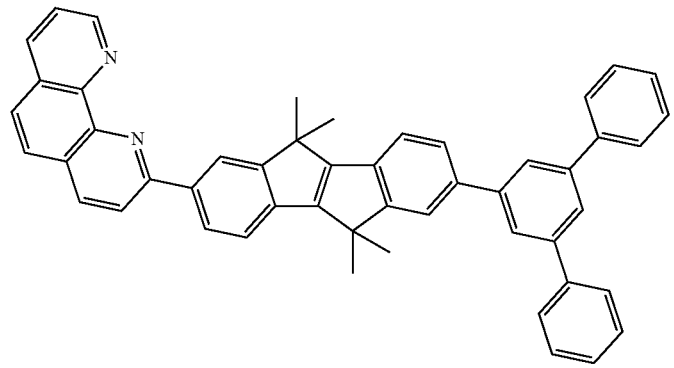
55
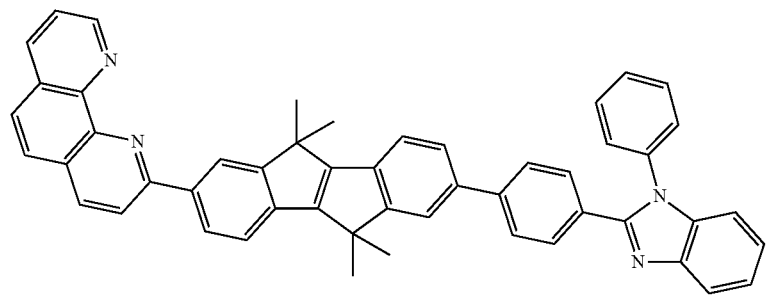
56
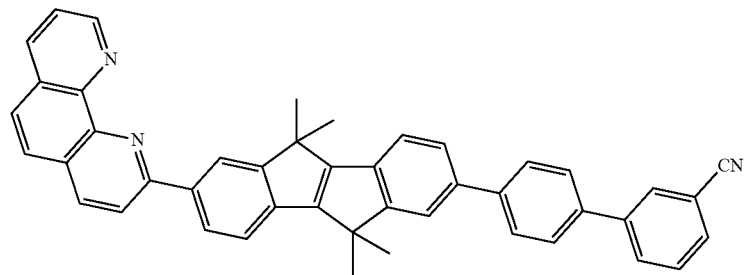
57
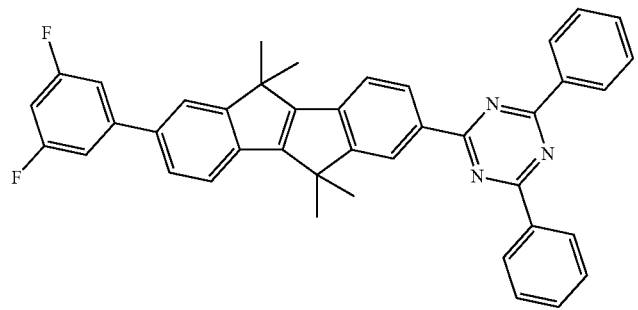
58
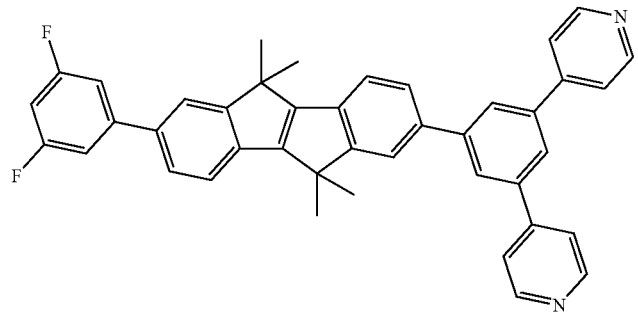
59

60
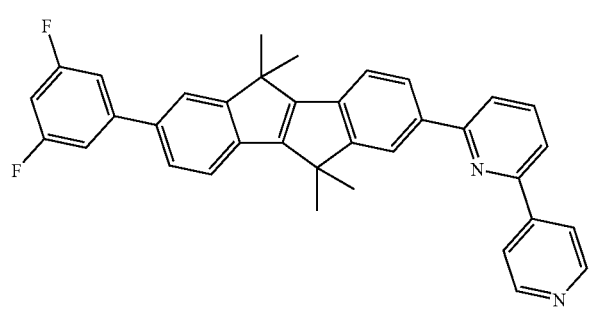
61
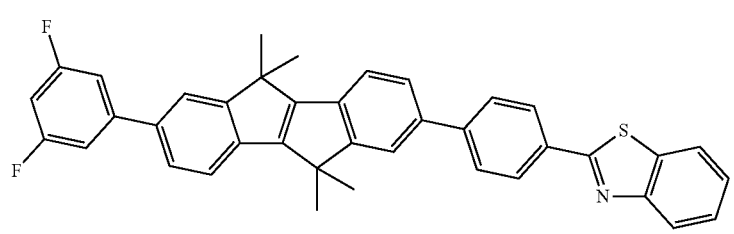
62
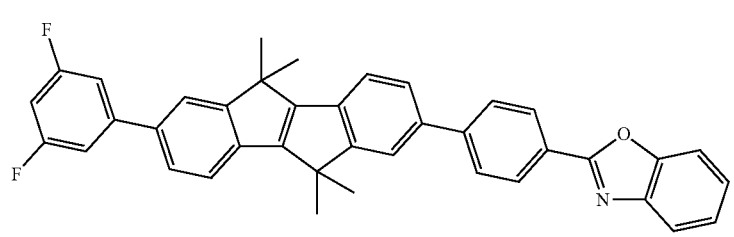
63
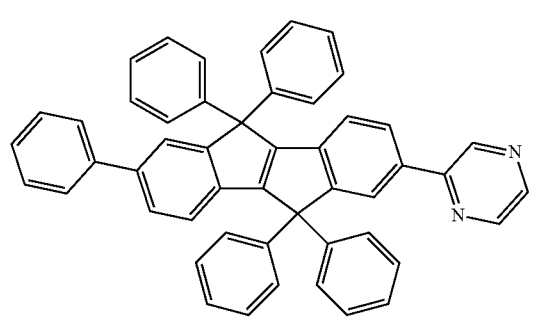
64
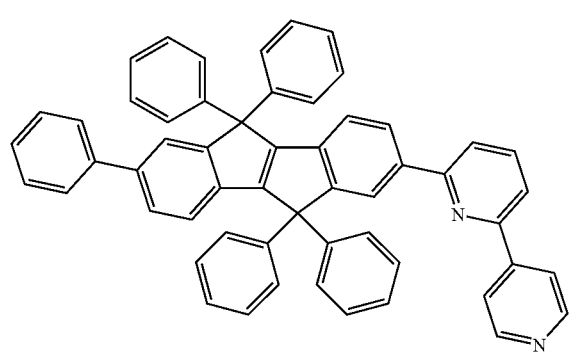

65
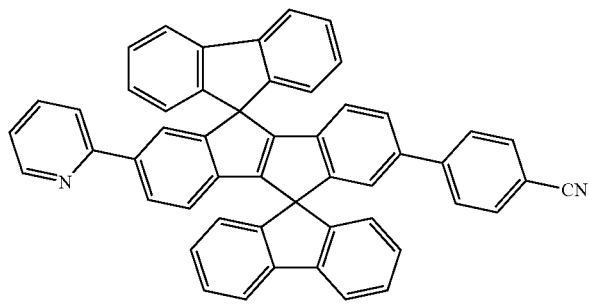
66
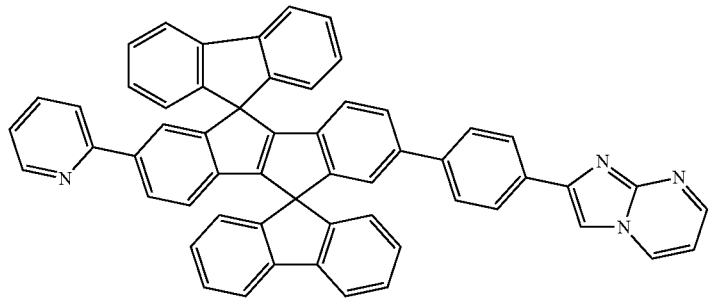
67
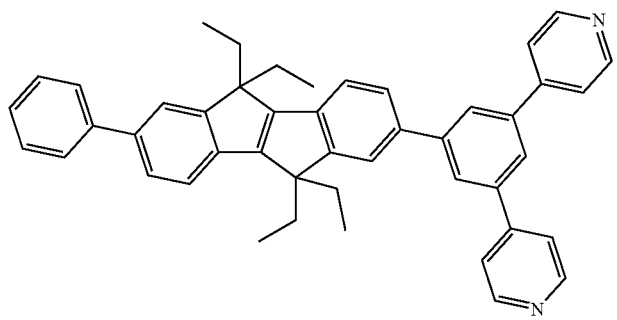
68
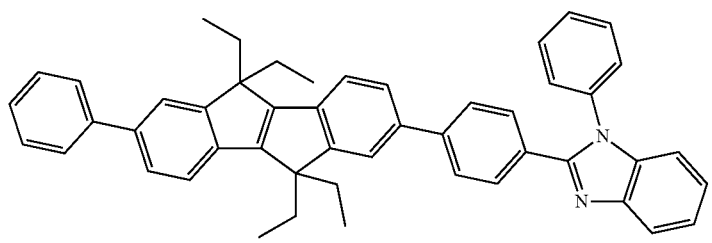
69
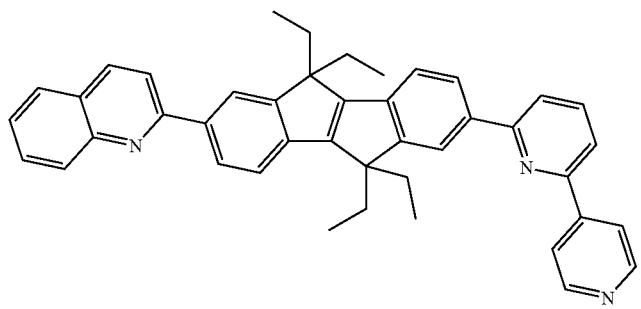

70
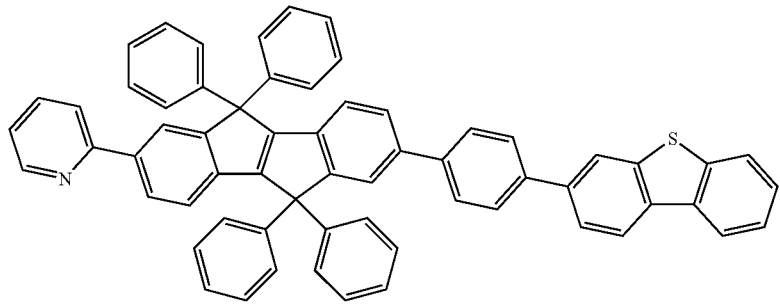
71
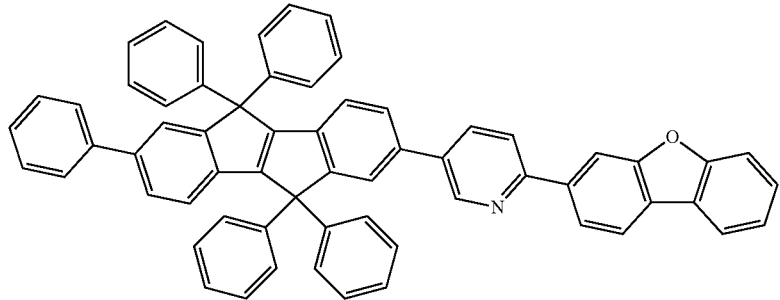
72
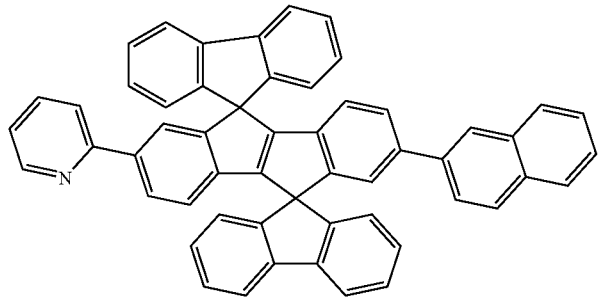
73
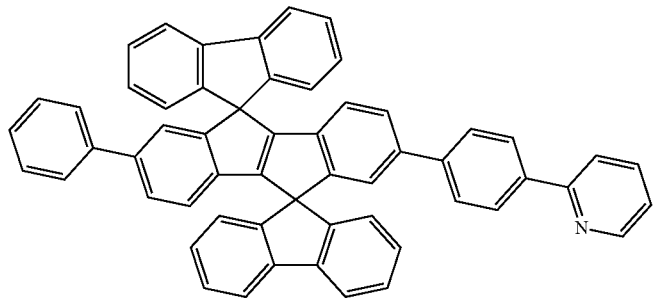
74
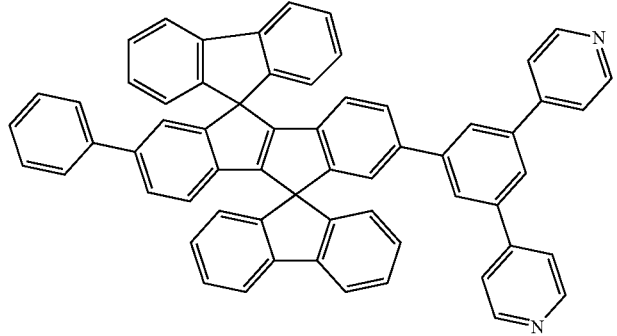

15. The organic light-emitting diode of claim 1, wherein the organic layer further comprises at least one of a hole injection layer, a hole transport layer, a functional layer having hole injection and hole transport abilities, a buffer layer, an electron blocking layer, a hole blocking layer, an electron injection layer, and a functional layer having electron injection and electron transport abilities.

16. The organic light-emitting diode of claim 1, wherein the electron transport layer further comprises a metal-containing material.

17. The organic light-emitting diode of claim 15, wherein the organic layer comprises at least one of a hole injection layer, a hole transport layer, and a functional layer having hole injection and hole transport abilities, wherein at least one of the hole injection layer, the hole transport layer, and the functional layer having hole injection and hole transport abilities comprises at least one of Compounds 301 through 320 below:

301

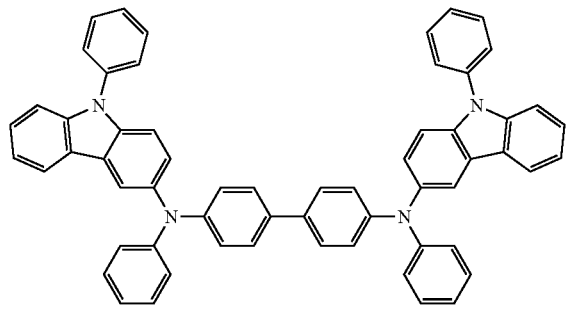

302

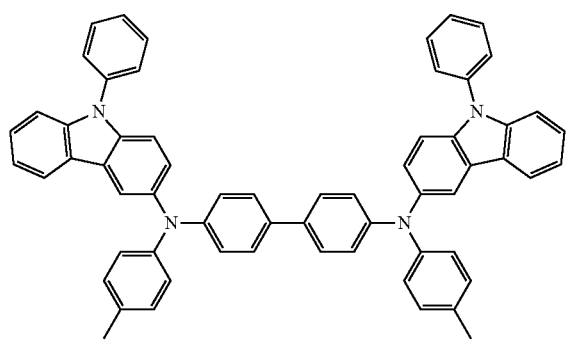

303

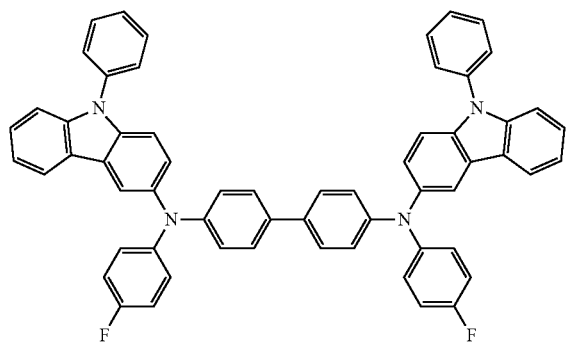

304

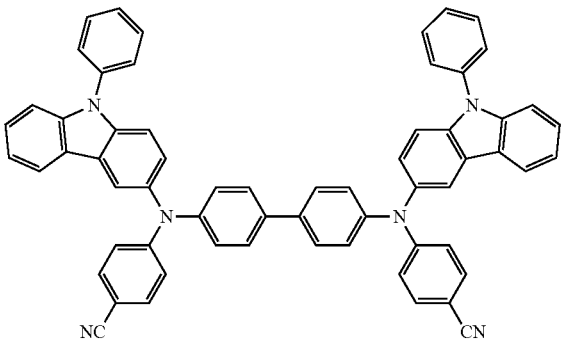

305

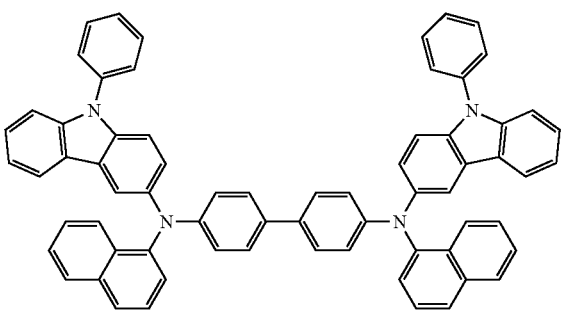

306

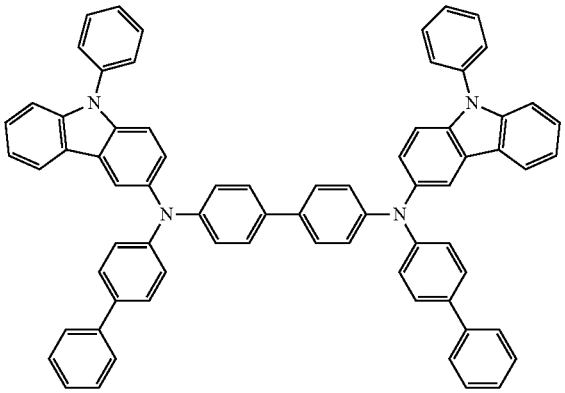

307

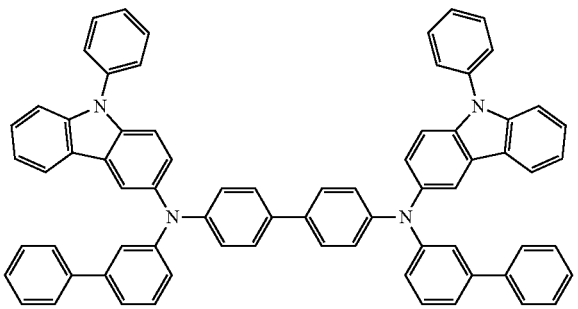

308
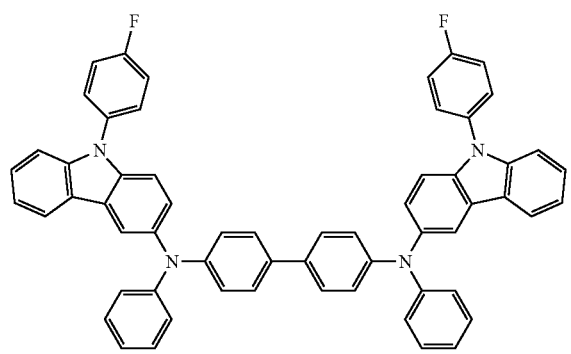
309
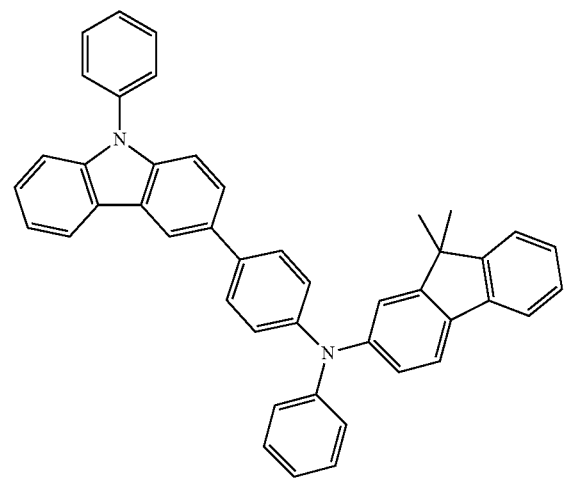
310
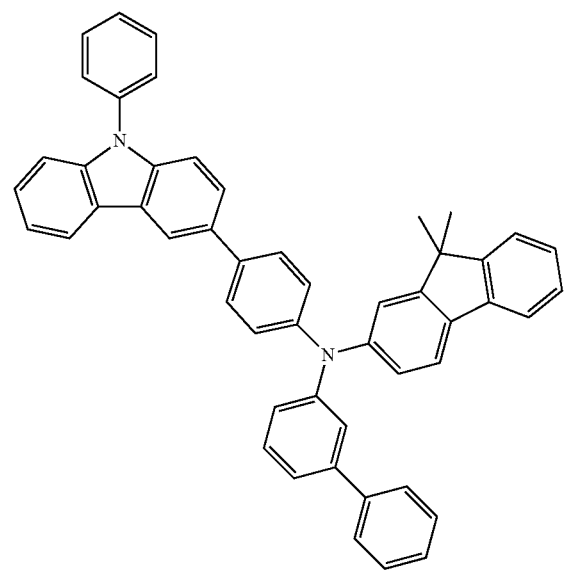
311
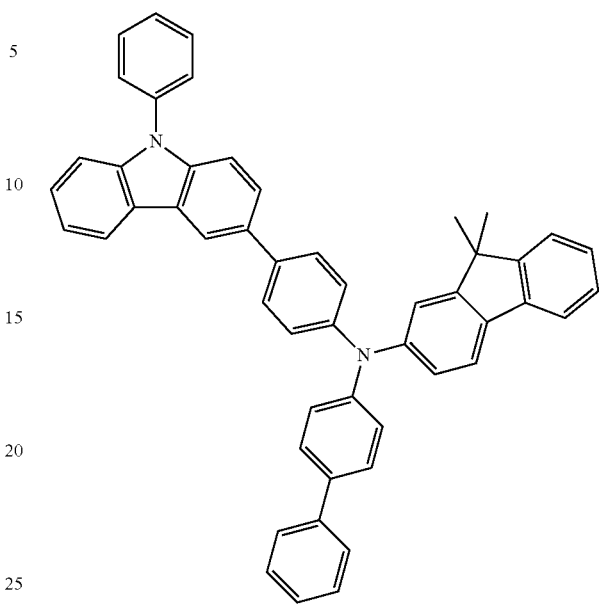
312
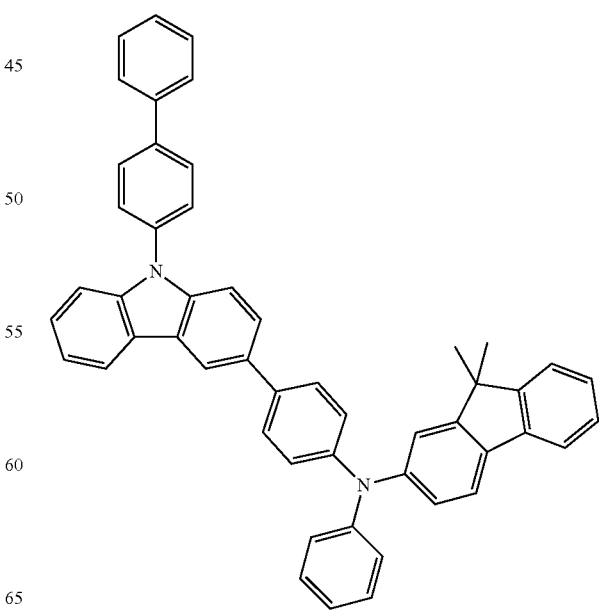

313
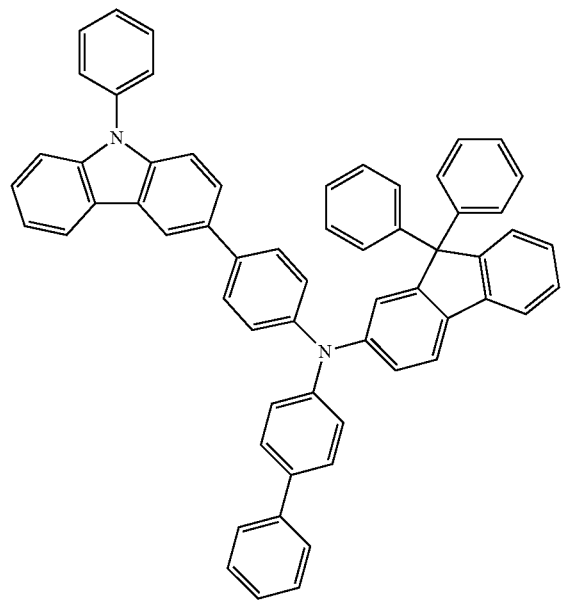
314
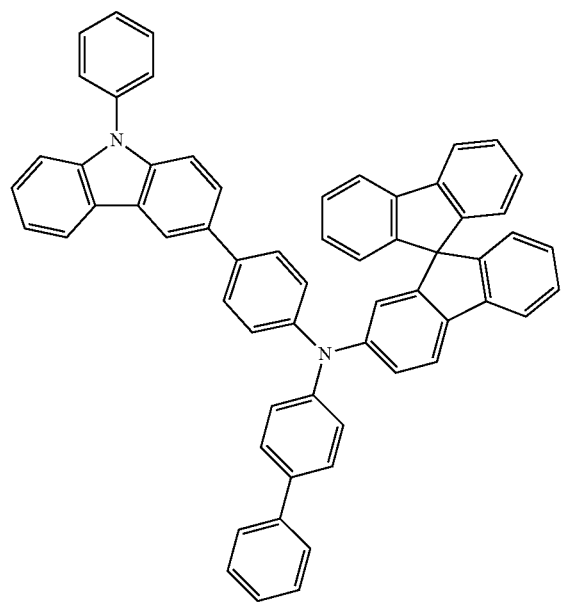
315
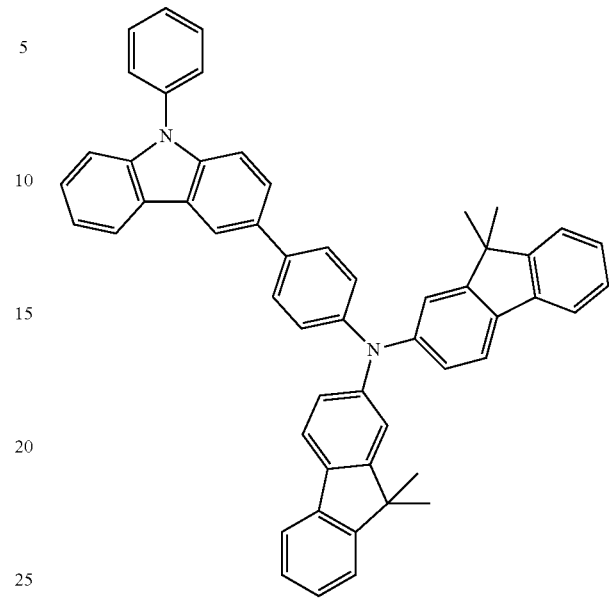
316
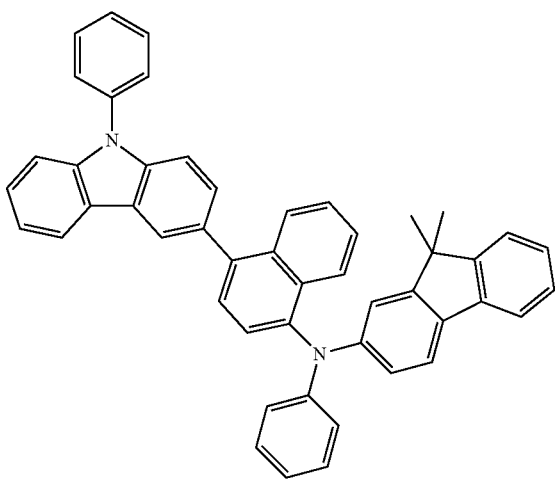

139
-continued
317
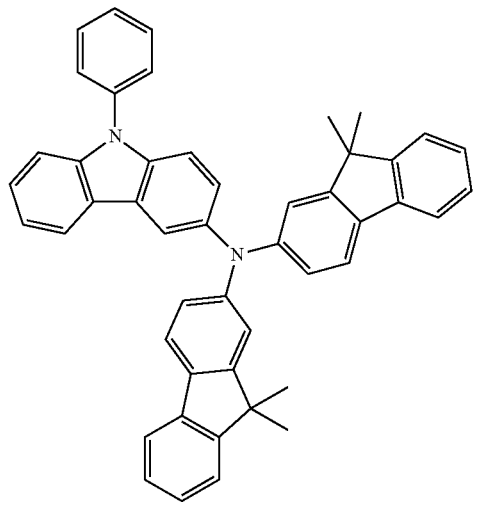
318
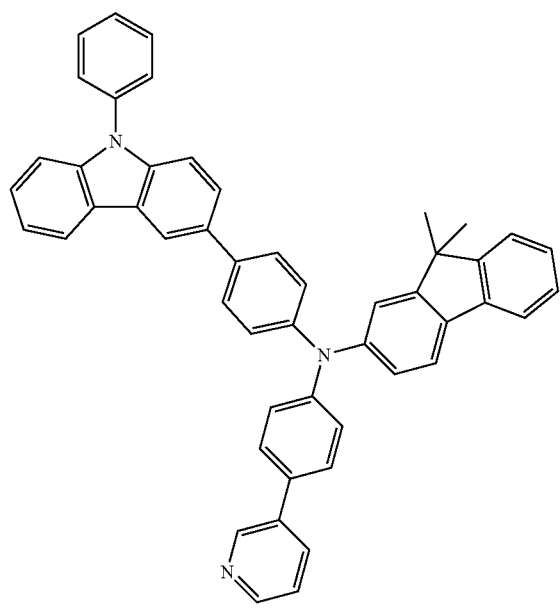
140
-continued
319
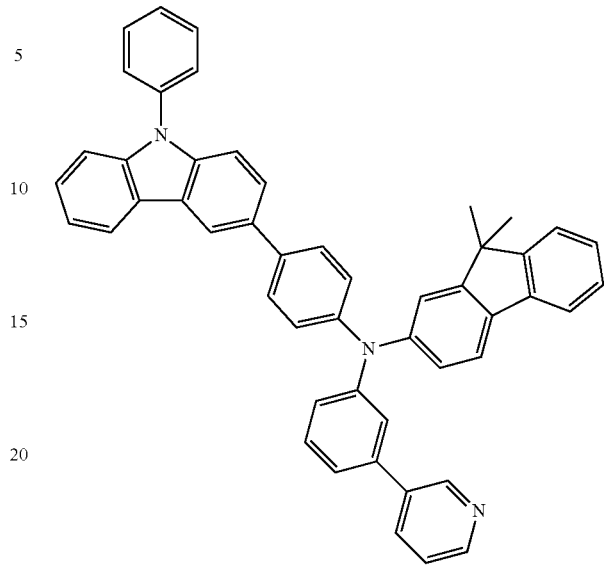
320
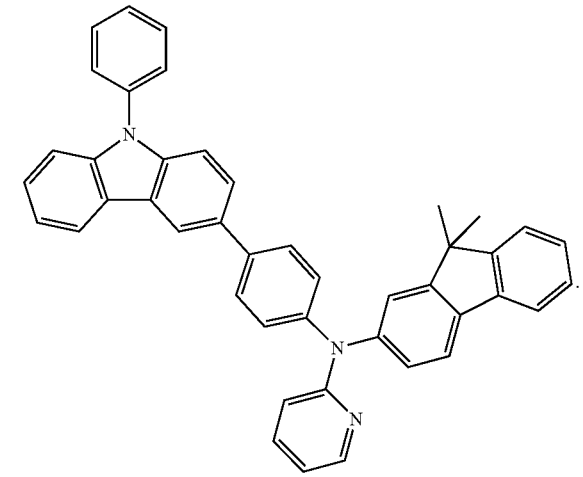
* * * * *